(12) United States Patent
Lu et al.

(10) Patent No.: US 10,344,034 B2
(45) Date of Patent: Jul. 9, 2019

(54) PYRAZOLOPYRIMIDONE OR PYRROLOTRIAZONE DERIVATIVES, METHOD OF PREPARING SAME, AND PHARMACEUTICAL APPLICATIONS THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Hejun Lu, Shanghai (CN); Piaoyang Sun, Jiangsu (CN); Bin Gui, Shanghai (CN); Qing Dong, Shanghai (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/969,098

(22) Filed: May 2, 2018

(65) Prior Publication Data

US 2018/0244679 A1 Aug. 30, 2018

Related U.S. Application Data

(62) Division of application No. 15/031,410, filed as application No. PCT/CN2014/087906 on Sep. 30, 2014, now Pat. No. 10,005,781.

(30) Foreign Application Priority Data

Oct. 30, 2013 (CN) .......................... 2013 1 0525956

(51) Int. Cl.
*C07D 487/04* (2006.01)
(52) U.S. Cl.
CPC .................... *C07D 487/04* (2013.01)
(58) Field of Classification Search
None
See application file for complete search history.

(56) References Cited

U.S. PATENT DOCUMENTS

| 5,171,835 A | 12/1992 | Janaky et al. |
| 2002/0065309 A1 | 5/2002 | Peng et al. |

FOREIGN PATENT DOCUMENTS

| CN | 101076531 A | 11/2007 |
| CN | 102361873 A | 2/2012 |
| CN | 102807568 A | 12/2012 |
| WO | 2004014916 A1 | 2/2004 |
| WO | 2006074051 A2 | 7/2006 |
| WO | 2006096785 A1 | 9/2006 |
| WO | 2010026993 A1 | 3/2010 |
| WO | 2011076687 A1 | 6/2011 |
| WO | 2012175514 A1 | 12/2012 |
| WO | 2013129879 A1 | 9/2013 |

OTHER PUBLICATIONS

International Search Report dated Jan. 12, 2015 in International Application No. PCT/CN2014/087906.
Bienstock et al., "Conformational Analysis of a Highly Potent Dicyclic Gonadotropin-Releasing Hormone Antagonist by Nuclear Magnetic Resonance and Molecular Dynamics," Journal of Medicinal Chemistry, vol. 36, pp. 3265-3273 (1993).

*Primary Examiner* — Sreenivasan Padmanabhan
*Assistant Examiner* — Jody L Karol
(74) *Attorney, Agent, or Firm* — Panitch Schwarze Belisario & Nadel LLP

(57) ABSTRACT

Methods of preparation and pharmaceutical uses of pyrazolopyrimidone derivatives are described. Specifically, methods of preparation and pharmaceutical uses of pyrazolopyrimidone derivatives represented by the general formula (II) and pharmaceutically acceptable salts thereof are described, wherein the definitions of substituents in the general formula (II) are the same as the definitions in the specification. The pyrazolopyrimidone derivatives are useful as gonadotropin releasing hormone (GnRH) antagonists, such as for therapeutic agents for endometriosis.

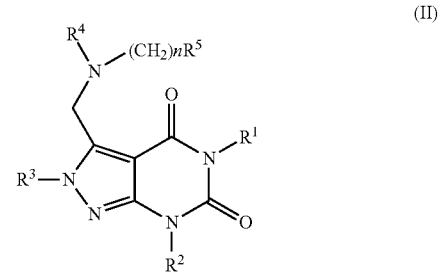

11 Claims, No Drawings

PYRAZOLOPYRIMIDONE OR PYRROLOTRIAZONE DERIVATIVES, METHOD OF PREPARING SAME, AND PHARMACEUTICAL APPLICATIONS THEREOF

CROSS-REFERENCE TO RELATED APPLICATION

This application is a Division of co-pending U.S. patent application Ser. No. 15/031,410 filed Apr. 22, 2016, which was a Section 371 of International Application No. PCT/CN2014/087906, filed Sep. 30, 2014, which was published in the Chinese language on May 7, 2015, under International Publication No. WO 2015/062391 A1, which claims priority under 35 U.S.C. § 119(b) to Chinese Application No. 201310525956.9, filed Oct. 30, 2013, the disclosures of which are incorporated herein by reference in its/their entirety.

FIELD OF THE INVENTION

The present invention relates to a novel pyrazolopyrimidone derivative or pyrrolotriazone derivative and a pharmaceutically acceptable salt thereof, a preparation method thereof, and a pharmaceutical composition containing the same, as well as use of the same as a gonadotropin-releasing hormone (GnRH) receptor antagonist, particularly as a therapeutic agent for the diseases such as endometriosis.

BACKGROUND OF THE INVENTION

Endometriosis is a common estrogen-dependent gynecological disease, which often occurs in women of childbearing-age, though the mechanism is unclear. The difficult diagnosis and unclear pathogenesis of endometriosis severely hinder the discovery of effective treatments. At present, endometriosis is mainly diagnosed by laparoscopy, and treated by surgery, or controlled by taking contraceptives, GnRH receptor agonists, or progestogen to reduce body estrogen levels.

Presently, the incidence rate of endometriosis is high. Statistical data from Datamonitor 2009 shows that the number of female patients suffering from endometriosis has been more than 68 million in only two countries (India and China) (31,288,000 in India, 37,535,000 in China), while the data in the seven major markets has been more than 17 million. Datamonitor expects that during 2009-2018, the endometriosis drug market will grow from $764 million in 2009 ($596 million in US, $117 million in European Union, $51 million in Japan) to $1.156 billion in 2018 ($844 million in US, $206 million in European Union, $106 million in Japan), and the growing space in the Chinese market will be larger.

Gonadotropin-releasing hormone (Gonadoliberin; GnRH), also known as luteinizing hormone releasing hormone (LHRH), is a decapeptide hormone (pGlu-His-Trp-Ser-Tyr-Gly-Leu-Arg-Pro-Gly-NH2) synthesized by hypothalamic neuroendocrine cells, and is a central regulatory factor of the endocrine reproductive system. GnRH plays an important role in the hypothalamus-pituitary-gonadal axis system by being transported to the pituitary through the hypothalamic pituitary portal circulation system and then binding to GnRH receptor cells in the anterior pituitary, by promoting the secretion and release of gonadotropin luteinizing hormones, such as Luteinizing Hormone (LH) and follicle-stimulating hormone (FSH), and by regulating normal development of the ovary and corpus luteum. GnRH receptor plays its regulatory role by coupling with G protein, which is capable of activating the calcium phosphatidylinositol second messenger system. LH regulates the production of sex steroids, and FSH regulates male spermatogenesis and maturation of female ovarian follicles.

LH and FSH are released into circulation, and bind to receptors on the specific cells of ovaries or testes to stimulate steroid production. Diseases such as endometriosis, uterine leiomyoma, and prostate cancer are aggravated in the presence of sex steroids. It is necessary to administer long-acting peptideGnRH receptor agonists and antagonists to control the diseases.

Peptide GnRH receptor antagonists include GnRH-derived linear peptides (U.S. Pat. No. 5,171,835), cyclic hexapeptide derivatives (US 2002/0065309), bicyclic peptide derivatives (Journal of Medicinal Chemistry, 1993; 36: 3265-73), etc.; and peptide GnRH receptor agonists include Leuprorelin (pGlu-His-Trp-Ser-Tyr-d-Leu-Leu-Arg-Pro-NHEt). However, there are many unresolved issues for peptide compounds including oral absorption, dosage form, dose volume, drug stability, sustained action, and metabolic stability and the like. The primary reason that small molecule GnRH receptor antagonist therapy is superior to the existing peptide-based therapy is largely due to the oral administration of small molecule GnRH receptor antagonists, which is convenient and efficient. Studies have shown that small molecule antagonists have a significant efficacy for hormone-dependent diseases such as endometriosis, precocious puberty, and prostate cancer.

An indirect tumor inhibition mechanism mediated by GnRH agonists is that GnRH agonists decrease the secretion of sex hormones and then indirectly inhibit the growth of tumor cells by long-term effects on the hypothalamic-pituitary-gonadal axis, which leads to a reduction of pituitary gonadotropins (FSH, LH), whereas GnRH receptor antagonists directly inhibit the release of pituitary gonadotropins, and then inhibit the growth of tumor cells.

In view of the limitations of peptide GnRH receptor antagonists, certain non-peptide GnRH receptor antagonists have been proposed and put into development, clinical trials, and marketing stages. For example, Elagolix (also known as NBI-56418 or ABT-620), is a small molecule GnRH receptor antagonist co-developed by Abbott and Neurocrine Biosciences Inc, which is currently in phase III clinical stage, and mainly used for the treatment of endometriosis (phase III) and uterine leiomyoma (phase II). In June 2012, the data from the endometriosis phase II trial were presented at the 94th Annual Meeting of the Endocrine Society in Houston. Among the 131 women suffering from endometriosis who were treated with elagolix (150 or 250 mg qd), leuprorelin depot (3.75 mg sc, once a monthfor 12 weeks) or placebo, the serum estrogen level in the patients of the elagolix treatment group was lower than that of the leuprorelin treatment group and placebo group. Meanwhile, the safety and tolerability of elagolix has been well verified.

Relugolix, also known as TAK-385, is an oral small molecule GnRH receptor antagonist developed by Takeda Pharmaceutical in Japan, which is used for the treatment of endometriosis, uterine leiomyoma, and prostate cancer. The study of endometriosis and uterine leiomyoma has been in phase II clinical trials since 2011, and the study of prostate cancer has been in phase I clinical trials since the same year.

At present, a series of patent applications concerning small molecule GnRH receptor antagonists have been published, including WO2006096785, WO2010026993, WO2011076687, WO2012175514, etc.

Despite numerous significant studies that have been conducted in this field, there remains a need to develop more effective small molecule GnRH receptor antagonists. The present disclosure provides structurally new GnRH receptor antagonists, and it is found that compounds having such structures have good activity, and exhibit excellent treatment effects for endocrine reproductive system diseases.

SUMMARY OF THE INVENTION

The present invention is directed to provide a compound of formula (I), or a tautomer, mesomer, racemate, enantiomer, or diastereomer thereof, or a mixture thereof, or a pharmaceutically acceptable salt thereof:

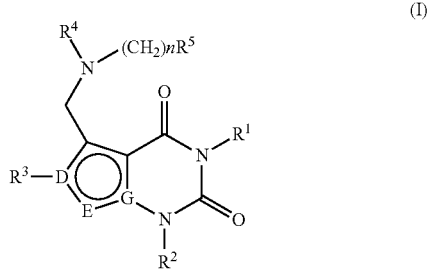

(I)

wherein:
when G is N, D is C and E is —CH—;
when G is C, D and E are N;

$R^1$ is selected from the group consisting of alkyl, cycloalkyl, heterocyclyl, aryl, heteroaryl, and —$OR^6$, wherein the alkyl, cycloalkyl, heterocyclyl, aryl, and heteroaryl are each independently and optionally further substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —$OR^6$, —$C(O)OR^6$, —$OC(O)R^6$, —$NHS(O)_mR^6$, —$C(O)R^6$, —$NHC(O)R^6$, —$NR^7R^8$, —$OC(O)NR^7R^8$, —$C(O)NR^7R^8$, —$NHC(O)NHR^6$, —$NHC(O)OR^6$, and —$NHC(O)NHOR^6$;

$R^2$ is alkyl, wherein the alkyl is further substituted with one or more groups selected from aryl and heteroaryl, wherein the aryl and heteroaryl are each optionally further substituted with one or more groups selected from the group consisting of halogen, alkyl, haloalkyl, cyano, nitro, —$C(O)OR^6$, —$C(O)NR^7R^8$, —$OC(O)NR^7R^8$, —$OR^6$, —$NHS(O)_mR^6$, —$NHC(O)R^6$, and —$NR^7R^8$, wherein the haloalkyl is preferably trifluoromethyl;

$R^3$ is selected from the group consisting of aryl and heteroaryl, wherein the aryl and heteroaryl are each optionally further substituted with one or more groups selected from the group consisting of halogen, alkyl, haloalkyl, —$OR^6$, —$C(O)OR^6$, —$OC(O)R^6$, —$C(O)R^6$, —$NR^7R^8$, —$OC(O)NR^7R^8$, —$C(O)NR^7R^8$, —$NHS(O)_mR^6$, —$NHC(O)R^6$, —$NHC(O)OR^6$, —$NHC(O)NHR^6$, and —$NHC(O)NHOR^6$;

$R^4$ is alkyl;

$R^5$ is selected from the group consisting of hydrogen, cycloalkyl, heterocyclyl, aryl, heteroaryl, —$OR^5$, —$NR^7R^8$, and —$NR^7S(O)_mR^6$, wherein the alkyl, cycloalkyl, heterocyclyl, aryl, and heteroaryl are each optionally further substituted with one or more groups selected from the group consisting of halogen, oxo, alkyl, haloalkyl, hydroxyalkyl, —$OR^6$, —$C(O)OR^6$, —$OC(O)R^6$, —$NR^7S(O)_mR^6$, —$S(O)_mR^6$, —$C(O)R^6$, and —$NHC(O)R^6$;

$R^6$ is selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally further substituted with one or more groups selected from the group consisting of alkyl, halogen, hydroxyl, alkoxy, cycloalkyl, heterocyclyl, aryl, heteroaryl, carboxylic acid, and carboxylic ester;

$R^7$ and $R^8$ are each independently selected from the group consisting of hydrogen, alkyl, cycloalkyl, heterocyclyl, aryl, and heteroaryl, wherein the alkyl, cycloalkyl, heterocyclyl, aryl and heteroaryl are each independently and optionally further substituted with one or more groups selected from the group consisting of alkyl, halogen, hydroxy, alkoxy, cycloalkyl, heterocyclyl, aryl, heteroaryl, carboxylic acid, and carboxylic ester; or, $R^7$ and $R^8$ are taken together with the attached N atom to form a heterocyclyl, wherein the heterocyclyl contains one or more heteroatoms of N, O, or $S(O)_m$, and the heterocyclyl is optionally further substituted with one or more groups selected from the group consisting of alkyl, halogen, hydroxyl, alkoxy, cycloalkyl, heterocyclyl, aryl, heteroaryl, carboxylic acid, and carboxylic ester;

m is 0, 1 or 2;
n is 1, 2, 3 or 4; and
p is 0, 1 or 2.

In a preferred embodiment of the present invention, the compound of formula (I), or a tautomer, mesomer, racemate, enantiomer, or diastereomer thereof, or mixture thereof, or a pharmaceutically acceptable salt thereof, is a compound of formula (II), or a tautomer, mesomer, racemate, enantiomer, diastereomer, or mixture thereof, or a pharmaceutically acceptable salt thereof:

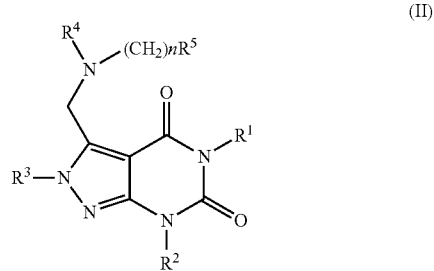

(II)

wherein: n, and $R^1$ to $R^5$ are as defined in formula (I).

In another preferred embodiment of the present invention, the compound of formula (I), or a tautomer, mesomer, racemate, enantiomer, or diastereomer thereof, or mixture thereof, or a pharmaceutically acceptable salt thereof, is a compound of formula (III), or a tautomer, mesomer, racemate, enantiomer, or diastereomer thereof, or mixture thereof, or a pharmaceutically acceptable salt thereof:

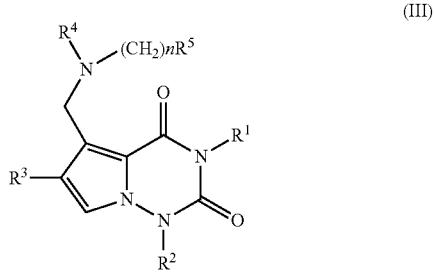

(III)

wherein: n, and $R^1$ to $R^5$ are as defined in formula (I).

In another preferred embodiment of the present invention, the compound of formula (I), or a tautomer, mesomer, racemate, enantiomer, or diastereomer thereof, or mixture thereof, or a pharmaceutically acceptable salt thereof, wherein $R^1$ is selected from the group consisting of aryl and heteroaryl, preferably phenyl and pyridazinyl, wherein the aryl and heteroaryl are each optionally further substituted with one or more groups selected from the group consisting of halogen, cyano, nitro, alkyl, haloalkyl, hydroxyalkyl, and —$OR^6$.

In another preferred embodiment of the present invention, the compound of formula (I), or a tautomer, mesomer, racemate, enantiomer, or diastereomer thereof, or mixture thereof, or a pharmaceutically acceptable salt thereof, wherein $R^2$ is benzyl, wherein the benzyl is optionally further substituted with one or more groups selected from the group consisting of halogen, alkyl, haloalkyl, cyano, nitro, and —$OR^6$.

In another preferred embodiment of the present invention, the compound of formula (I), or a tautomer, mesomer, racemate, enantiomer, or diastereomer thereof, or mixture thereof, or a pharmaceutically acceptable salt thereof, wherein $R^3$ is selected from aryl, preferably phenyl, wherein the aryl is optionally further substituted with one or more groups selected from the group consisting of —$NHC(O)R^6$, —$NHC(O)OR^6$, —$NHC(O)NHR^6$ and —$NHC(O)NHOR^6$, preferably —$NHC(O)NHR^6$, and —$NHC(O)NHOR^6$.

In another preferred embodiment of the present invention, the compound of formula (I), or a tautomer, mesomer, racemate, enantiomer, or diastereomer thereof, or mixture thereof, or a pharmaceutically acceptable salt thereof, wherein $R^4$ is methyl.

In another preferred embodiment of the present invention, the compound of formula (I), or a tautomer, mesomer, racemate, enantiomer, or diastereomer thereof, or mixture thereof, or a pharmaceutically acceptable salt thereof, wherein $R^5$ is hydrogen, and n is 1 or 2.

In another preferred embodiment of the present invention, the compound of formula (I), or a tautomer, mesomer, racemate, enantiomer, or diastereomer thereof, or mixture thereof, or a pharmaceutically acceptable salt thereof, is a compound of formula (IV), or a tautomer, mesomer, racemate, enantiomer, or diastereomer thereof, or mixture thereof, or a pharmaceutically acceptable salt thereof:

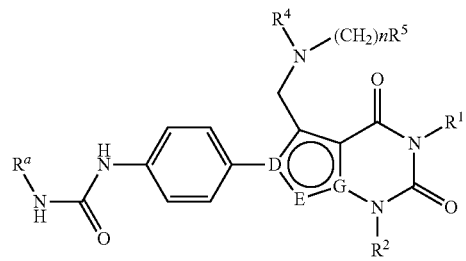

(IV)

wherein: n, D, E, G, $R^1$, $R^2$, $R^4$, and $R^5$ are as defined in formula (I);

$R^a$ is selected from the group consisting of alkyl and —$OR^6$, wherein the alkyl is optionally further substituted with one or more groups selected from the group consisting of alkyl, halogen, hydroxy, alkoxy, cycloalkyl, heterocyclyl, aryl, heteroaryl, carboxylic acid, and carboxylic ester; and $R^6$ is alkyl, wherein the alkyl is optionally further substituted with one or more groups selected from the group consisting of alkyl, halogen, hydroxy, alkoxy, cycloalkyl, heterocyclyl, aryl, heteroaryl, carboxylic acid, and carboxylic ester.

Typical compounds of the present invention include, but are not limited to, the following:

| Example No. | Structure and Name |
|---|---|
| 1 | <br>N-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)acetamide |

| Example No. | Structure and Name |
|---|---|
| 2 | 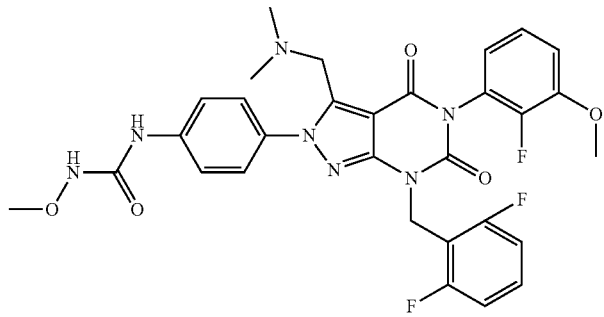

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methoxyurea |
| 3 | 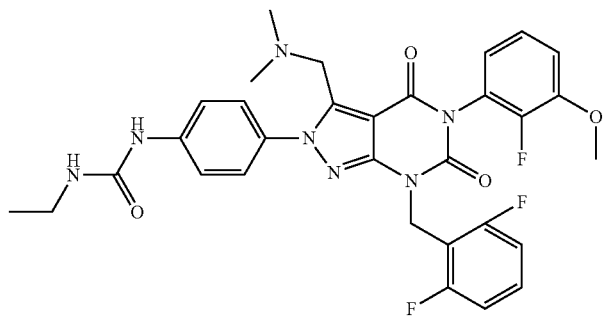 [SMILES: CCNC(=O)Nc1ccc(-n2nc3c(c2CN(C)C)c(=O)n(-c2cccc(OC)c2F)c(=O)n3Cc2c(F)cccc2F)cc1]

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-ethylurea |
| 4 | 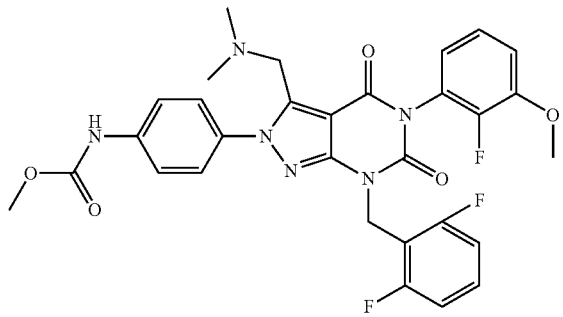

methyl (4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)carbamate |

| Example No. | Structure and Name |
|---|---|
| 5 | 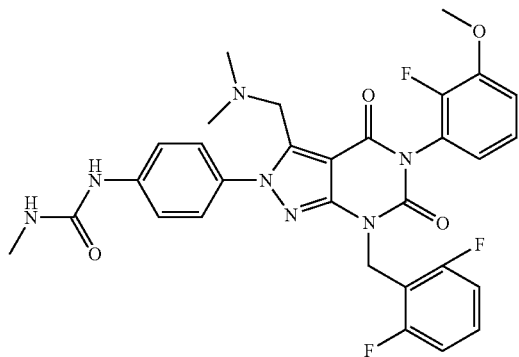 [SMILES: CNC(=O)Nc1ccc(-n2nc3c(c2CN(C)C)c(=O)n(-c2cccc(OC)c2F)c(=O)n3Cc2c(F)cccc2F)cc1]<br>1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methylurea |
| 6 | 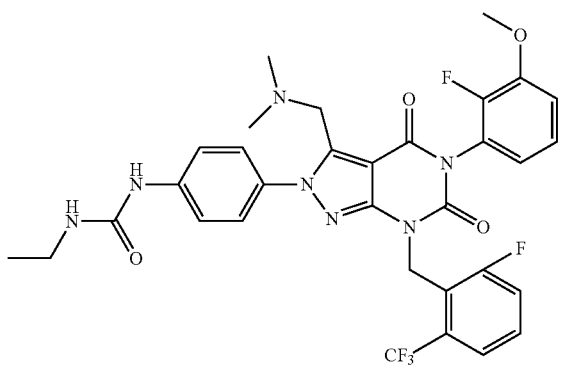 [SMILES: CCNC(=O)Nc1ccc(-n2nc3c(c2CN(C)C)c(=O)n(-c2cccc(OC)c2F)c(=O)n3Cc2c(F)cccc2C(F)(F)F)cc1]<br>1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-ethylurea |
| 7 | 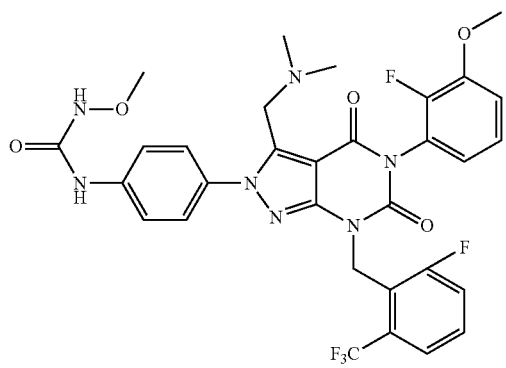 [SMILES: CONC(=O)Nc1ccc(-n2nc3c(c2CN(C)C)c(=O)n(-c2cccc(OC)c2F)c(=O)n3Cc2c(F)cccc2C(F)(F)F)cc1]<br>1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methoxyurea |

| Example No. | Structure and Name |
|---|---|
| 8 | 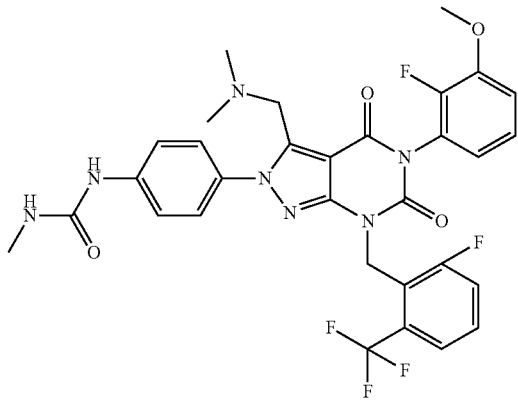 [SMILES: CNC(=O)Nc1ccc(-n2nc3c(c2CN(C)C)c(=O)n(-c2cccc(OC)c2F)c(=O)n3Cc2c(F)cccc2C(F)(F)F)cc1]<br>1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methylurea |
| 9 | 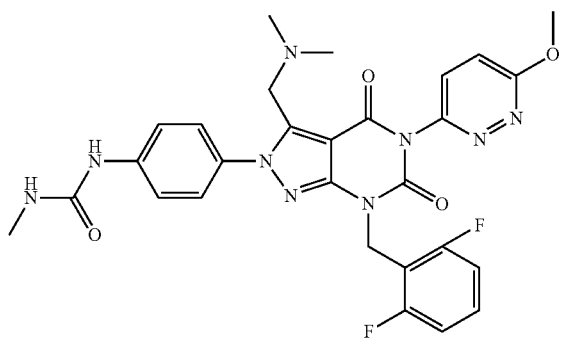<br>1-(4-(7-(2,6-difluorobenzyl)-3-((dimethylamino)methyl)-5-(6-methoxy-pyridazin-3-yl)-4,6-dioxo-4,5,6,7-tetrahydro-2H-pyrazolo[3,4-d]pyrimidin-2-yl)phenyl)-3-methylurea |
| 10 | 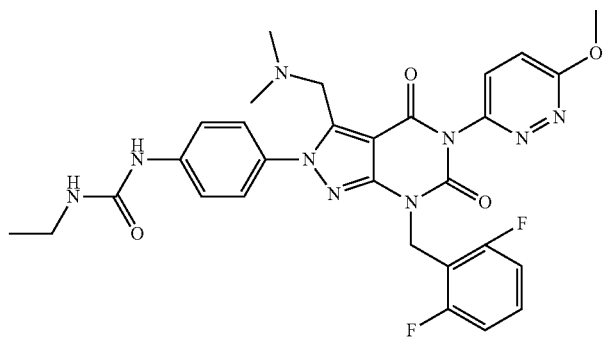 [SMILES: CCNC(=O)Nc1ccc(-n2nc3c(c2CN(C)C)c(=O)n(-c2ccc(OC)nn2)c(=O)n3Cc2c(F)cccc2F)cc1]<br>1-(4-(7-(2,6-difluorobenzyl)-3-((dimethylamino)methyl)-5-(6-methoxy-pyridazin-3-yl)-4,6-dioxo-4,5,6,7-tetrahydro-2H-pyrazolo[3,4-d]pyrimidin-2-yl)phenyl)-3-ethylurea |

-continued

| Example No. | Structure and Name |
|---|---|
| 11 | 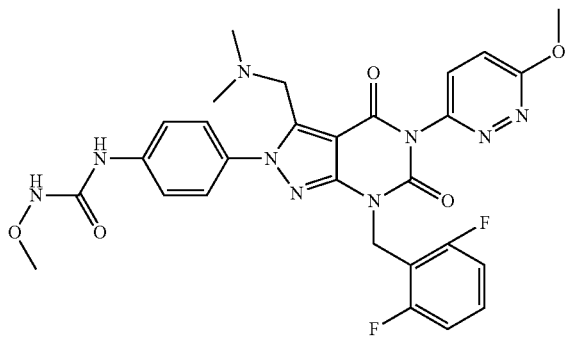 [SMILES: CONC(=O)Nc1ccc(-n2nc3c(c2CN(C)C)c(=O)n(-c2ccc(OC)nn2)c(=O)n3Cc2c(F)cccc2F)cc1]<br>1-(4-(7-(2,6-difluorobenzyl)-3-((dimethylamino)methyl)-5-(6-methoxy-pyridazin-3-yl)-4,6-dioxo-4,5,6,7-tetrahydro-2H-pyrazolo[3,4-d]pyrimidin-2-yl)phenyl)-3-methoxyurea |
| 12 | 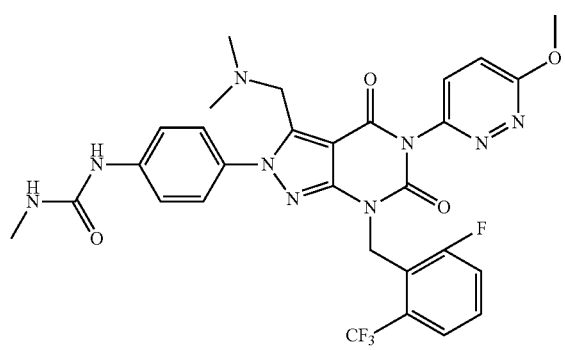<br>1-(4-(3-((dimethylamino)methyl)-7-(2-fluoro-6-(trifluoromethyl)benzyl)-5-(6-methoxypyridazin-3-yl)-4,6-dioxo-4,5,6,7-tetrahydro-2H-pyrazolo[3,4-d]pyrimidin-2-yl)phenyl)-3-methylurea |
| 13 | 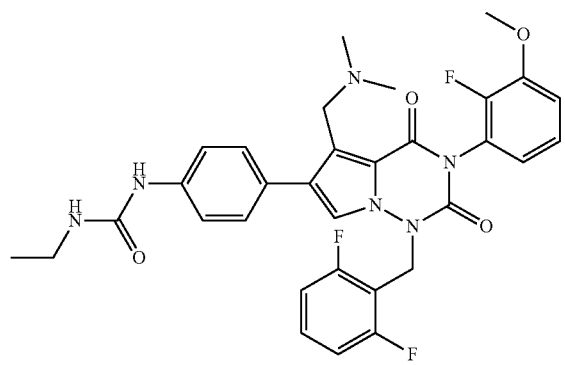 [SMILES: CCNC(=O)Nc1ccc(-c2cn3c(c2CN(C)C)c(=O)n(-c2cccc(OC)c2F)c(=O)n3Cc2c(F)cccc2F)cc1]<br>1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-ethylurea |

| Example No. | Structure and Name |
|---|---|
| 14 | 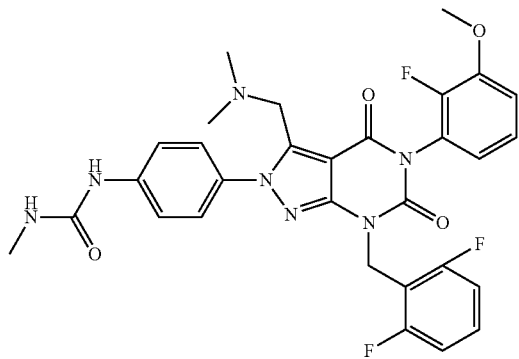 [SMILES: CNC(=O)Nc1ccc(-n2nc3c(c2CN(C)C)c(=O)n(-c2cccc(OC)c2F)c(=O)n3Cc2c(F)cccc2F)cc1]<br>1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methylurea |
| 15 | 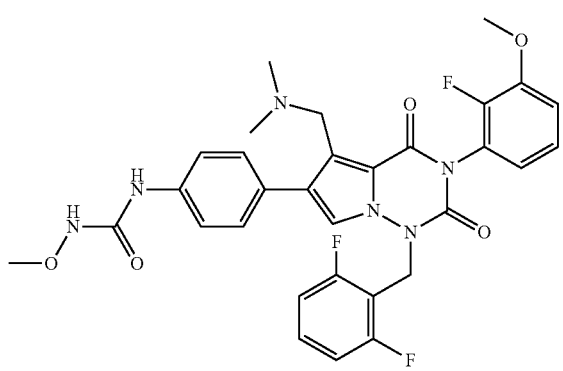 [SMILES: CONC(=O)Nc1ccc(-c2cn3c(c2CN(C)C)c(=O)n(-c2cccc(OC)c2F)c(=O)n3Cc2c(F)cccc2F)cc1]<br>1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methoxyurea |
| 16 | 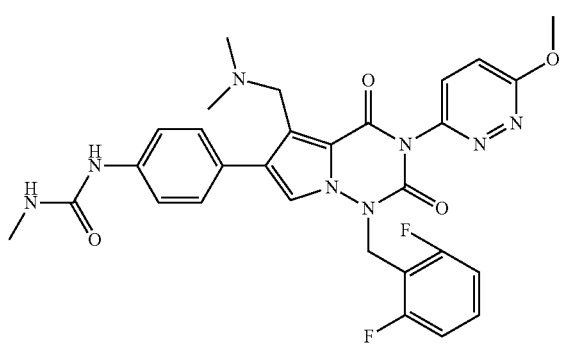<br>1-(4-(1-(2,6-difluorobenzyl)-5-((dimethylamino)methyl)-3-(6-methoxy-pyridazin-3-yl)-2,4-dioxo-1,2,3,4-tetrahydropyrrolo[2,1-f][1,2,4]triazin-6-yl)phenyl)-3-methylurea |

| Example No. | Structure and Name |
|---|---|
| 17 | 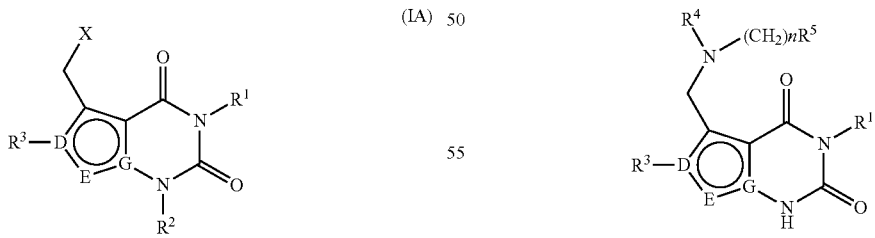

1-(4-(7-(2,6-difluorobenzyl)-3-((dimethylamino)methyl)-5-(6-hydroxy-pyridazin-3-yl)-4,6-dioxo-4,5,6,7-tetrahydro-2H-pyrazolo[3,4-d]pyrimidin-2-yl)phenyl)-3-methoxyurea |
| 18 | 1-(4-(1-(2,6-difluorobenzyl)-5-((dimethylamino)methyl)-3-(6-methoxy-pyridazin-3-yl)-2,4-dioxo-1,2,3,4-tetrahydropyrrolo[2,1-f][1,2,4]triazin-6-yl)phenyl)-3-methoxyurea | or a tautomer, mesomer, racemate, enantiomer, or diastereomer thereof, or mixture thereof, or a pharmaceutically acceptable salt thereof.

In another aspect, the present invention provides a process for preparing the compound of formula (I), or a tautomer, mesomer, racemate, enantiomer, or diastereomer thereof, or mixture thereof, or a pharmaceutically acceptable salt thereof, comprising a step of:

(IA)

reacting a compound of formula (IA) with the amine of $NH(R^4)(CH_2)nR^5$; optionally reducing and/or acylating the resulting product to obtain the compound of formula (I); wherein: X is halogen; and n, D, E, G and $R^1$ to $R^5$ are as defined in formula (I).

Reducing agents include, but are not limited to, hydrogen and iron powder; Acylating agents include, but are not limited to, carboxylic acids, acyl chloride, sulfuryl chloride, halogenated methyl formate, isocyanate, triphosgene, and methoxyamine.

In another aspect, the present invention provides a process for preparing the compound of formula (I), or a tautomer, mesomer, racemate, enantiomer, or diastereomer thereof, or mixture thereof, or a pharmaceutically acceptable salt thereof, comprising a step of:

(IB)

reacting a compound of formula (IB) with $R^2X$ in the presence of an alkaline reagent; optionally reducing and/or acylating the resulting product to obtain the compound of formula (I);
wherein: X is halogen, and n, D, E, G and $R^1$ to $R^5$ are as defined in formula (I).

Alkaline reagents include, but are not limited to, organic bases and inorganic bases, wherein the organic base includes, but is not limited to, triethylamine, pyridine, 2,6-lutidine, sodium methoxide, lithium hexamethyldisilazide, sodium hexamethyldisilazide, n-butyllithium, potassium tert-butoxide, and tetrabutyl ammonium bromide; the inorganic base includes, but is not limited to, sodium hydride, sodium carbonate, sodium bicarbonate, potassium carbonate, potassium bicarbonate, cesium carbonate, lithium hydroxide, sodium hydroxide, and potassium hydroxide, preferably potassium carbonate and sodium methoxide.

Reducing agents include, but are not limited to, hydrogen and iron powder;

Acylating agents include, but are not limited to, carboxylic acids, acyl chloride, sulfuryl chloride, halogenated methyl formate, isocyanate, triphosgene, and methoxyamine.

A compound of formula (IA) or formula (IB), or a pharmaceutically acceptable salt thereof, which is used as an intermediate in the preparation of a compound of formula (I):

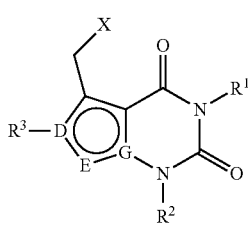
(IA)

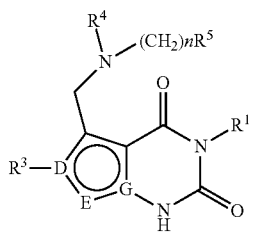
(IB)

wherein: X is halogen, and n, D, E, G and $R^1$ to $R^5$ are as defined in formula (I).

A process for preparing the compound of formula (IA), or a pharmaceutically acceptable salt thereof, comprising a step of:

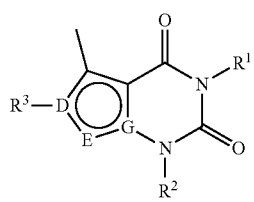
(Ib)

performing a halogenation reaction of a compound of formula (Ib) to obtain the compound of formula (IA);
wherein: D, E, G and $R^1$ to $R^3$ are as defined in formula (I).

A process for preparing the compound of formula (IB), or a pharmaceutically acceptable salt thereof, comprising a step of:

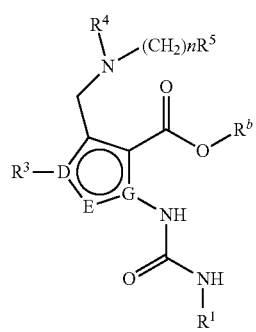
(Ig)

performing a cyclization reaction of a compound of formula (Ig) obtain the compound of formula (IB);
wherein: n, D, E, G, and $R^1$, $R^3$ to $R^5$ are as defined in formula (I); and $R^b$ is alkyl.

Typical compounds of formula (IA) include, but are not limited to, the following:

| Example No. | Structure and Name |
|---|---|
| 1f | ![structure] 3-(bromomethyl)-7-(2,6-difluorobenzyl)-5-(2-fluoro-3-methoxyphenyl)-2-(4-nitrophenyl)-2H-pyrazolo[3,4-d]pyrimidine-4,6(5H,7H)-dione |
| 6b | ![structure] 3-(bromomethyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione |
| 9e | ![structure] 3-((dimethylamino)methyl)-5-(6-methoxypyridazin-3-yl)-2-(4-nitrophenyl)-2H-pyrazolo[3,4-d]pyrimidine-4,6(5H,7H)-dione |

| Example No. | Structure and Name |
|---|---|
| 12d | 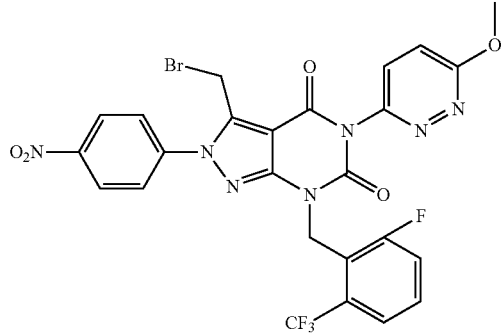 [SMILES: COc1ccc(-n2c(=O)c3c(CBr)n(-c4ccc([N+](=O)[O-])cc4)nc3n(Cc3c(F)cccc3C(F)(F)F)c2=O)nn1]  3-(bromomethyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione |
| 13h | 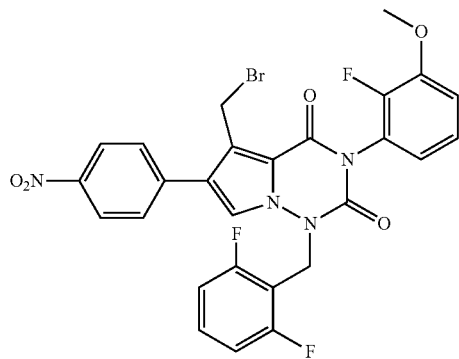 [SMILES: COc1cccc(-n2c(=O)c3c(CBr)c(-c4ccc([N+](=O)[O-])cc4)cn3n(Cc3c(F)cccc3F)c2=O)c1F]  5-(bromomethyl)-1-(2,6-difluorobenzyl)-3-(2-fluoro-3-methoxyphenyl)-6-(4-nitrophenyl)pyrrolo[2,1-f][1,2,4]triazine-2,4(1H,3H)-dione |
| 16h | 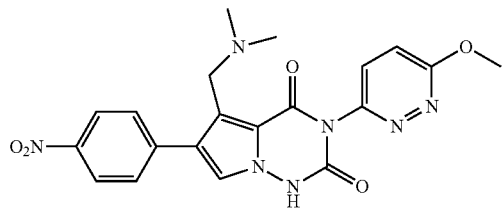 [SMILES: COc1ccc(-n2c(=O)[nH]n3cc(-c4ccc([N+](=O)[O-])cc4)c(CN(C)C)c3c2=O)nn1]  5-((dimethylamino)methyl)-3-(6-methoxypyridazin-3-yl)-6-(4-nitrophenyl)pyrrolo[2,1-f][1,2,4]triazine-2,4(1H,3H)-dione | or a tautomer, mesomer, racemate, enantiomer, or diastereomer thereof, or mixture thereof, or a pharmaceutically acceptable salt thereof.

A compound of formula (IVA), or a pharmaceutically acceptable salt thereof, which is used as an intermediate in the preparation of a compound of formula (IV):

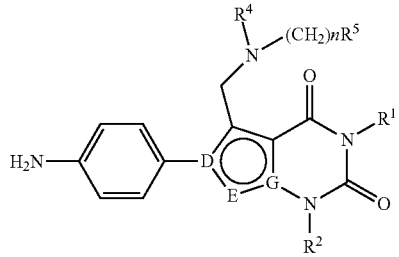

(IVA)

wherein: n, D, E, G, $R^1$, $R^2$, $R^4$, and $R^5$ are as defined in formula (I).

Typical compounds of formula (IVA) include, but are not limited to the following:

| Example No. | Structure and Name |
|---|---|
| 1h | 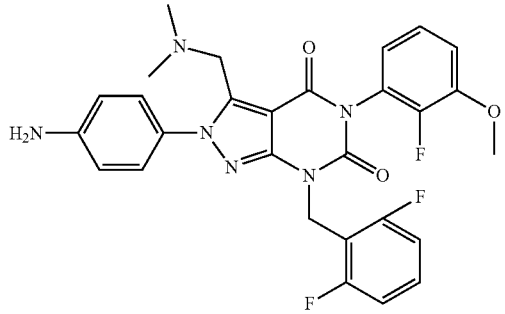 [SMILES: COc1cccc(-n2c(=O)c3c(CN(C)C)n(-c4ccc(N)cc4)nc3n(Cc3c(F)cccc3F)c2=O)c1F]  2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione |
| 6d | 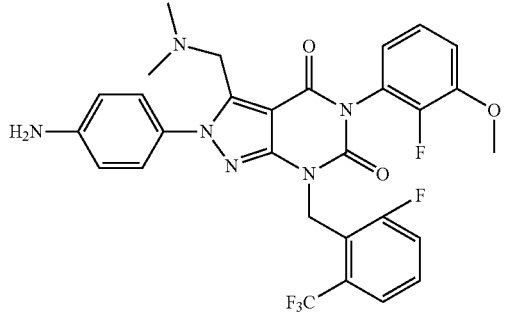 [SMILES: COc1cccc(-n2c(=O)c3c(CN(C)C)n(-c4ccc(N)cc4)nc3n(Cc3c(F)cccc3C(F)(F)F)c2=O)c1F]  2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione |
| 9g | 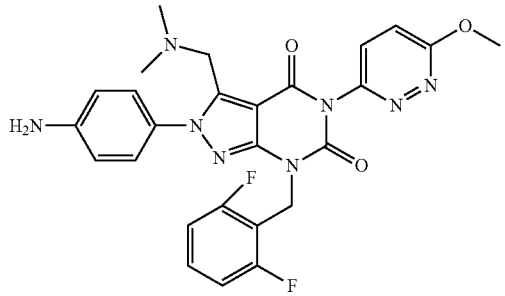 [SMILES: COc1ccc(-n2c(=O)c3c(CN(C)C)n(-c4ccc(N)cc4)nc3n(Cc3c(F)cccc3F)c2=O)nn1] |

-continued

| Example No. | Structure and Name |
|---|---|
| 12f | 2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione<br>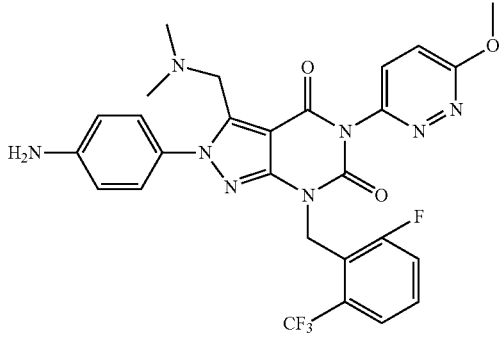 [SMILES: COc1ccc(-n2c(=O)c3c(CN(C)C)n(-c4ccc(N)cc4)nc3n(Cc3c(F)cccc3C(F)(F)F)c2=O)nn1]<br>2-(4-aminophenyl)-3-((dimethylamino)methyl)-7-(2-fluoro-6-(trifluoromethyl)benzyl)-5-(6-methoxypyridazin-3-yl)-2H-pyrazolo[3,4-d]pyrimidine-4,6(5H,7H)-dione |
| 13j | 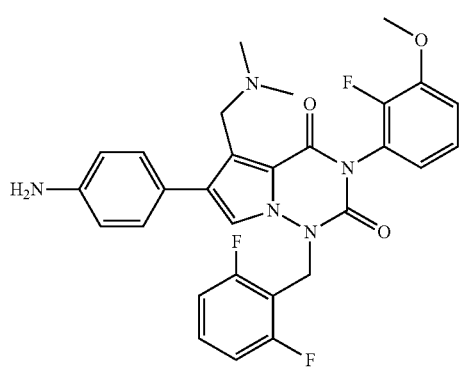 [SMILES: COc1cccc(-n2c(=O)c3c(CN(C)C)c(-c4ccc(N)cc4)cn3n(Cc3c(F)cccc3F)c2=O)c1F]<br>6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione |
| 16j | 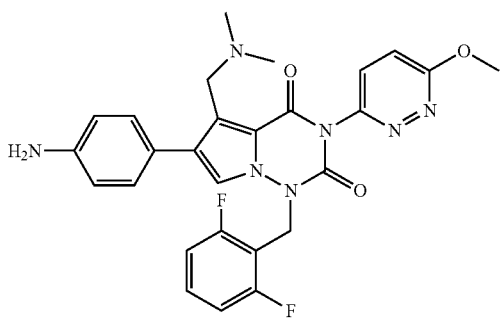 [SMILES: COc1ccc(-n2c(=O)c3c(CN(C)C)c(-c4ccc(N)cc4)cn3n(Cc3c(F)cccc3F)c2=O)nn1]<br>6-(4-aminophenyl)-1-(2,6-difluorobenzyl)-5-((dimethylamino)methyl)-3-(6-methoxypyridazin-3-yl)pyrrolo[2,1-f][1,2,4]triazine-2,4(1H,3H)-dione | or a tautomer, mesomer, racemate, enantiomer, or diastereomer thereof, or mixture thereof, or a pharmaceutically acceptable salt thereof.

A process for preparing the compound of formula (IV), comprising a step of:

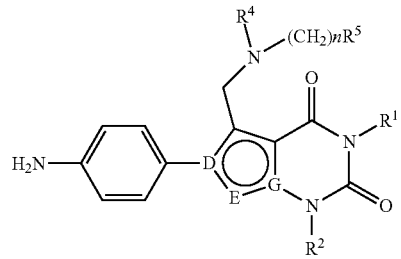

(IVA)

further reacting the compound of formula (IVA) with an acylating agent to obtain a compound of formula (IV); wherein: n, D, E, G, $R^1$, $R^2$, $R^4$, and $R^5$ are as defined in formula (I).

Acylating agents include, but are not limited to, carboxylic acids, acyl chloride, sulfuryl chloride, halogenated methyl formate, isocyanate, triphosgene, and methoxyamine.

The present invention further relates to a pharmaceutical composition, comprising a therapeutically effective amount of a compound of formula (I), or a tautomer, mesomer, racemate, enantiomer, or diastereomer thereof, or mixture thereof, or a pharmaceutically acceptable salt thereof, and one or more pharmaceutically acceptable carriers, diluents, or excipients.

The present invention further relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament as a GnRH receptor antagonist.

The present invention further relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for the treatment of gonadal hormone-related diseases.

The present invention further relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of medicaments for the treatment or prevention of sex hormone-dependent cancers (e.g., prostatic cancer, uterine cancer, breast cancer, pituitary cancer, etc.), bone metastasis of sex hormone-dependent cancers, prostatic hyperplasia, uterine leiomyoma, endometriosis, uterine fibroids, precocious puberty, amenorrhea, premenstrual syndrome, dysmenorrhea, multilocular ovary syndrome, polycystic ovary syndrome, acne, alopecia, Alzheimer's disease, infertility, irritable bowel syndrome, benign or malignant tumors which are hormone-independent and LH-RH sensitive, or flush; or in the preparation of a reproductive regulator, contraceptive, or an ovulation stimulant; or in the preparation of medicaments for the treatment or prevention of postoperative recurrence of sex hormone-dependent cancer, preferably prostate cancer, uterine cancer, breast cancer, endometriosis or uterine leiomyoma.

The present invention further relates to a method for inhibiting GnRH receptor activity, comprising administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition containing the same.

The present invention further relates to a method for treating a gonadal hormone-related disease, comprising administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition containing the same.

The present invention further relates to a method for the prevention or treatment of sex hormone-dependent cancers (prostate cancer, uterine cancer, breast cancer, pituitary cancer, etc.), bone metastatic sex hormone-dependent cancer, prostatic hyperplasia, uterine leiomyoma, endometriosis, uterine fibroids, precocious puberty, amenorrhea, premenstrual syndrome, dysmenorrhea, multilocular ovary syndrome, polycystic ovary syndrome, acne, alopecia, Alzheimer's disease, infertility, irritable bowel syndrome, benign or malignant tumors which are hormone-independent and LH-RH sensitive, or flush, preferably prostate cancer, uterine cancer, breast cancer, endometriosis, or uterine leiomyoma; or for regulating reproduction, contraception or stimulating ovulation; or for the prevention of postoperative recurrence of sex hormone-dependent cancer.

The present invention also relates to a compound of formula (I), or a tautomer, mesomer, racemate, enantiomer, or diastereomer thereof, or mixture thereof, or a pharmaceutically acceptable salt thereof, or a pharmaceutical composition containing the same, for use as a medicament for inhibiting the activity of GnRH receptor.

The present invention also relates to a compound of the formula (I), or a tautomer, mesomer, racemate, enantiomer, or diastereomer thereof, or mixture thereof, or a pharmaceutically acceptable salt thereof, or a pharmaceutical composition containing the same, for use as a medicament for the treatment of sex hormone-related diseases.

The present invention further relates to a compound of formula (I), or a tautomer, mesomer, racemate, enantiomer, or diastereomer thereof, or mixture thereof, or a pharmaceutically acceptable salt thereof, or a pharmaceutical composition containing the same, for use as a preventative or regulatory agent for hormone-dependent diseases, particularly; or for use as a preventative or therapeutic agent for sex hormone-dependent cancers (e.g., prostatic cancer, uterine cancer, breast cancer, pituitary cancer, etc.), prostatic hyperplasia, uterine leiomyoma, endometriosis, uterine fibroids, precocious puberty, amenorrhea syndrome, premenstrual syndrome, multilocular ovary syndrome, acne, alopecia, Alzheimer's disease, etc.; or for use as a pregnancy regulator (contraceptive and the like), infertility therapeutic agent, or menstruation regulator; or for use as a preventative or therapeutic agent for irritable bowel syndrome; or for use as a preventative agent for post-operative recurrence of sex hormone-dependent cancer, and the like; preferably prostate cancer, uterine cancer, breast cancer, endometriosis, or uterine leiomyoma.

The pharmaceutical compositions containing the active ingredient can be in a form suitable for oral administration, such as tablets, troches, lozenges, aqueous or oily suspensions, dispersible powders or granules, emulsions, hard or soft capsules, or syrups or elixirs. Oral compositions can be prepared according to any known method for the preparation of pharmaceutical compositions in the art. Such compositions can contain one or more additives selected from the group consisting of sweetener, flavoring agents, colorant, and preservatives, to provide a pleasing and palatable pharmaceutical formulation. Tablets contain the active ingredient and nontoxic pharmaceutically acceptable excipients suitable for the manufacture of tablets. These excipients can be inert excipients, such as calcium carbonate, sodium carbonate, lactose, calcium phosphate or sodium phosphate; granulating and disintegrating agents, such as microcrystalline cellulose, cross-linked sodium carboxymethyl cellulose, corn starch or alginic acid; binder such as starch, gelatin, polyvinylpyrrolidone or acacia; and lubricant, such as magnesium stearate, stearic acid or talc. The tablets can be uncoated or coated by means of known techniques which can mask drug taste or delay the disintegration and absorption of a drug in the gastrointestinal tract, thereby providing sustained release over an extended period. For example, the water soluble taste masking material which can be used in the present invention is such as hydroxypropyl methylcellulose or hydroxypropyl cellulose, or the sustained release material which can be used in the present invention is such as ethyl cellulose, cellulose acetate butyrate.

Oral formulations can also be provided as hard gelatin capsules in which the active ingredient is mixed with an inert solid diluent, such as calcium carbonate, calcium phosphate or kaolin, or as soft gelatin capsules in which the active ingredient is mixed with a water soluble carrier, such as polyethyleneglycol or an oil medium, for example peanut oil, liquid paraffin, or olive oil.

Aqueous suspensions contain the active ingredient in admixture with excipients suitable for the manufacture of aqueous suspensions. Such excipients are suspending agents, such as sodium carboxymethylcellulose, methylcellulose, hydroxypropylmethylcellulose, sodium alginate, polyvinylpyrrolidone, and gum acacia; dispersants or humectants, which may be a naturally occurring phosphatide, such as lecithin, or condensation products of an alkylene oxide with fatty acids, such as polyoxyethylene stearate, or condensation products of ethylene oxide with long chain aliphatic alcohol, such as heptadecaethyleneoxy cetanol, or condensation products of ethylene oxide with part esters derived from fatty acids and hexitols, such as polyoxyethylene sorbitol monooleate, or condensation products of ethylene oxide with partial esters derived from fatty acids and hexitol anhydrides, such as polyoxyethylene sorbitan monooleate. The aqueous suspension can also contain one or more preservatives, such as ethylparaben or n-propylparaben, one or more colorants, one or more flavoring agents, and one or more sweeteners, such as sucrose, saccharin or aspartame.

Oil suspensions can be formulated by suspending the active ingredient in a vegetable oil, such as arachis oil, olive oil, sesame oil or coconut oil, or in a mineral oil, such as liquid paraffin. The oil suspension can contain a thickener, such as beeswax, hard paraffin or cetyl alcohol. The aforesaid sweetener and flavoring agents can be added to provide a palatable preparation. These compositions can be preserved by the addition of an antioxidant, such as butylated hydroxyanisole or α-tocopherol.

Dispersible powders and granules suitable for the preparation of an aqueous suspension by the addition of water provide the active ingredient in admixture with a dispersant or wetting agent, suspending agent, or one or more preservatives. Suitable dispersants or wetting agents and suspending agents are exemplified by those already mentioned above. Additional excipients, such as sweeteners, flavoring agents, and colorants, can also be added. These compositions can be preserved by the addition of an antioxidant, such as ascorbic acid.

The present pharmaceutical composition can also be in the form of an oil-in-water emulsion. The oil phase can be a vegetable oil, such as olive oil or *arachis* oil, or a mineral oil, such as liquid paraffin, or a mixture thereof. Suitable emulsifying agents can be naturally occurring phosphatides, such as soy bean lecithin, and esters or partial esters derived from fatty acids and hexitol anhydrides, such as sorbitan monooleate, and condensation products of the said partial esters with ethylene oxide, such as polyoxyethylene sorbitol monooleate. The emulsion can also contain sweeteners, flavoring agents, preservatives, and antioxidants. Syrups and elixirs can be formulated with sweetener, such as glycerol, propylene glycol, sorbitol or sucrose. Such formulations can also contain a demulcent, a preservative, a colorant, or an antioxidant.

The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be first dissolved in a mixture of soybean oil and lecithin, the oil solution then is introduced into a mixture of water and glycerol and processed to form a microemulsion. The injectable solutions or microemulsions can be introduced into an individual's bloodstream by local bolus injection. Alternatively, it may be advantageous to administer the solution or microemulsion in such a way as to maintain a constant circulating concentration of the present compound. In order to maintain such a constant concentration, a continuous intravenous delivery device may be utilized. An example of such device is Deltec CADD-PLUS™ 5400 intravenous injection pump.

The pharmaceutical composition can be in the form of a sterile injectable aqueous or oily suspension for intramuscular or subcutaneous administration. Such suspension can be formulated with suitable dispersant or wetting agents and suspending agents as described above according to known techniques. The sterile injectable preparation can also be a sterile injectable solution or suspension prepared in a nontoxic parenterally acceptable diluent or solvent, for example, a solution prepared in 1,3-butanediol. Moreover, a sterile fixed oil can easily be used as a solvent or suspending medium. For this purpose, any suitable fixed oils including synthetic mono- or di-glyceride can be employed. Moreover, fatty acids such as oleic acid can be employed in the preparation of injectables.

The present compound can be administered in the form of suppositories for rectal administration. These pharmaceutical compositions can be prepared by mixing drug with a suitable non-irritating excipient which is solid at regular room temperatures but liquid in the rectum, thereby melting in the rectum to release the drug. Such materials include cocoa butter, glycerinated gelatin, hydrogenated vegetable oils, mixture of polyethylene glycols and fatty acid esters of polyethylene glycol with various molecular weight.

It is well known to those skilled in the art that the dosage of a drug depends on a variety of factors including, but are not limited to, the following factors: activity of a particular compound, age of the patient, weight of the patient, general health of the patient, behavior of the patient, diet of the patient, time of administration, route of administration, rate of excretion, drug combination and the like. In addition, the best treatment, such as treatment model, daily dose of the compound of formula (I) or the type of pharmaceutically acceptable salt thereof can be verified by the traditional therapeutic regimen.

DETAILED DESCRIPTION OF THE INVENTION

Unless otherwise stated, the terms used in the specification and claims have the meanings described below.

"Alkyl" refers to a saturated aliphatic hydrocarbon group including $C_1$-$C_{20}$ linear and branched chain groups, preferably an alkyl having 1 to 10 carbon atoms, more preferably an alkyl having 1 to 6 carbon atoms, even more preferably an alkyl having 1 to 4 carbon atoms, and most preferably methyl. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point, and the substituent group(s) is preferably one or more groups independently selected from the group consisting of alkyl, alkenyl, alkynyl, alkyloxyl, alkylthiol, alkylamino, halogen, thiol, hydroxy, nitro, cyano, cycloalkyl, heterocyclyl, aryl, heteroaryl, cycloalkoxy, heterocyclic alkoxy, cycloalkylthio, heterocycloalkylthio, oxo, amino, haloalkyl, hydroxyalkyl, carboxyl, alkoxycarbonyl, —$OR^6$, —$C(O)OR^6$, —$OC(O)R^6$, —$NHS(O)_mR^6$, —$C(O)R^6$, —$NHC(O)R^6$, —$NHC(O)OR^6$, —$NR^7R^8$, —$OC(O)NR^7R^8$, —$C(O)NR^7R^8$, —$NHC(O)NHR^6$ and —$NHC(O)NHOR^6$.

"Alkenyl" refers to an alkyl defined as above that has at least two carbon atoms and at least one carbon-carbon double bond, for example, vinyl, 1-propenyl, 2-propenyl, 1-, 2-, or 3-butenyl, etc., preferably $C_{2-10}$ alkenyl, more preferably $C_{2-6}$ alkenyl, and most preferably $C_{2-4}$ alkenyl. The alkenyl group can be substituted or unsubstituted. When substituted, the substituent group(s) is preferably one or more group(s) independently selected from the group consisting of alkyl, alkenyl, alkynyl, alkoxy, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl, alkoxycarbonyl, —$OR^6$, —C(O)OR⁶, —OC(O)R⁶, —NHS(O)$_m$R⁶, —C(O)R⁶, —NHC(O)R⁶, —NHC(O)OR⁶, —NR⁷R⁸, —OC(O)NR⁷R⁸, —C(O)NR⁷R⁸, —NHC(O)NHR⁶ and —NHC(O)NHOR⁶.

"Alkynyl" refers to an alkyl defined as above that has at least two carbon atoms and at least one carbon-carbon triple bond, for example, ethynyl, 1-propynyl, 2-propynyl, 1-, 2-, or 3-butynyl, etc., preferably C$_{2-10}$ alkynyl, more preferably C$_{2-6}$ alkynyl, and most preferably C$_{2-4}$ alkynyl. The alkynyl group can be substituted or unsubstituted. When substituted, the substituent group(s) is preferably one or more group(s) independently selected from the group consisting of alkyl, alkenyl, alkynyl, alkoxy, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl, alkoxycarbonyl, —OR⁶, —C(O)OR⁶, —OC(O)R⁶, —NHS(O)$_m$R⁶, —C(O)R⁶, —NHC(O)R⁶, —NHC(O)OR⁶, —NR⁷R⁸, —OC(O)NR⁷R⁸, —C(O)NR⁷R⁸, —NHC(O)NHR⁶ and —NHC(O)NHOR⁶.

"Cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, even more preferably 3 to 6 carbon atoms, and most preferably cyclopropyl. Representative examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc., preferably cyclopropyl, or cyclohexenyl. Polycyclic cycloalkyl includes a cycloalkyl having a spiro ring, fused ring or bridged ring. The cycloalkyl group can be substituted or unsubstituted. When substituted, the substituent group(s) is preferably one or more groups independently selected from the group consisting of alkyl, alkenyl, alkynyl, alkyloxyl, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl, alkoxycarbonyl, —OR⁶, —C(O)OR⁶, —OC(O)R⁶, —NHS(O)$_m$R⁶, —C(O)R⁶, —NHC(O)R⁶, —NHC(O)OR⁶, —NR⁷R⁸, —OC(O)NR⁷R⁸, —C(O)NR⁷R⁸, —NHC(O)NHR⁶ and —NHC(O)NHOR⁶.

"Heterocyclyl" refers to a 3 to 20 membered saturated or partially unsaturated monocyclic or polycyclic hydrocarbon group having one or more heteroatoms selected from the group consisting of N, O, and S(O)$_m$ (wherein m is an integer between 0 and 2) as ring atoms, but excluding —O—O—, —O—S— or —S—S— in the ring, with the remaining ring atoms being C. A heterocyclyl preferably has 3 to 12 ring atoms, wherein 1 to 4 atoms are heteroatoms; more preferably 3 to 10 ring atoms; and most preferably 5 to 6 ring atoms. Representative examples of monocyclic heterocyclyl include, but are not limited to, pyrrolidinyl, piperidyl, piperazinyl, morpholinyl, thiomorpholinyl, homopiperazinyl, pyranyl, tetrahydrofuranyl, and the like. Polycyclic heterocyclyl includes the heterocyclyl having a spiro ring, fused ring or bridged ring. The heterocyclyl group can be substituted or unsubstituted. When substituted, the substituent group(s) is preferably one or more groups independently selected from the group consisting of alkyl, alkenyl, alkynyl, alkyloxyl, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxyl, alkoxycarbonyl, —OR⁶, —C(O)OR⁶, —OC(O)R⁶, —NHS(O)$_m$R⁶, —C(O)R⁶, —NHC(O)R⁶, —NHC(O)OR⁶, —NR⁷R⁸, —OC(O)NR⁷R⁸, —C(O)NR⁷R⁸, —NHC(O)NHR⁶ and —NHC(O)NHOR⁶.

"Aryl" refers to a 6 to 14 membered all-carbon monocyclic ring or polycyclic fused ring (a "fused" ring system means that each ring shares an adjacent pair of carbon atoms with another ring in the system), which has a completely conjugated π-electron system. An aryl is preferably 6 to 10 membered, more preferably phenyl and naphthyl, and most preferably phenyl. The aryl can be fused to the ring of a heteroaryl, heterocyclyl or cycloalkyl, wherein the ring bound to the parent structure is aryl. Representative examples include, but are not limited to, the following groups:

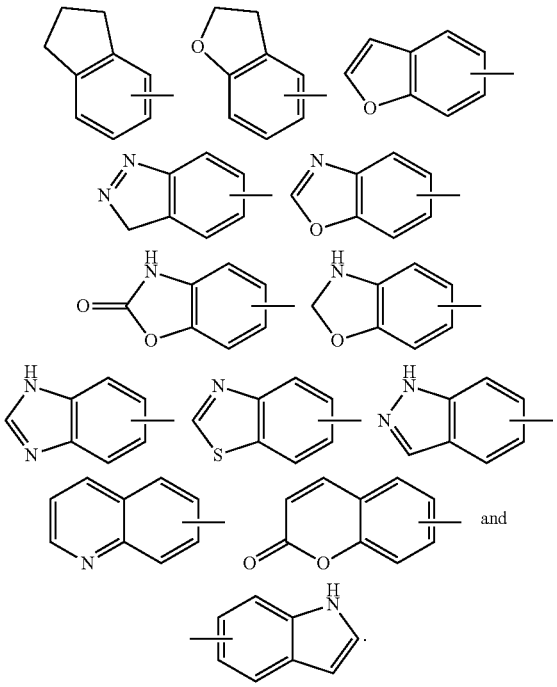

The aryl group can be substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, —OR⁶, —C(O)OR⁶, —OC(O)R⁶, —NHS(O)$_m$R⁶, —C(O)R⁶, —NHC(O)R⁶, —NHC(O)OR⁶, —NR⁷R⁸, —OC(O)NR⁷R⁸, —C(O)NR⁷R⁸, —NHC(O)NHR⁶ and —NHC(O)NHOR⁶.

"Heteroaryl" refers to 5 to 14 membered all-carbon monocyclic ring or polycyclic fused ring having 1 to 4 heteroatoms selected from the group consisting of O, S, and N, which has a completely conjugated π-electron system. A heteroaryl is preferably 5- to 10-membered, more preferably 5- or 6-membered, and most preferably furyl, thienyl, pyridinyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to the parent structure is heteroaryl. Representative examples include, but are not limited to, the following groups:

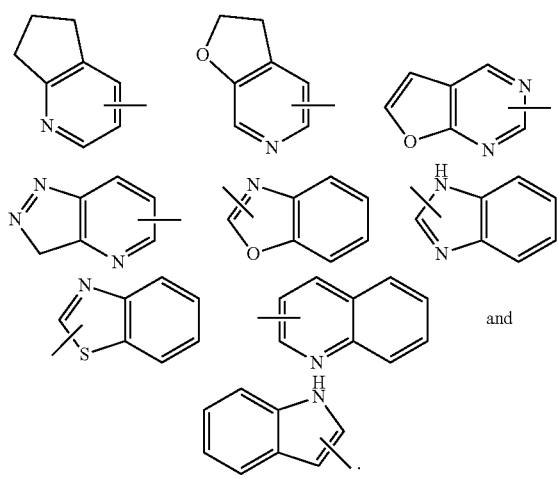

The heteroaryl group can be substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, —$OR^6$, —$C(O)OR^6$, —$OC(O)R^6$, —$NHS(O)_mR^6$, —$C(O)R^6$, —$NHC(O)R^6$, —$NHC(O)OR^6$, —$NR^7R^8$, —$OC(O)NR^7R^8$, —$C(O)NR^7R^8$, —$NHC(O)NHR^6$ and —$NHC(O)NHOR^6$.

"Alkoxy" refers to both an —O-(alkyl) and an —O-(unsubstituted cycloalkyl) group, wherein the alkyl and cycloalkyl are defined as above. Representative examples include, but are not limited to, methoxy, ethoxy, propoxy, butoxy, cyclopropyloxy, cyclobutyloxy, cyclopentyloxy, cyclohexyloxy, and the like. The alkoxy can be substituted or unsubstituted. When substituted, the substituent is preferably one or more group(s) independently selected from the group consisting of alkyl, alkenyl, alkynyl, alkoxy, alkylthiol, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, alkoxycarbonyl, —$OR^6$, —$C(O)OR^6$, —$OC(O)R^6$, —$NHS(O)_mR^6$, —$C(O)R^6$, —$NHC(O)R^6$, —$NHC(O)OR^6$, —$NR^7R^8$, —$OC(O)NR^7R^8$, —$C(O)NR^7R^8$, —$NHC(O)NHR^6$ and —$NHC(O)NHOR^6$.

"Haloalkyl" refers to an alkyl group substituted by one or more halogens, wherein the alkyl is as defined above.

"Hydroxy" refers to an —OH group.

"Hydroxy alkyl" refers to an alkyl group substituted by a hydroxy group, wherein the alkyl is as defined above.

"Halogen" refers to fluorine, chlorine, bromine, or bromine.

"Amino" refers to an —$NH_2$ group.

"Cyano" refers to a —CN group.

"Nitro" refers to a —$NO_2$ group.

"Oxo group" refers to a =O group.

"Carboxylic acid" refers to an (alkyl) or (cycloalkyl) —C(O)OH.

"Sulfuryl chloride" refers to an (alkyl) or (cycloalkyl) —S(O)m-X (halo).

"Isocyanate" refers to an (alkyl) or (cycloalkyl) —N=C=O.

"Triphosgene" refers to a bis(trichloromethyl)carbonate.

"Carboxyl" refers to a —C(O)OH group.

"Alkoxycarbonyl" refers to a —C(O)O(alkyl) or (cycloalkyl) group, wherein the alkyl and cycloalkyl are defined as above.

"Optional" or "optionally" means that the event or circumstance described subsequently can, but not necessary occur. Such expression means the case that the event or circumstance does or does not occur. For example, "the heterocyclic group optionally substituted by an alkyl" means that an alkyl group can be, but is not necessarily present, and such expression includes the case that the heterocyclic group is substituted with an alkyl and the heterocyclic group is not substituted with an alkyl.

"Substituted" refers to one or more hydrogen atoms in a group, preferably up to 5, more preferably 1 to 3 hydrogen atoms, each independently replaced with a corresponding number of substituents. It goes without saying that the substituents exist in their only possible chemical position. The person skilled in the art is able to determine whether the substitution is possible or impossible without paying excessive efforts by experiment or theory. For example, an amino or hydroxy group having a free hydrogen bound to carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof, and other chemical components such as physiologically/pharmaceutically acceptable carriers and excipients. The purpose of a pharmaceutical composition is to facilitate administration of a compound to an organism, which is conducive to the absorption of the active ingredient, thus displaying biological activity.

$R^6$~$R^8$ are as defined in formula (I).

Synthesis Method of the Present Compound

In order to achieve the object of the present invention, the present invention applies the following technical solution:

A process for preparing a compound of formula (I), or a tautomer, mesomer, racemate, enantiomer, or diastereomer thereof, or a mixture thereof, or a pharmaceutically acceptable salt thereof, comprises the following steps:

Scheme 1

(Ia)

(Ib)

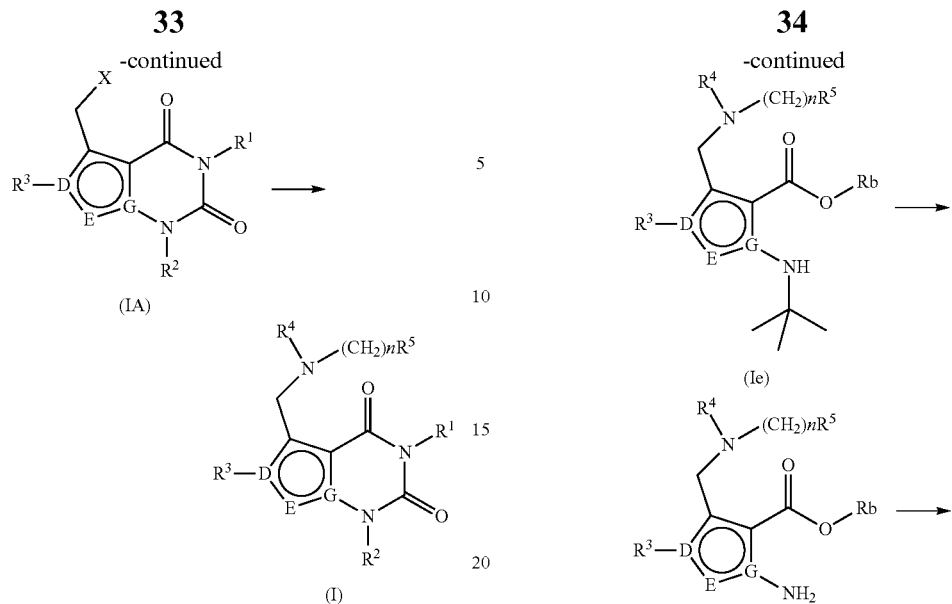

(IA)

(I)

a compound of formula (Ia) is reacted with R²X in the presence of an alkaline reagent to obtain a compound of formula (Ib); the compound of formula (Ib) is subjected to a halogenating reaction under a catalyst to obtain a compound of formula (IA), wherein the catalyst is preferably azobisisobutyronitrile, and the halogenating agent is preferably N-bromosuccinimide; the compound of formula (IA) is reacted with the amine of NH(R⁴)(CH₂)nR⁵ to obtain a compound of formula (I);

wherein: X is halogen; n, D, E, G, and R¹ to R⁵ are as defined in formula (I);

R³ is preferably an aryl, more preferably a phenyl, wherein the aryl is optionally further substituted with one or more groups selected from the group consisting of —NHC(O)NHR⁶ and —NHC(O)NHOR⁶.

A process for preparing a compound of formula (I), or a tautomer, mesomer, racemate, enantiomer, or diastereomer thereof, or a mixture thereof, or a pharmaceutically acceptable salt thereof, comprises the following steps:

Scheme 2

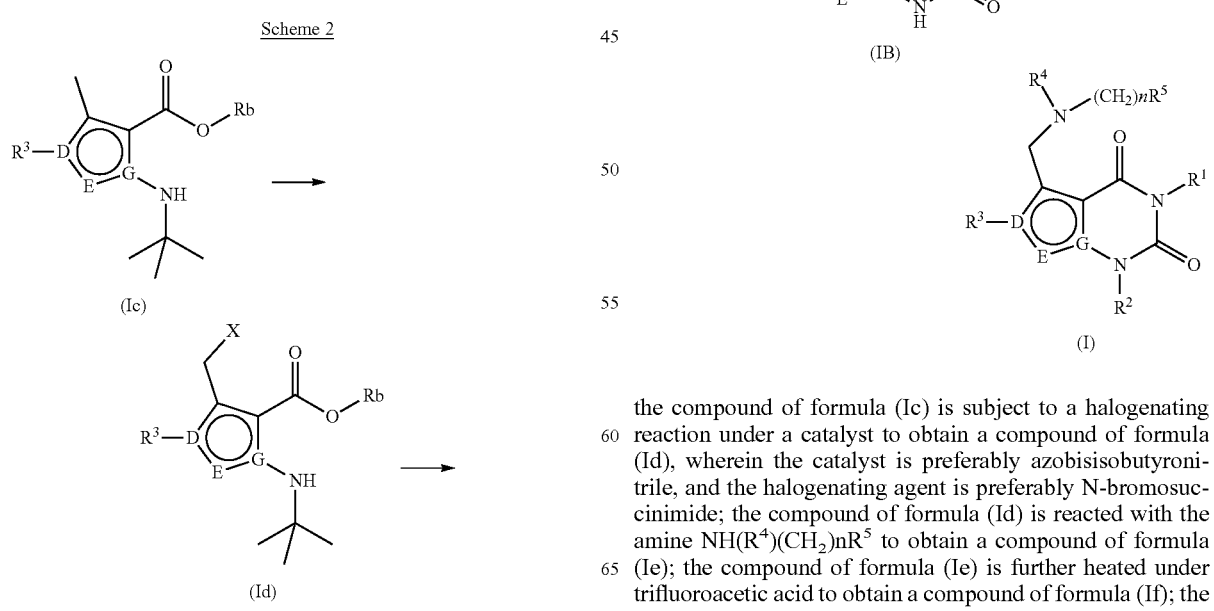

the compound of formula (Ic) is subject to a halogenating reaction under a catalyst to obtain a compound of formula (Id), wherein the catalyst is preferably azobisisobutyronitrile, and the halogenating agent is preferably N-bromosuccinimide; the compound of formula (Id) is reacted with the amine NH(R⁴)(CH₂)nR⁵ to obtain a compound of formula (Ie); the compound of formula (Ie) is further heated under trifluoroacetic acid to obtain a compound of formula (If); the compound of formula (If) is reacted with triphosgene and an amine of R¹NH₂ successively to obtain a compound of formula (Ig); the compound of formula (Ig) is subject to a cyclization reaction under an alkaline condition to obtain a compound of formula (IB); the compound of formula (IB) is reacted with R²X in the presence of an alkaline reagent to obtain a compound of formula (I);

wherein:

X is halogen; $R^b$ is alkyl;

n, D, E, G, and R¹ to R⁵ are as defined in formula (I); and

R³ is preferably an aryl, more preferably a phenyl, wherein the aryl is optionally further substituted with one or more groups selected from the group consisting of —NHC(O)NHR⁶ and —NHC(O)NHOR⁶.

A process for preparing a compound of formula (II), or a tautomer, mesomer, racemate, enantiomer, or diastereomer thereof, or mixture thereof, or a pharmaceutically acceptable salt thereof, comprises the following steps:

Scheme 3

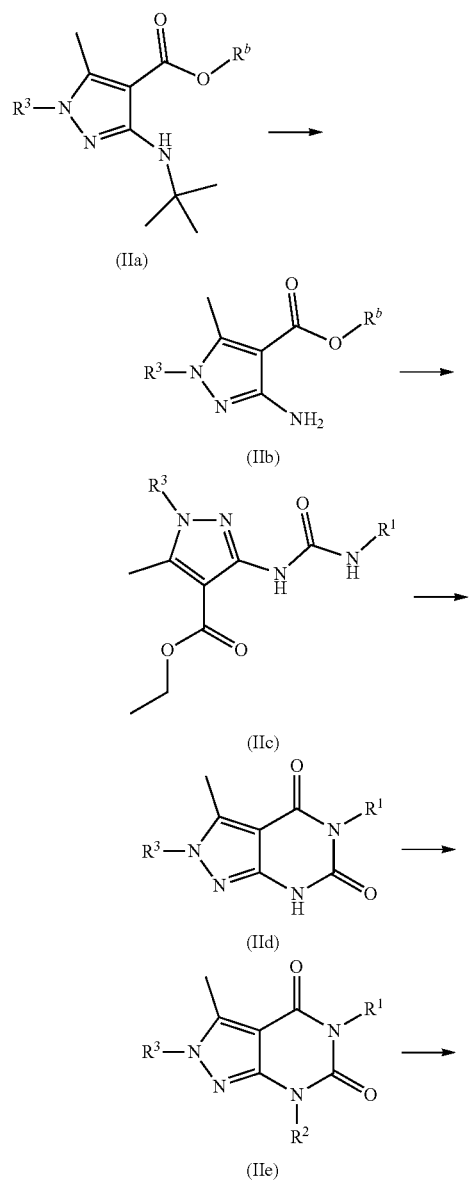

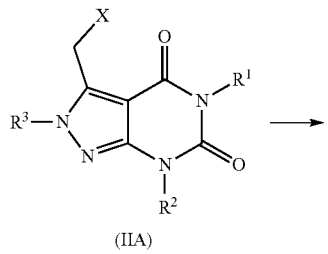

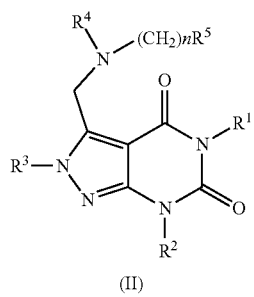

the compound of formula (IIa) is heated under trifluoroacetic acid to obtain a compound of formula (IIb); the compound of formula (IIb) is reacted with triphosgene and an amine of R¹NH₂ successively to obtain a compound of formula (IIc); the compound of formula (IIc) is subject to a cyclization reaction under an alkaline to obtain a compound of formula (IId); the compound of formula (IId) is reacted with R²X in the presence of an alkaline reagent to obtain a compound of formula (IIe); the compound of formula (IIe) is subject to a halogenating reaction under a catalyst to obtain a compound of formula (IIA), wherein the catalyst is preferably azobisisobutyronitrile, and the halogenating agent is preferably N-bromosuccinimide; the compound of formula (IIA) is reacted with an amine of NH(R⁴)(CH₂)nR⁵ to obtain a compound of formula (II);

wherein: X is halogen; $R^b$ is alkyl;

n, and R¹ to R⁵ are as defined in formula (I);

R³ is preferably an aryl, more preferably a phenyl, wherein the aryl is optionally further substituted with one or more groups selected from the group consisting of —NHC(O)NHR⁶ and —NHC(O)NHOR⁶.

A process for preparing a compound of formula (III), or a tautomer, mesomer, racemate, enantiomer, or diastereomer thereof, or mixture thereof, or a pharmaceutically acceptable salt thereof, comprises the following steps:

Scheme 4

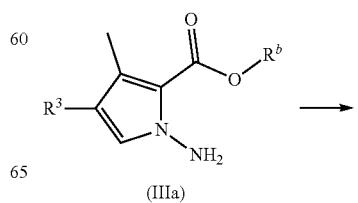

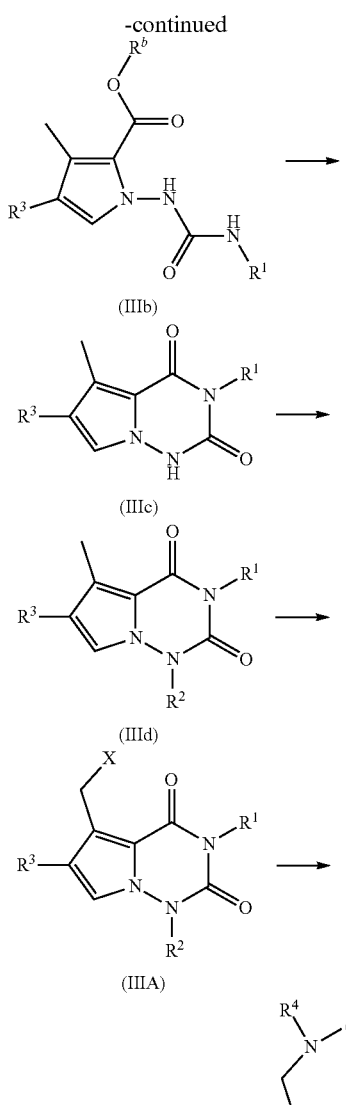
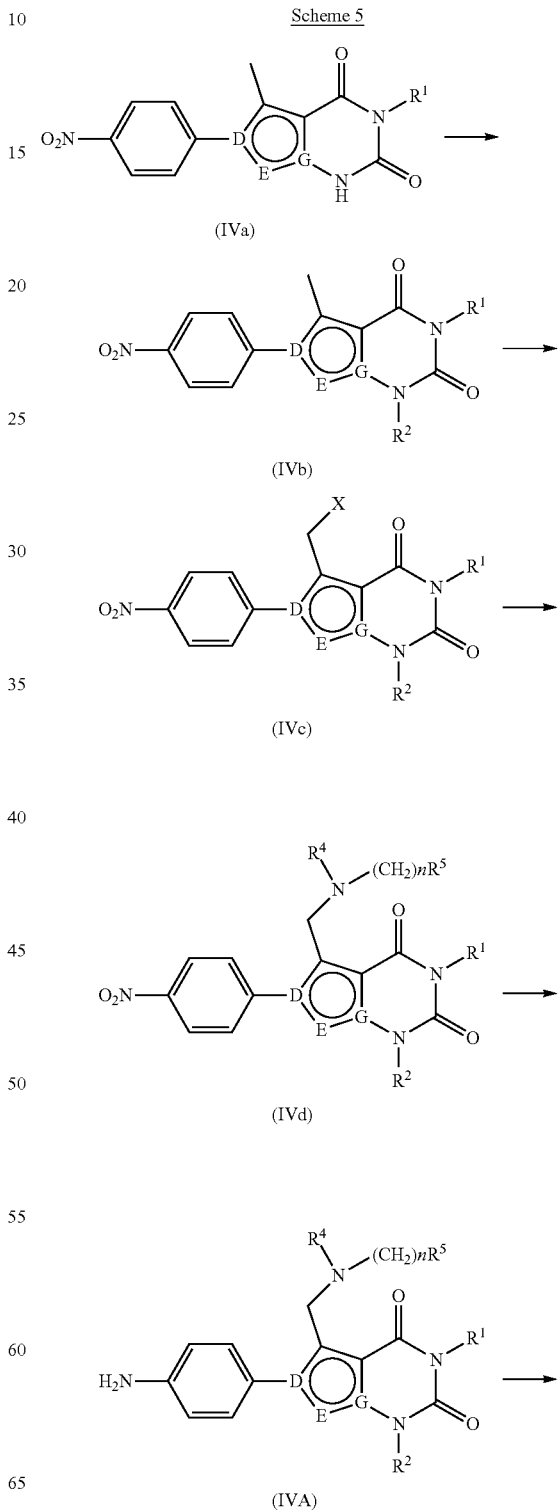

more groups selected from the group consisting of —NHC(O)NHR[6] and —NHC(O)NHOR[6].

A process for preparing a compound of formula (IV), or a tautomer, mesomer, racemate, enantiomer, or diastereomer thereof, or mixture thereof, or a pharmaceutically acceptable salt thereof, comprises the following steps:

Scheme 5 the compound of formula (IIIa) is reacted with triphosgene and an amine of $R^1NH_2$ successively to obtain a compound of formula (IIIb); the compound of formula (IIIb) is reacted under an alkaline condition to obtain a compound of formula (IIIc); the compound of formula (IIIc) is reacted with $R^2X$ in the presence of an alkaline reagent to obtain a compound of formula (IIId); the compound of formula (IIId) is subject to a halogenating reaction under a catalyst to obtain a compound of formula (IIIA), wherein the catalyst is preferably azobisisobutyronitrile, and the halogenating agent is preferably N-bromosuccinimide; the compound of formula (IIIA) is reacted with an amine of $NH(R^4)(CH_2)nR^5$ to obtain a compound of formula (III);

wherein: X is halogen; $R^b$ is alkyl;
n, and $R^1$ to $R^5$ are as defined in formula (I);
$R^3$ is preferably an aryl, more preferably a phenyl, wherein the aryl is optionally further substituted with one or -continued

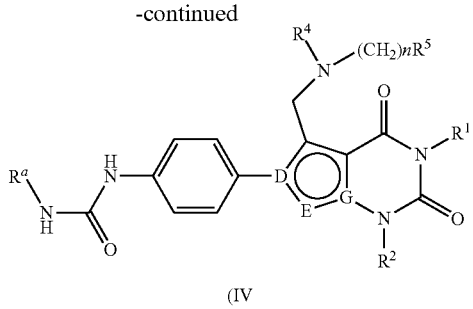

(IV)

formula (IVa) is prepared according to schemes 1-4; the compound of formula (IVa) is reacted with R²X in the presence of an alkaline reagent to obtain a compound of formula (IVb); the compound of formula (IVb) is subject to a halogenating reaction under a catalyst to obtain a compound of formula (IVc), wherein the catalyst is preferably azobisisobutyronitrile, and the halogenating agent is preferably N-bromosuccinimide; the compound of formula (IVc) is reacted with an amine of $NH(R^4)(CH_2)nR^5$ to obtain a compound of formula (IVd); the compound of formula (IVd) is subject to a reduction reaction with iron in the presence of ammonium chloride to reduce a nitro group to an amino group to obtain a compound of formula (IVA); the compound of formula (IVA) is further reacted with an acylating reagent to obtain a compound of formula (IV); wherein: X is halogen, and n, D, E, G, $R^a$, and $R^1$ to $R^5$ are as defined in formula (I).

In the aforesaid technical solutions, the alkaline condition is provided by an organic base or an inorganic base, wherein the organic base includes, but is not limited to, triethylamine, pyridine, 2,6-lutidine, sodium methoxide, lithium hexamethyldisilazide, sodium hexamethyldisilazide, n-butyllithium, potassium tert-butoxide or tetrabutyl ammonium bromide; and the inorganic base includes, but is not limited to, sodium hydride, sodium carbonate, sodium bicarbonate, potassium carbonate, potassium bicarbonate, cesium carbonate, lithium hydroxide, sodium hydroxide or potassium hydroxide. In the method of the present invention, the alkaline condition of cyclization is preferably an organic base, and more preferably is sodium methoxide.

Reducing agent includes, but is not limited to, hydrogen and iron powder.

Acylating agent includes, but is not limited to, carboxylic acid, acyl chloride, sulfuryl chloride, halogenated methyl formate, isocyanate, triphosgene, and methoxyamine.

The invention will be further illustrated with reference to the following specific examples. It should be understood that these examples are merely intended to demonstrate the invention without limiting the scope of the invention.

The experimental methods in the following examples for which no specific conditions are indicated will be carried out according to conventional conditions or recommended conditions of the raw materials and the product manufacturer. The experimental reagents for which no specific sources are indicated will be conventional reagents which are commercially available.

EXAMPLES

Compound structures are identified by nuclear magnetic resonance (NMR) and/or mass spectrometry (MS). NMR chemical shift (δ) is given in $10^{-6}$ (ppm). NMR is determined by Bruker AVANCE-400. The solvents for NMR are deuterated-dimethyl sulfoxide (DMSO-$d_6$), deuterated-chloroform (CDCl$_3$) and deuterated-methanol (CD$_3$OD), with tetramethylsilane (TMS) as an internal standard.

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ are determined by a NovoStar ELISA (BMG Co., Germany).

Yantai Huanghai HSGF254 or Qingdao GF254 silica gel plate is used for thin-layer silica gel chromatography (TLC). The dimension of the plates used in TLC was 0.15 mm to 0.2 mm, and the dimension of the plates used in product purification is 0.4 mm to 0.5 mm.

Yantai Huanghai 200 to 300 mesh silica gel is used as carrier in column chromatography.

The known starting materials of the present invention can be prepared by conventional synthesis methods in the art, or can be purchased from ABCR GmbH & Co. KG, Acros Organics, Aldrich Chemical Company, Accela ChemBio Inc., or Dari Chemical Company, etc.

Unless otherwise stated, the reactions can be carried out under nitrogen atmosphere or argon atmosphere.

The term "argon atmosphere" or "nitrogen atmosphere" means that a reaction flask is equipped with a 1 L argon or nitrogen balloon.

Unless otherwise stated, the solution in the examples refers to an aqueous solution.

Unless otherwise stated, the reaction temperature in the examples is room temperature, and the range of the room temperature was 20° C. to 30° C.

The reaction process is monitored by thin layer chromatography (TLC), and the system of developing solvent includes: A: dichloromethane and methanol system, B: n-hexane and ethyl acetate system, C: petroleum ether and ethyl acetate system, D: acetone. The ratio of the solvent can be adjusted according to the polarity of the compounds.

The elution system for purification of the compounds by column chromatography and thin layer chromatography includes: A: dichloromethane and methanol system, B: n-hexane and ethyl acetate system, C: dichloromethane and acetone system, D: ethyl acetate and dichloromethane system, E: ethyl acetate and dichloromethane and n-hexane system, F: ethyl acetate and dichloromethane and acetone system. The volume ratio of the solvent can be adjusted according to the polarity of the compounds, and sometimes a little alkaline reagent, such as triethylamine, or acidic reagent, such as acetic acid, may also be added.

Example 1
N-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)acetamide
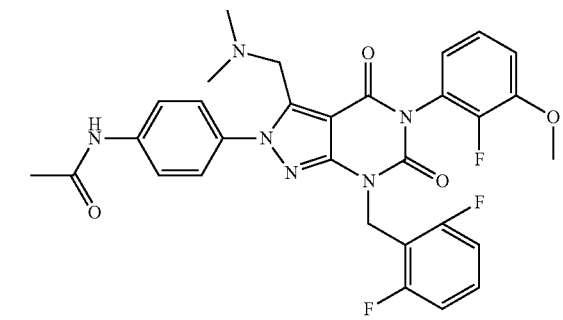
1a
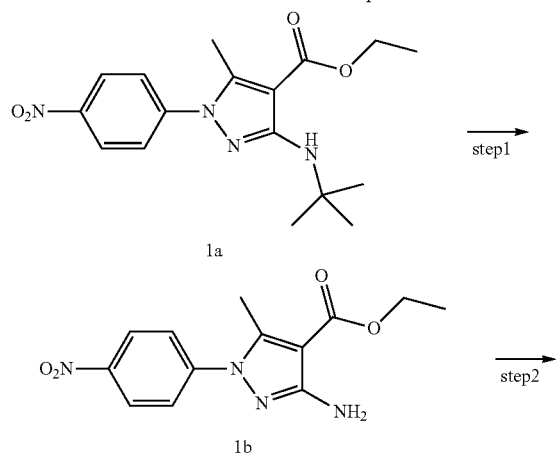
1b → step2
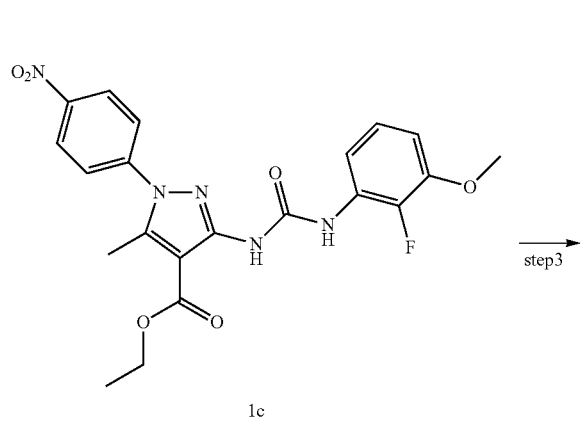
1c → step3
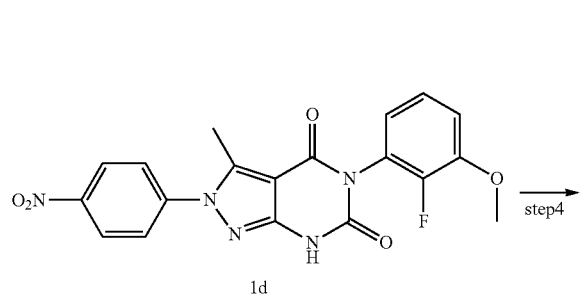
1d → step4
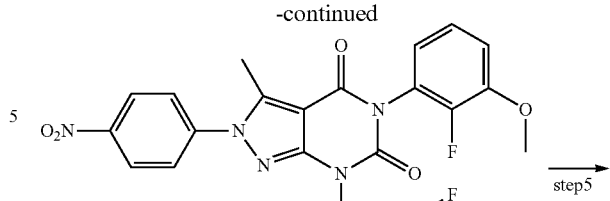
1e → step5
1f → step6
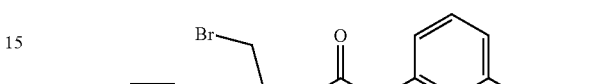
1g → step7
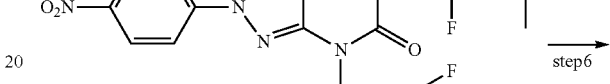
1h → step8
1

Step 1

Ethyl 3-amino-5-methyl-1-(4-nitrophenyl)-1H-pyrazole-4-carboxylate

Ethyl 3-(tert-butylamino)-5-methyl-1-(4-nitrophenyl)-1H-pyrazole-4-carboxylate 1a (12.10 g, 34.93 mmol, prepared by a well known method disclosed in "Synthesis, 1988, (3), 203-207") and 100 mL of trifluoroacetic acid were added to a 250 mL of eggplant shaped flask successively. The mixture was stirred for 2.5 hours at 85° C., and then the reaction was stopped. The reaction solution was cooled to room temperature, and concentrated under reduced pressure. The residue was added dropwise with saturated sodium bicarbonate solution to adjust the pH>7, and filtrated. The filter cake was dissolved in dichloromethane and the organic phase was dried over anhydrous sodium sulfate, and filtered. The filtrate was concentrated under reduced pressure and the residue was slurried with 50 mL of a mixture of dichloromethane and methanol (V/V=20:1), and filtered. The product was dried to obtain 5.30 g of yellow solid. The mother solution was concentrated under reduced pressure and the residue was purified by silica gel column chromatography with elution system A to obtain the title compound ethyl 3-amino-5-methyl-1-(4-nitrophenyl)-1H-pyrazole-4-carboxylate 1b (total product 6.07 g, yellow solid), yield: 60.1%.

MS m/z (ESI): 291.2 [M+1]

Step 2

Ethyl 3-(3-(2-fluoro-3-methoxyphenyl)ureido)-5-methyl-1-(4-nitrophenyl)-1H-pyrazole-4-carboxylate Ethyl 3-amino-5-methyl-1-(4-nitrophenyl)-1H-pyrazole-4-carboxylate 1b (550 mg, 1.89 mmol) was dissolved in 50 mL of dichloromethane. The mixture, which was insufficiently soluble at room temperature, was added with triethylamine (0.66 mL, 4.75 mmol) and triphosgene (225 mg, 0.76 mmol), and stirred until it was dissolved completely. After stirring for 30 minutes, the reaction solution was added with 2-fluoro-3-methoxyaniline (283 mg, 2 mmol) and stirred for 12 hours at room temperature, then the reaction was stopped. The reaction solution was concentrated under reduced pressure, and the residues was added with 20 mL of water, and extracted with dichloromethane (50 mL×2). The organic phases were combined, dried over anhydrous sodium sulfate, and filtered. The filtrate was concentrated under reduced pressure and the residue was purified by silica gel column chromatography with elution system A to obtain the title compound ethyl 3-(3-(2-fluoro-3-methoxyphenyl)ureido)-5-methyl-1-(4-nitrophenyl)-1H-pyrazole-4-carboxylate 1c (640 mg, white solid), yield: 73.9%.

MS m/z (ESI): 458.1 [M+1]

Step 3

5-(2-fluoro-3-methoxyphenyl)-3-methyl-2-(4-nitrophenyl)-2H-pyrazolo[3,4-d]pyrimidine-4,6(5H,7H)-dione Ethyl 3-(3-(2-fluoro-3-methoxyphenyl)ureido)-5-methyl-1-(4-nitrophenyl)-1H-pyrazole-4-carboxylate 1c (640 mg, 1.40 mmol) was dissolved in 30 mL of ethanol, and then added with sodium methoxide (190 mg, 3.52 mmol). After reacting for 3 hours at room temperature, the reaction solution was heated to 80° C. and further reacted for 1 hour. Then, the reaction was stopped. The reaction solution was cooled to room temperature, and then added with 3.5 mL of 1 M hydrochloric acid solution, and filtered. The filter cake was washed with water (20 mL×1), ethanol (10 mL×1), and methyl tert-butyl ether (5 mL×1) successively, and dried to obtain the title compound 5-(2-fluoro-3-methoxyphenyl)-3-methyl-2-(4-nitrophenyl)-2H-pyrazolo[3,4-d]pyrimidine-4,6(5H,7H)-dione 1d (536 mg, light yellow solid), yield: 93.2%.

MS m/z (ESI): 412.2 [M+1]

Step 4

7-(2,6-difluorobenzyl)-5-(2-fluoro-3-methoxyphenyl)-3-methyl-2-(4-nitrophenyl)-2H-pyrazolo[3,4-d]pyrimidine-4,6(5H,7H)-dione 5-(2-fluoro-3-methoxyphenyl)-3-methyl-2-(4-nitrophenyl)-2H-pyrazolo[3,4-d]pyrimidine-4,6(5H,7H)-dione 1d (530 mg, 1.29 mmol), 2-(chloromethyl)-1,3-difluorobenzene (230 mg, 1.41 mmol), potassium iodide (235 mg, 1.41 mmol), and potassium carbonate (196 mg, 1.42 mmol) were dissolved in 15 mL of N,N-dimethyl formamide, successively. After reacting for 24 hours at room temperature, the reaction was stopped, and the reaction solution was concentrated under reduced pressure. The residue was added with 30 mL of water and 20 mL of methyl tert-butyl ether under stirring, and then filtered. The filter cake was dissolved in 50 mL of dichloromethane, dried over anhydrous sodium sulfate, and filtered. The filtrate was concentrated under reduced pressure to obtain 570 mg of solid. The mother solution was extracted, the organic phase was washed with water (20 mL×3), and saturated sodium chloride solution (20 mL×1), successively, dried over anhydrous sodium sulfate, and filtered. The filtrate was concentrated under reduced pressure and the residue was slurried with 15 mL of a mixture of n-hexane and methyl tert-butyl ether (V/V=1:1), and filtered. The filter cake was dried to obtain 110 mg of solid. The title compound 7-(2,6-difluorobenzyl)-5-(2-fluoro-3-methoxyphenyl)-3-methyl-2-(4-nitrophenyl)-2H-pyrazolo[3,4-d]pyrimidine-4,6(5H,7H)-dione 1e (total product 680 mg, tan solid) was obtained, yield: 98.3%.

MS m/z (ESI): 538.2 [M+1]

Step 5

3-(bromomethyl)-7-(2,6-difluorobenzyl)-5-(2-fluoro-3-methoxyphenyl)-2-(4-nitrophenyl)-2H-pyrazolo[3,4-d]pyrimidine-4,6(5H,7H)-dione Under argon atmosphere, 7-(2,6-difluorobenzyl)-5-(2-fluoro-3-methoxyphenyl)-3-methyl-2-(4-nitrophenyl)-2H-pyrazolo[3,4-d]pyrimidine-4,6(5H,7H)-dione 1e (660 mg, 1.23 mmol), azobisisobutyronitrile (24 mg, 0.15 mmol), and N-bromosuccinimide (262 mg, 1.47 mmol) were dissolved in 20 mL of chlorobenzene, successively. After reacting for 12 hours at 85° C., the reaction was stopped and the reaction solution was cooled to room temperature, and then washed with saturated sodium chloride solution (15 mL×1) and saturated sodium thiosulfate solution (15 mL×1), successively. The aqueous phase was extracted with dichloromethane (40 mL×2). The organic phases were combined, dried over anhydrous sodium sulfate, and filtered. The filtrate was concentrated under reduced pressure to obtain the crude title compound 3-(bromomethyl)-7-(2,6-difluorobenzyl)-5-(2-fluoro-3-methoxyphenyl)-2-(4-nitrophenyl)-2H-pyrazolo[3, 4-d]pyrimidine-4,6(5H,7H)-dione 1f (900 mg, light yellow solid), which was used directly in the next step.

MS m/z (ESI): 616.1 [M+1]

Step 6

7-(2,6-difluorobenzyl)-3-((dimethylamino)methyl)-5-(2-fluoro-3-methoxyphenyl)-2-(4-nitrophenyl)-2H-pyrazolo[3,4-d]pyrimidine-4,6(5H,7H)-dione The crude 3-(bromomethyl)-7-(2,6-difluorobenzyl)-5-(2-fluoro-3-methoxyphenyl)-2-(4-nitrophenyl)-2H-pyrazolo[3,4-d]pyrimidine-4,6(5H,7H)-dione 1f (900 mg, 1.46 mmol) was dissolved in a 3 mL solution of dimethylamine in tetrahydrofuran. After reacting for 12 hours at room temperature, the reaction was stopped and the reaction solution was concentrated under reduced pressure. The residue was purified via silica gel column chromatography with eluent system D to obtain 627 mg of crude compound. The crude compound was purified by thin-layer chromatography with eluent system E to obtain the title compound 7-(2,6-difluorobenzyl)-3-((dimethylamino)methyl)-5-(2-fluoro-3-methoxyphenyl)-2-(4-nitrophenyl)-2H-pyrazolo[3,4-d]pyrimidine-4,6(5H,7H)-dione 1g (223 mg, light yellow solid), yield: 31.0%.

MS m/z (ESI): 581.3 [M+1]

Step 7

2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 7-(2,6-difluorobenzyl)-3-((dimethylamino)methyl)-5-(2-fluoro-3-methoxyphenyl)-2-(4-nitrophenyl)-2H-pyrazolo[3,4-d]pyrimidine-4,6(5H,7H)-dione 1g (212 mg, 0.36 mmol) was dissolved in 8 mL of formic acid, and then added with a 0.25 mL solution of 4 M HCl in 1, 4-dioxane and 10% palladium on carbon (40 mg). The mixture was purged with hydrogen three times and reacted for 2 hours under hydrogen atmosphere and normal pressure. Then the reaction was stopped, and the reaction mixture was filtered. The filter cake was washed with methanol (20 mL×2). The organic phase was concentrated under reduced pressure. The residue was added with 50 mL of dichloromethane and 15 mL of saturated sodium bicarbonate solution, and stirred for 10 minutes. The saturated sodium bicarbonate solution was added dropwise to adjust the pH>7, and the aqueous phase was subject to extraction. The aqueous phase was extracted with dichloromethane (20 mL×3). The organic phases were combined, dried over anhydrous sodium sulfate, and filtered. The filtrate was concentrated under reduced pressure, and the residue was purified by thin-layer chromatography with eluent system A to obtain the title compound 2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 1h (180 mg, white solid), yield: 89.5%.

MS m/z (ESI): 551.3 [M+1]

Step 8

N-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)acetamide 2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 1h (33 mg, 0.059 mmol) was dissolved in 5 mL of dichloromethane, and added with triethylamine (13 µL, 0.094 mmol) and acetic anhydride (7 µL, 0.072 mmol). After reacting for 12 hours at room temperature, the reaction was incomplete. 5 µL of acetic anhydride was then supplemented, and the mixture was heated to 35° C. and further reacted for 2 hours. The reaction was stopped and the reaction solution was added with 2 mL of saturated sodium bicarbonate solution, stirred for 10 minutes, and extracted. The aqueous phase was extracted with dichloromethane (15 mL×3). The organic phases were combined, dried over anhydrous sodium sulfate, and filtered. The filtrate was concentrated under reduced pressure, and the residue was purified by thin layer chromatography with elution system A to obtain the title compound N-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)acetamide 1 (25 mg, white solid), yield: 71.4%.

MS m/z (ESI): 593.1 [M+1]

$^1$H NMR (400 MHz, CDCl$_3$) δ 7.89 (d, 2H), 7.67 (d, 2H), 7.36 (s, 1H), 7.25-7.30 (m, 1H), 7.19 (t, 1H), 7.08 (t, 1H), 7.89-7.94 (m, 3H), 5.45 (s, 2H), 3.93 (s, 3H), 3.69-3.70 (m, 2H), 2.35 (s, 6H), 2.25 (s, 3H).

Example 2

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methoxyurea

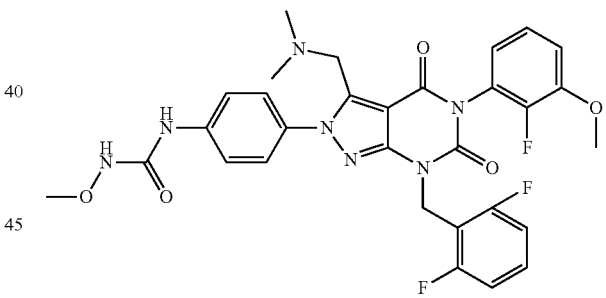

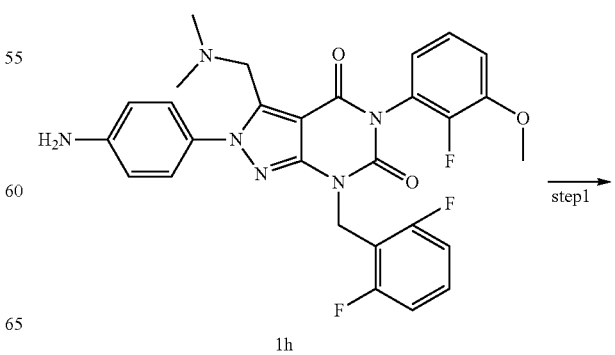

1h

-continued

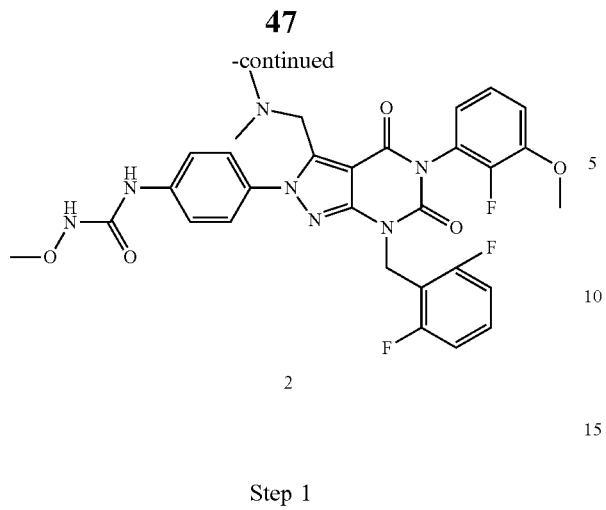

2

Step 1

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methoxy urea 2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 1h (30 mg, 0.054 mmol) was dissolved in 5 mL of dichloromethane, and added with triethylamine (0.045 mL, 0.32 mmol) and triphosgene (6.5 mg, 0.022 mmol). After reacting for 1 hour, the reaction solution was added with methoxyamine (6.8 mg, 0.081 mmol), and further reacted for 12 hours at room temperature, and then supplemented with triphosgene (18 mg, 0.061 mmol), and further reacted for 1 hour at 35° C., followed by addition of methoxyamine (100 mg, 1.20 mmol) and continued reaction for 2 hours at 35° C. The reaction was stopped, and the reaction solution was added with 10 mL of saturated sodium bicarbonate solution, and extracted. The aqueous phase was extracted with dichloromethane (15 mL×3). The organic phases were combined, dried over anhydrous sodium sulfate, and filtered. The filtrate was concentrated under reduced pressure and the residue was purified by thin layer chromatography with elution system A to obtain the title compound 1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methoxyurea 2 (12 mg, pale yellow solid), yield: 35.3%.

MS m/z (ESI): 624.5 [M+1]

$^1$H NMR (400 MHz, CDCl$_3$) δ 7.90 (d, 2H), 7.71 (s, 1H), 7.67 (d, 2H), 7.20-7.30 (m, 3H), 7.06-7.08 (m, 1H), 6.89-6.94 (m, 3H), 5.45 (s, 2H), 3.94 (s, 3H), 3.87 (s, 3H), 3.86 (s, 2H), 2.35 (s, 6H).

Example 3

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-ethylurea

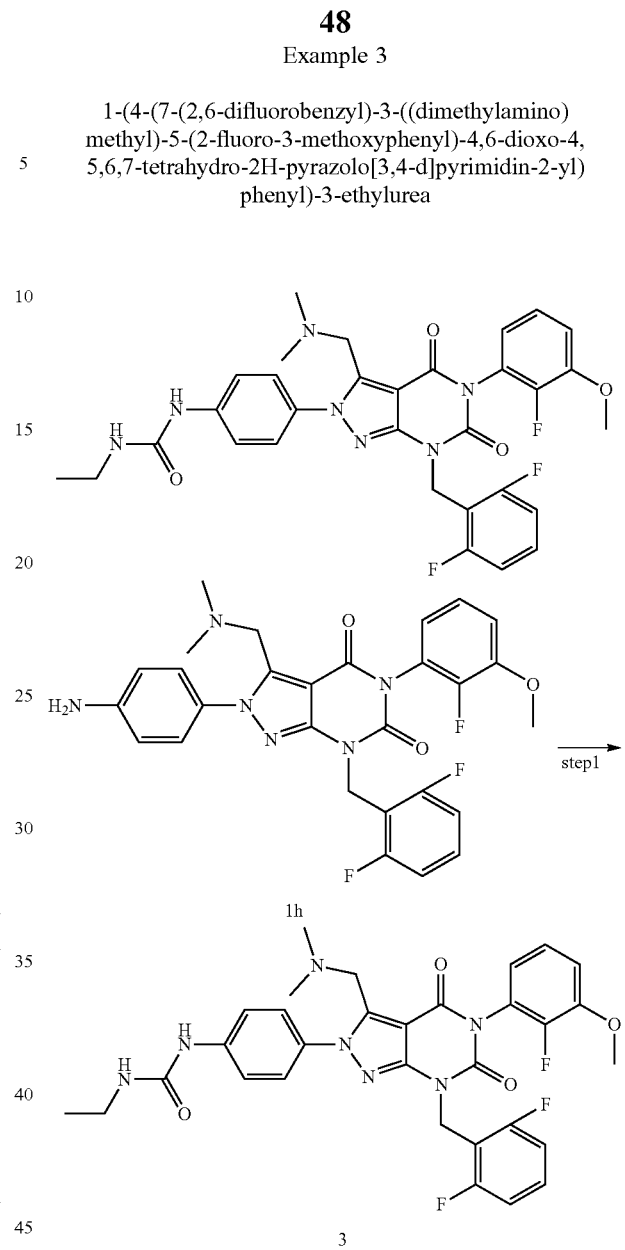

Step 1

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-ethylurea 2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 1h (26 mg, 0.047 mmol) was dissolved in 3 mL of tetrahydrofuran, added with ethyl isocyanate (55 μL, 0.69 mmol), and reacted for 12 hours at 35° C. The reaction was stopped, and the reaction solution was concentrated under reduced pressure. The residue was added with 10 mL of water and 20 mL of dichloromethane, and extracted. The aqueous phase was extracted with dichloromethane (15 mL×3). The organic phases were combined, dried over anhydrous sodium sulfate, and filtered. The filtrate was concentrated under reduced pressure and the residue was purified by thin layer chromatography with elution system A to obtain the title compound 1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-ethylurea 3 (12 mg, white solid), yield: 41.4%.

MS m/z (ESI): 622.5 [M+1]

$^1$H NMR (400 MHz, CDCl$_3$) δ 7.80 (d, 2H), 7.45 (d, 2H), 7.22-7.26 (m, 2H), 7.13-7.15 (m, 1H), 6.99-7.04 (m, 1H), 6.84-6.89 (m, 3H), 6.45 (s, 1H), 5.40 (s, 2H), 3.89 (s, 3H), 3.65 (s, 2H), 3.33-3.35 (m, 2H), 2.30 (s, 6H), 1.20 (t, 3H).

Example 4

Methyl (4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)carbamate

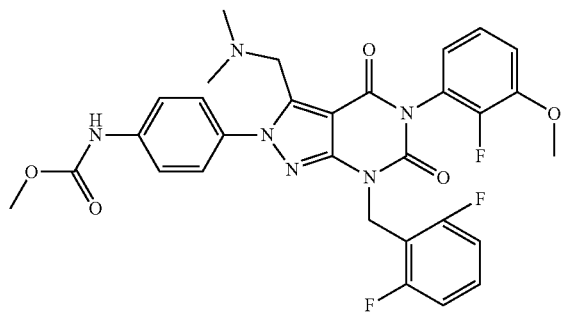

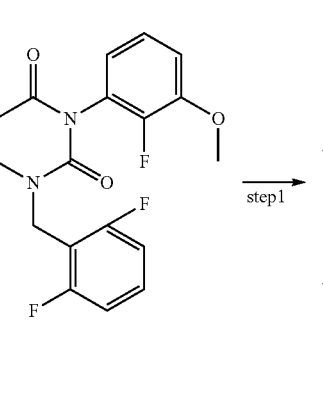

1h

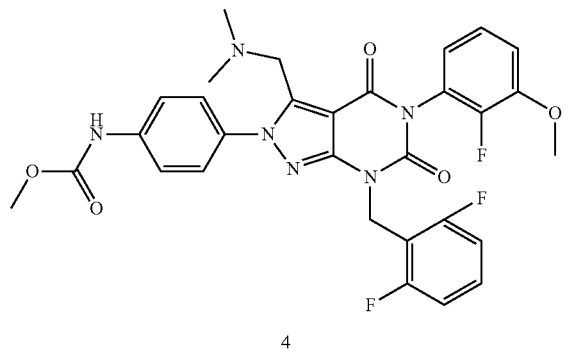

4

Step 1

Methyl (4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)carbamate 2-(4-aminophenyl)-7-(2,6-difluorobenzyl)-3-((dimethylamino)methyl)-5-(2-fluoro-3-methoxyphenyl)-2H-pyrazolo[3,4-d]pyrimidine-4,6(5H,7H)-dione 1h (35 mg, 0.064 mmol) was dissolved in 5 mL of dichloromethane, and added with triethylamine (0.8 mL, 5.8 mmol) and methyl chloroformate (0.5 mL, 4.14 mmol). After reacting for 12 hours at 35° C., the reaction was stopped and cooled to room temperature. The reaction solution was added with 10 mL of saturated sodium bicarbonate solution, and extracted. The aqueous phase was extracted with dichloromethane (15 mL×3). The organic phases were combined, dried over anhydrous sodium sulfate, and filtered. The filtrate was concentrated under reduced pressure, and the residue was purified by thin layer chromatography with elution system A to obtain the title compound methyl (4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)carbamate 4 (24 mg, white solid), yield: 61.5%.

MS m/z (ESI): 609.5 [M+1]

$^1$H NMR (400 MHz, CDCl$_3$) δ 7.88 (d, 2H), 7.55 (d, 2H), 7.25-7.27 (m, 1H), 7.18-7.20 (m, 1H), 7.06-7.08 (m, 1H), 6.88-6.94 (m, 3H), 6.78 (s, 1H), 5.45 (s, 2H), 3.93 (s, 3H), 3.85 (s, 3H), 3.65-3.73 (m, 2H), 2.35 (s, 6H).

Example 5

1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methylurea

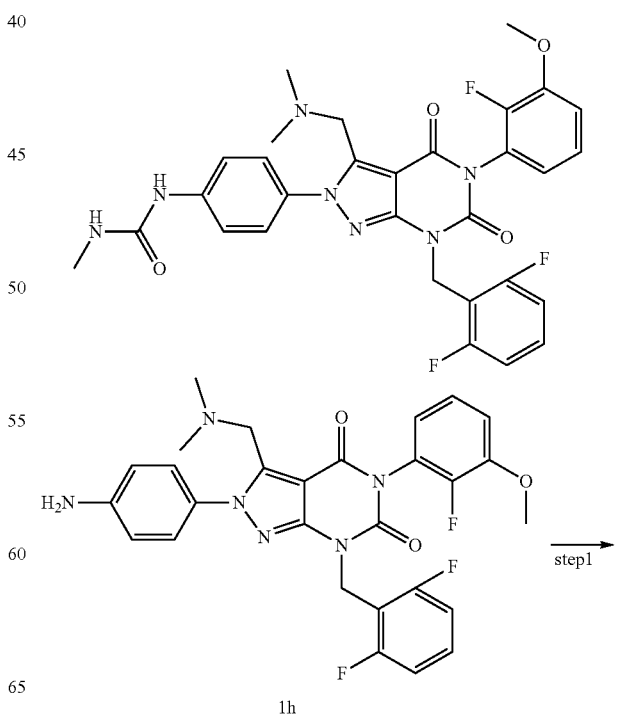

1h

51
-continued

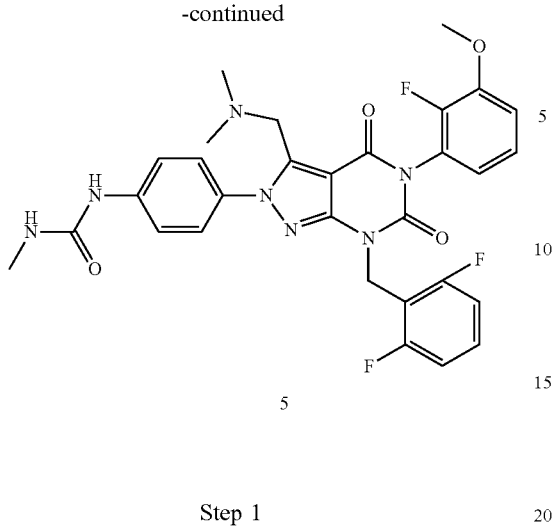

5

Step 1

1-(4-(7-(2,6-difluorobenzyl)-3-((dimethylamino)
methyl)-5-(2-fluoro-3-methoxyphenyl)-4,6-dioxo-4,
5,6,7-tetrahydro-2H-pyrazolo[3,4-d]pyrimidin-2-yl)
phenyl)-3-methylurea Acetic acid (46 mg, 0.77 mmol) was dissolved in 1 mL of toluene and added with N,N-diisopropylethylamine (0.2 mL, 1.13 mmol) and diphenylphosphoryl azide (0.16 mL, 0.73 mmol). The mixture was stirred for 1 hour at 70° C., and then cooled in an ice bath, followed by addition of 2-(4-aminophenyl)-7-(2,6-difluorobenzyl)-3-((dimethylamino) methyl)-5-(2-fluoro-3-methoxyphenyl)-2H-pyrazolo[3,4-d] pyrimidine-4,6(5H,7H)-dione 1h (30 mg, 0.050 mmol) and 2 mL dichloromethane in an ice bath. The mixture was reacted for 12 hours at room temperature. The reaction was stopped, and the reaction solution was added with 10 mL of saturated sodium bicarbonate solution, and extracted with dichloromethane (25 mL×1). The organic phase was washed with water (10 mL×1) and saturated sodium chloride solution (10 mL×1), dried over anhydrous sodium sulfate, and filtered. The filtrate was concentrated under reduced pressure, and the residues were purified by thin layer chromatography with elution system A to obtain the title compound 1-(4-(7-(2,6-difluorobenzyl)-3-((dimethylamino)methyl)-5-(2-fluoro-3-methoxyphenyl)-4,6-dioxo-4,5,6,7-tetrahydro-2H-pyrazolo[3,4-d]pyrimidin-2-yl)phenyl)-3-methylurea 5 (8 mg, white solid), yield: 24.4%.

MS m/z (ESI): 607.9 [M+1]

$^1$H NMR (400 MHz, CDCl$_3$) δ 7.79 (d, 2H), 7.50 (d, 2H), 7.27-7.30 (m, 1H), 7.19 (t, 1H), 7.06 (t, 1H), 6.880-6.93 (m, 4H), 5.44 (s, 2H), 4.95 (s, 1H), 3.92 (s, 3H), 3.78 (s, 2H), 2.88 (d, 3H), 2.39 (s, 6H).

52
Example 6

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-ethylurea

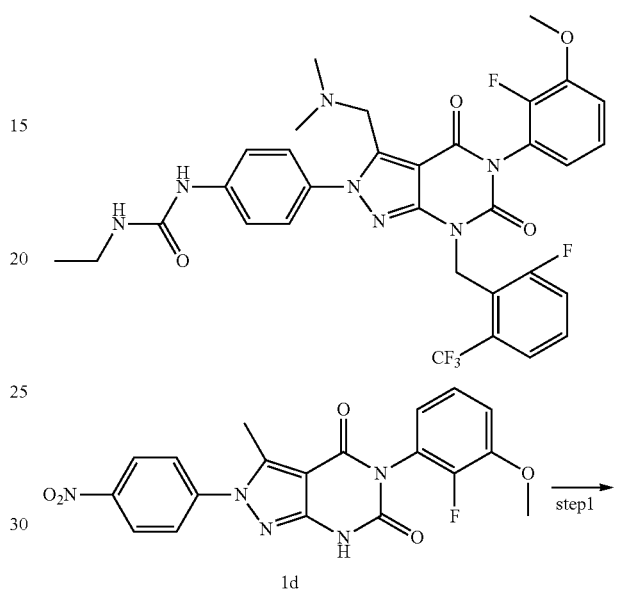

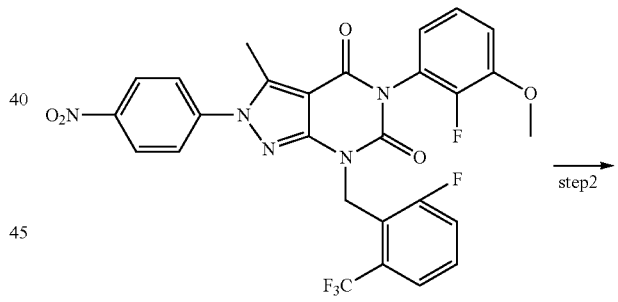

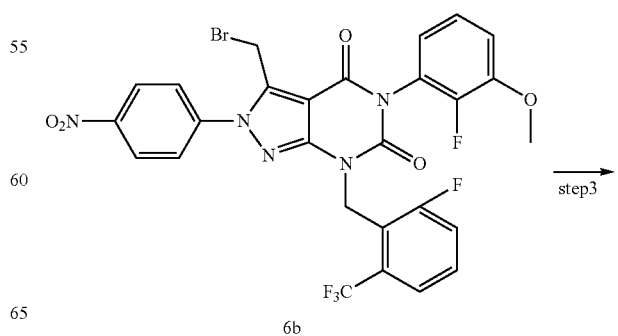

-continued

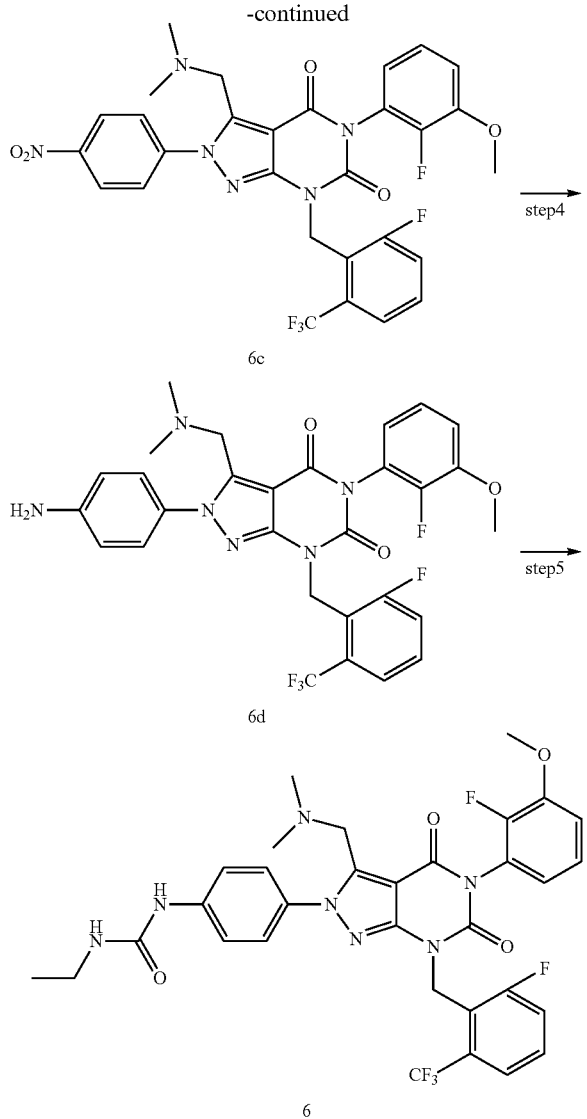

Step 1

5-(2-fluoro-3-methoxyphenyl)-7-(2-fluoro-6-(trifluoromethyl)benzyl)-3-methyl-2-(4-nitrophenyl)-2H-pyrazolo[3,4-d]pyrimidine-4,6(5H,7H)-dione 5-(2-fluoro-3-methoxyphenyl)-3-methyl-2-(4-nitrophenyl)-2H-pyrazolo[3,4-d]pyrimidine-4,6(5H,7H)-dione 1d (1.90 g, 4.62 mmol), 2-(bromomethyl)-1-fluoro-3-(trifluoromethyl)benzene (1.31 g, 5.10 mmol), potassium iodide (844 mg, 5.08 mmol), and potassium carbonate (702 mg, 5.09 mmol) were dissolved in 54 mL of N,N-dimethylformamide successively. After stirring for 20 hours at room temperature, the reaction was stopped, and the reaction solution was concentrated under reduced pressure. The residues were added with water and ether to slurry for 1 hour, and filtered. The filter cake was washed with ether (10 mL×3) and dried to obtain the title compound 5-(2-fluoro-3-methoxyphenyl)-7-(2-fluoro-6-(trifluoromethyl)benzyl)-3-methyl-2-(4-nitrophenyl)-2H-pyrazolo[3,4-d]pyrimidine-4,6(5H,7H)-dione 6a (1.91 g, white solid), yield: 70.7%.
MS m/z (ESI): 588.1 [M+1]

Step 2

3-(bromomethyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione 5-(2-fluoro-3-methoxyphenyl)-7-(2-fluoro-6-(trifluoromethyl)benzyl)-3-methyl-2-(4-nitrophenyl)-2H-pyrazolo[3,4-d]pyrimidine-4,6(5H,7H)-dione 6a (1.81 g, 3.08 mmol), azobisisobutyronitrile (61 mg, 0.37 mmol) and N-bromosuccinimide (660 mg, 3.71 mmol) were dissolved in 53 mL of chlorobenzene. The resulting solution was purged with argon three times, and reacted for 19 hours at 85° C. under argon atmosphere. The reaction was stopped, and the reaction solution was washed with saturated sodium thiosulfate solution (30 mL×1) and saturated sodium chloride solution (50 mL×2), dried over anhydrous sodium sulfate, and filtered. The filtrate was concentrated under reduced pressure to obtain the crude title compound 3-(bromomethyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione 6b (2.18 g, pale yellow solid), which was used directly in the next step.
MS m/z (ESI): 666.0 [M+1]

Step 3

3-((dimethylamino)methyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione The crude 3-(bromomethyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione 6b (2.18 g, 3.27 mmol) and dimethylamine (2 M solution in THF) (6.8 mL 13.6 mmol) were added to the reaction flask and stirred for 12 hours at room temperature. The reaction was stopped, and the reaction solution was concentrated under reduced pressure. The residue was purified by preparative separation to obtain the title compound 3-((dimethylamino)methyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione 6c (455 mg, white solid), yield: 22.1%.
MS m/z (ESI): 630.8 [M+1]

Step 4

2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione 3-((dimethylamino)methyl)-5-(2-fluoro-3-methoxyphenyl)-7-(2-fluoro-6-(trifluoromethyl)benzyl)-2-(4-nitrophenyl)-2H-pyrazolo[3,4-d]pyrimidine-4,6(5H,7H)-dione 6c (200 mg, 0.32 mmol) was dissolved in 8 mL of formic acid, and added with 0.25 mL solution of 4 M HCl in 1,4-dioxane and 10% of Pd/C (50 mg). The mixture was purged with hydrogen three times, and stirred for 2 hours at room temperature. The reaction was stopped and filtered. The filter cake was washed with a small amount of methanol. The filtrate was concentrated under reduced pressure, added with 50 mL of dichloromethane and 20 mL of sodium bicarbonate solution, and stirred for 10 minutes. The aqueous phase was adjusted to pH 8, and extracted. The aqueous phase was extracted with dichloromethane (25 mL×2) and the organic phases were combined, dried over anhydrous sodium sulfate, and filtered. The filtrate was concentrated under reduced pressure and the residue was purified by thin layer chromatography with elution system A to obtain the title compound 2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione 6d (135 mg, white solid), yield: 71.1%.

MS m/z (ESI): 600.9 [M+1]

Step 5

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-ethylurea 2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione 6d (30 mg, 0.050 mmol) was dissolved in 1 mL of dichloromethane, and added with ethyl isocyanate (0.06 mL, 0.76 mmol). After reacting for 12 hours at 35° C., the reaction was stopped and the reaction solution was added with 5 mL of saturated sodium bicarbonate solution and 20 mL of dichloromethane solution, and subjected to extraction. The organic phase was washed with water (10 mL×1) and saturated sodium chloride solution (5 mL×1), dried over anhydrous sodium sulfate, and filtered, The filtrate was concentrated under reduced pressure, and the residue was purified by thin layer chromatography with elution system A to obtain the title compound 1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-ethylurea 6 (15 mg, white solid), yield: 44.1%.

MS m/z (ESI): 671.9 [M+1]

$^1$H NMR (400 MHz, CDCl$_3$) δ 7.75 (d, 2H), 7.51 (d, 1H), 7.46 (d, 2H), 7.37-7.40 (m, 1H), 7.18-7.24 (m, 2H), 7.15 (t, 1H), 6.91 (t, 1H), 6.85 (s, 1H), 5.60 (s, 2H), 4.92 (s, 1H), 3.90 (s, 3H), 3.69-3.76 (m, 2H), 3.28-3.35 (m, 2H), 2.35 (s, 6H), 1.19 (t, 3H).

Example 7

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methoxyurea

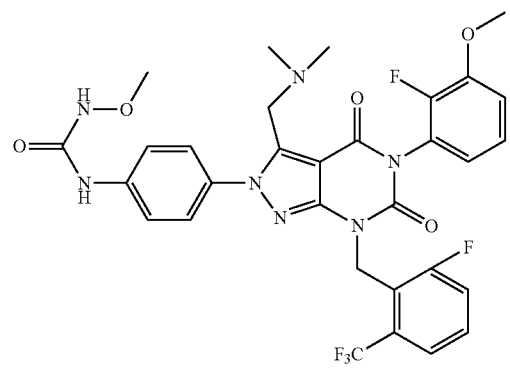

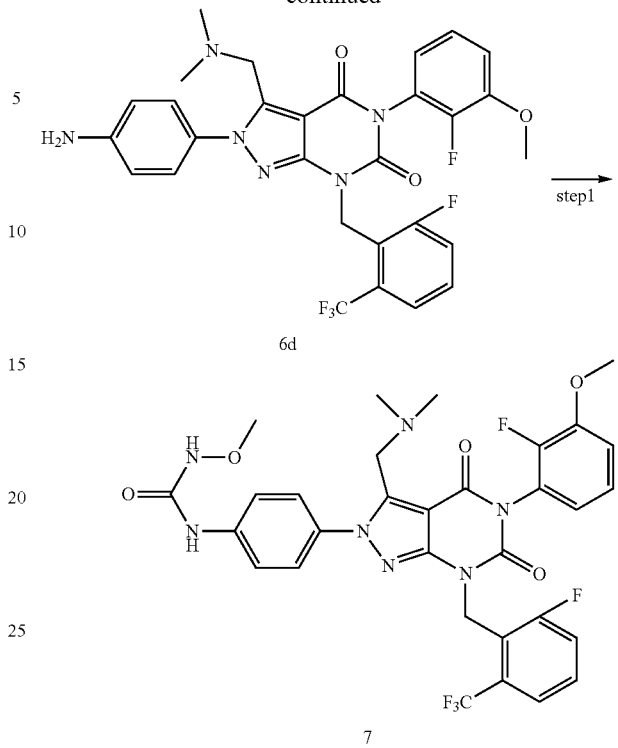

Step 1

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methoxyurea 2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione 6d (30 mg, 0.050 mmol) was dissolved in 3 mL of dichloromethane, and added with triethylamine (0.07 mL, 0.50 mmol) and triphosgene (15 mg, 0.051 mmol). After reacting for 1 hour at room temperature, the reaction was stopped and the reaction solution was added with 10 mL of water, and then extracted with dichloromethane (25 mL×1). The organic phase was washed with saturated sodium bicarbonate solution (10 mL×1), water (10 mL×1), and saturated sodium chloride solution (10 mL×1), successively, dried over anhydrous sodium sulfate, and filtered. The filtrate was concentrated under reduced pressure and the residue was purified by thin layer chromatography with elution system A to obtain the title compound 1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methoxyurea 7 (12 mg, white solid), yield: 33.6%.

MS m/z (ESI): 673.8 [M+1]

$^1$H NMR (400 MHz, CDCl$_3$) δ 7.85 (d, 2H), 7.64-7.70 (m, 3H), 7.53 (d, 1H), 7.39-7.42 (m, 1H), 7.23-7.28 (m, 3H), 7.06 (t, 1H), 6.92 (t, 1H), 5.57-5.65 (m, 2H), 3.93 (s, 3H), 3.87 (s, 3H), 3.72 (s, 2H), 2.36 (s, 6H).

Example 8

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methylurea

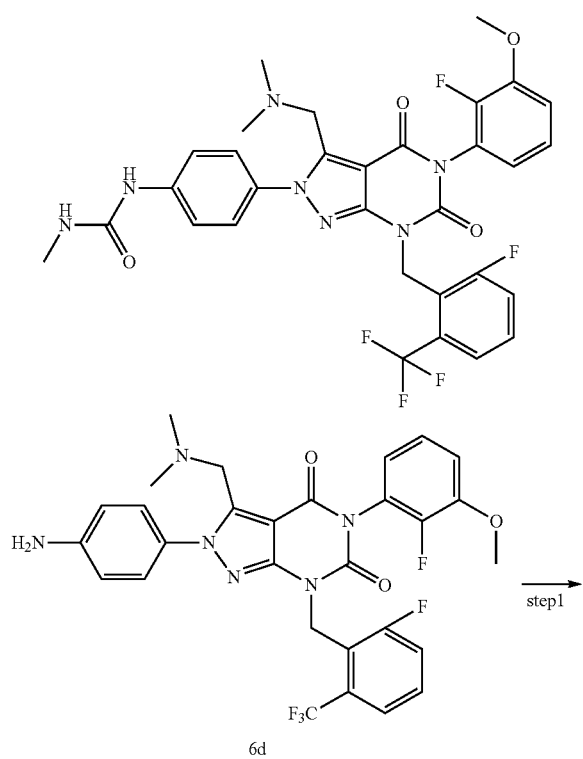

Step 1

1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methylurea Acetic acid (62 mg, 1.03 mmol) was dissolved in 1 mL of toluene, and added with N,N-diisopropylethylamine (0.28 mL, 1.58 mmol) and diphenylphosphoryl azide (0.20 mL, 0.98 mmol). After reacting for 1.5 hours at 70° C., the reaction solution was added with 2-(4-aminophenyl)-3-((dimethylamino)methyl)-5-(2-fluoro-3-methoxyphenyl)-7-(2-fluoro-6-(trifluoromethyl)benzyl)-2H-pyrazolo[3,4-d]pyrimidine-4,6(5H,7H)-dione 6d (30 mg, 0.050 mmol) and 1 mL of dichloromethane, and further reacted for 12 hours at room temperature. The reaction was stopped. The reaction solution was added with 5 mL of saturated sodium bicarbonate, and then extracted with dichloromethane (25 mL×1). The organic phase was washed with water (10 mL×1) and saturated sodium chloride solution (10 mL×1), dried over anhydrous sodium sulfate, and filtered. The filtrate was concentrated under reduced pressure and the residue was purified by thin layer chromatography with elution system A to obtain the crude title compound, which was further purified by thin layer chromatography with elution system A to obtain the title compound 1-(4-(3-((dimethylamino)methyl)-5-(2-fluoro-3-methoxyphenyl)-7-(2-fluoro-6-(trifluoromethyl)benzyl)-4,6-dioxo-4,5,6,7-tetrahydro-2H-pyrazolo[3,4-d]pyrimidin-2-yl)phenyl)-3-methylurea 8 (13 mg, white solid), yield 39.4%.

MS m/z (ESI): 658.2 [M+1]

$^1$H NMR (400 MHz, CDCl$_3$) δ 7.76 (d, 2H), 7.51-7.53 (m, 1H), 7.47 (d, 2H), 7.39-7.40 (m, 1H), 7.24 (t, 1H), 7.19 (t, 1H), 7.04 (t, 1H), 6.89 (t, 1H), 6.74 (m, 1H), 5.56-5.64 (m, 2H), 4.85 (s, 1H), 3.92 (s, 3H), 3.77 (s, 2H), 2.88 (d, 3H), 2.38 (s, 6H).

Example 9

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methylurea

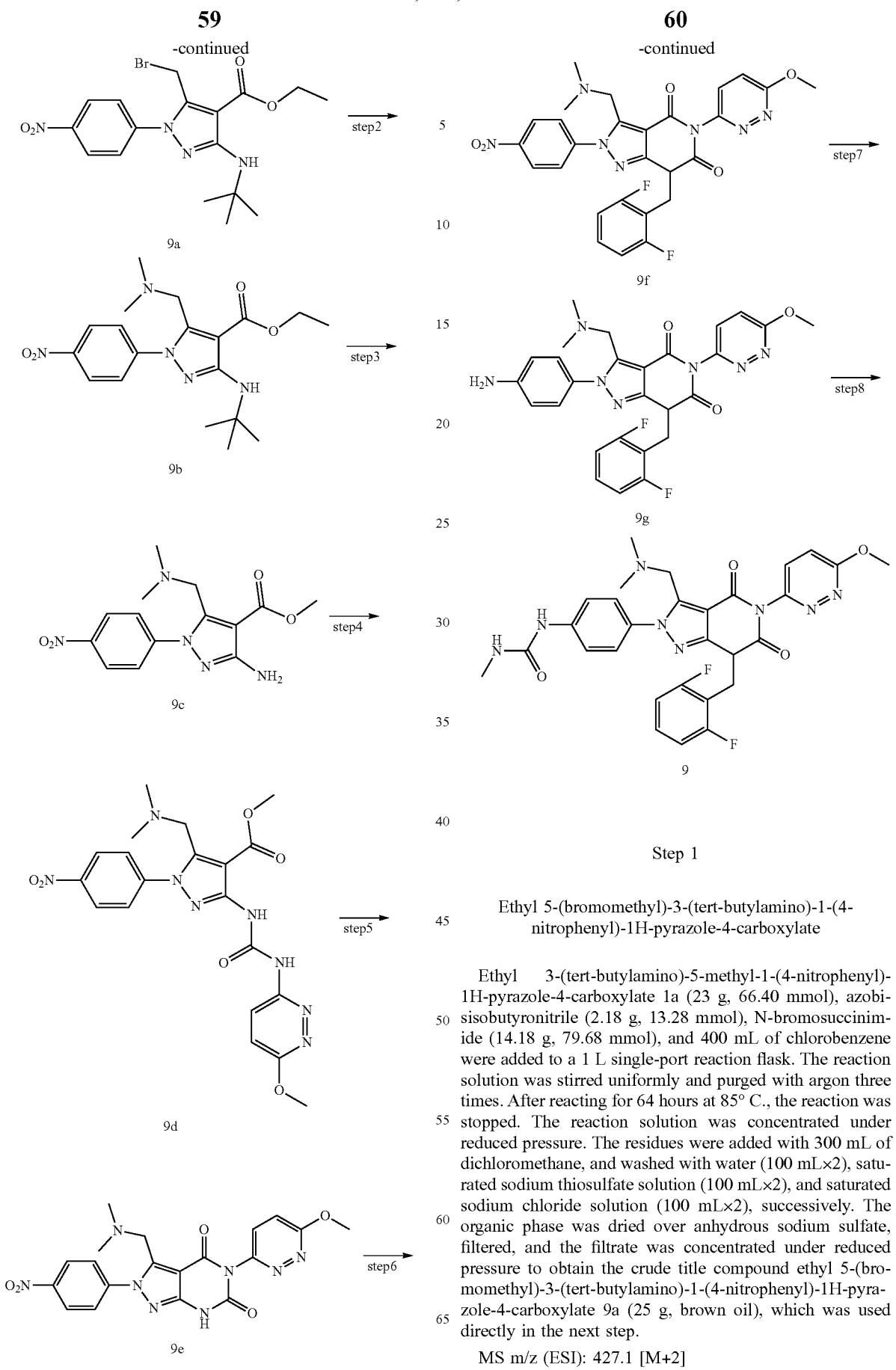

Step 1

Ethyl 5-(bromomethyl)-3-(tert-butylamino)-1-(4-nitrophenyl)-1H-pyrazole-4-carboxylate Ethyl 3-(tert-butylamino)-5-methyl-1-(4-nitrophenyl)-1H-pyrazole-4-carboxylate 1a (23 g, 66.40 mmol), azobisisobutyronitrile (2.18 g, 13.28 mmol), N-bromosuccinimide (14.18 g, 79.68 mmol), and 400 mL of chlorobenzene were added to a 1 L single-port reaction flask. The reaction solution was stirred uniformly and purged with argon three times. After reacting for 64 hours at 85° C., the reaction was stopped. The reaction solution was concentrated under reduced pressure. The residues were added with 300 mL of dichloromethane, and washed with water (100 mL×2), saturated sodium thiosulfate solution (100 mL×2), and saturated sodium chloride solution (100 mL×2), successively. The organic phase was dried over anhydrous sodium sulfate, filtered, and the filtrate was concentrated under reduced pressure to obtain the crude title compound ethyl 5-(bromomethyl)-3-(tert-butylamino)-1-(4-nitrophenyl)-1H-pyrazole-4-carboxylate 9a (25 g, brown oil), which was used directly in the next step.

MS m/z (ESI): 427.1 [M+2]

Step 2

Ethyl 3-(tert-butylamino)-5-((dimethylamino)methyl)-1-(4-nitrophenyl)-1H-pyrazole-4-carboxylate The crude ethyl 5-(bromomethyl)-3-(tert-butylamino)-1-(4-nitrophenyl)-1H-pyrazole-4-carboxylate 9a (25 g, 58.78 mmol), a solution of dimethyl amine in THF (88 mL, 176.35 mmol) and 120 mL of THF were added to a 500 mL single-port reaction flask, and stirred until dissolution. After stirring for 3 hours at room temperature, the reaction was stopped. The reaction solution was concentrated under reduced pressure. The residue was purified by silica gel column chromatography with eluent system C to obtain the title compound ethyl 3-(tert-butyl amino)-5-((dimethylamino)methyl)-1-(4-nitrophenyl)-1H-pyrazole-4-carboxylate 9b (6 g, brown oil), yield 26.2%.

MS m/z (ESI): 390.2 [M+1]

Step 3

Methyl 3-amino-5-((dimethylamino)methyl)-1-(4-nitrophenyl)-1H-pyrazole-4-carboxylate Ethyl 3-(tert-butyl amino)-5-((dimethylamino)methyl)-1-(4-nitrophenyl)-1H-pyrazole-4-carboxylate 9b (6 g, 15.41 mmol) and 80 mL of trifluoroacetic acid were added to a 100 mL single-port reaction flask and stirred uniformly. The mixture was heated to reflux for 1 hour and the reaction was stopped. The reaction solution was concentrated under reduced pressure. The residue was added with 50 mL of dichloromethane, and then added dropwise with saturated sodium bicarbonate solution to adjust the pH>7. The organic phase was dried over anhydrous magnesium sulfate, filtered, and concentrated under reduced pressure. The residue was added with 100 mL of methanol and 20 mL of dichloromethane, and stirred to dissolution. The resulting solution was added with potassium carbonate (6.37 g, 46.16 mmol), and stirred for 17 hours at room temperature, and then filtered. The filtrate was concentrated under reduced pressure and the residue was purified by silica gel column chromatography with eluent system B to obtain the title compound methyl 3-amino-5-((dimethylamino)methyl)-1-(4-nitrophenyl)-1H-pyrazole-4-carboxylate 9c (3.30 g, yellow solid), yield 67.1%.

MS m/z (ESI): 320.2 [M+1]

Step 4

Methyl 5-((dimethylamino)methyl)-3-(3-(6-methoxypyridazin-3-yl)ureido)-1-(4-nitrophenyl)-1H-pyrazole-4-carboxylate Methyl 3-amino-5-((dimethylamino)methyl)-1-(4-nitrophenyl)-1H-pyrazole-4-carboxylate 9c (3.30 g, 10.33 mmol) and 100 mL of dichloromethane were added to a 250 mL single-port reaction flask, and stirred uniformly. The resulting solution was added with triethylamine (5.8 mL, 41.32 mmol) and triphosgene (1.84 g, 6.20 mmol), and then stirred for 1 hour at room temperature. The reaction solution was added with 3-amino-6-methoxypyridazine (1.94 g, 15.50 mmol, prepared by a known method disclosed in "*Journal of Medicinal Chemistry*, 2006, 49(14), 4409-4424"), and stirred for 2 hours at room temperature. Then the reaction was stopped. The reaction solution was added with 200 mL of water, and extracted with dichloromethane (100 mL×3). The organic phase was concentrated under reduced pressure, and the residue was purified by silica gel column chromatography with eluent system B to obtain the title compound methyl 5-((dimethylamino)methyl)-3-(3-(6-methoxypyridazin-3-yl)ureido)-1-(4-nitrophenyl)-1H-pyrazole-4-carboxylate 9d (2.80 g, yellow solid), yield 57.6%.

MS m/z (ESI): 470.9 [M+1]

Step 5

3-((dimethylamino)methyl)-5-(6-methoxypyridazin-3-yl)-2-(4-nitrophenyl)-2H-pyrazolo[3,4-d]pyrimidine-4,6(5H,7H)-dione Methyl 5-((dimethylamino)methyl)-3-(3-(6-methoxypyridazin-3-yl)ureido)-1-(4-nitrophenyl)-1H-pyrazole-4-carboxylate 9d (2.80 g, 5.95 mmol) and 120 mL of methanol were added to a 250 mL single-port reaction flask, and stirred uniformly. The resulting solution was added with sodium methoxide (1.61 g, 29.76 mmol). The mixture was heated to 50° C. and stirred for 4 hours, and then the reaction was stopped. The reaction solution was concentrated under reduced pressure. The residue was added with 100 mL of water, and then added dropwise with concentrated hydrochloric acid to adjust the pH to 5 to 6. The solution was extracted with dichloromethane (100 mL×3). The organic phase was concentrated under reduced pressure, and the residue was purified by silica gel column chromatography with elution system B to obtain the title compound 3-((dimethylamino)methyl)-5-(6-methoxypyridazin-3-yl)-2-(4-nitrophenyl)-2H-pyrazol o[3,4-d]pyrimidine-4,6(5H,7H)-dione 9e (1.80 g, yellow solid), yield 69.0%.

MS m/z (ESI): 438.9 [M+1]

Step 6

7-(2,6-difluorobenzyl)-3-((dimethylamino)methyl)-5-(6-methoxypyridazin-3-yl)-2-(4-nitrophenyl)-2H-pyrazolo[3,4-d]pyrimidine-4,6(5H,7H)-dione 3-((dimethylamino)methyl)-5-(6-methoxypyridazin-3-yl)-2-(4-nitrophenyl)-2H-pyrazol o[3,4-d]pyrimidine-4,6(5H,7H)-dione 9e (900 mg, 2.05 mmol) and 50 mL of N,N-dimethylformamide were added to a 100 mL single-neck reactor flask, and stirred uniformly. The resulting solution was added with 2,6-difluorobenzyl chloride (367 mg, 2.26 mmol) and potassium carbonate (850 mg, 6.16 mmol). The mixture was heated to 40° C. and stirred for 17 hours, then the reaction was stopped. The reaction solution was added with 250 mL of water, and stirred for 20 minutes. The mixture was filtered, and the filter cake was dried in vacuo to obtain the title compound 7-(2,6-difluorobenzyl)-3-((dimethylamino)methyl)-5-(6-methoxypyridazin-3-yl)-2-(4-nitrophenyl)-2H-pyrazolo[3,4-d]pyrimidine-4,6(5H,7H)-dione 9f (1.10 g, yellow solid), yield 94.9%.

MS m/z (ESI): 564.9 [M+1]

Step 7

2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione 7-(2,6-difluorobenzyl)-3-((dimethylamino)methyl)-5-(6-methoxypyridazin-3-yl)-2-(4-nitrophenyl)-2H-pyrazolo[3,4-d]pyrimidine-4,6(5H,7H)-dione 9f (1 g, 1.77 mmol), 10% palladium on carbon (200 mg), and 80 mL of methanol were added to a 250 mL single-port reaction flask, and stirred uniformly. The resulting solution was purged with hydrogen 6 times, and then stirred for 17 hours at room temperature. The reaction was stopped. The reaction solution was filtered, and the filtrate was concentrated under reduced pressure to obtain the title compound 2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione 9g (785 mg, yellow solid), yield 82.9%.

MS m/z (ESI): 534.9 [M+1]

Step 8

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methylurea Acetic acid (483 mg, 8.04 mmol) and 15 mL of toluene were stirred to dissolution in 600 mL autoclave. The resulting solution was added with N,N-diisopropylethylamine (2.1 mL, 12.07 mmol) and diphenylphosphoryl azide (2.22 g, 8.07 mmol), successively. The mixture was heated to 75° C. and stirred for 1.5 hours. The reaction solution was added with 10 mL solution of 2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione 9g (480 mg, 0.80 mmol) in THF in an ice bath at 0° C. After completion of addition, the reaction solution was heated to 55° C. and stirred for 16 hours. Then the reaction was stopped. The reaction solution was added with 20 mL of dichloromethane and 20 mL of water, and subject to extraction. The organic phase was washed with saturated sodium bicarbonate solution (50 mL×1), water (50 mL×1), and saturated sodium chloride solution (50 mL×1), successively. The organic phase was dried over anhydrous sodium sulfate, and filtered. The filtrate was concentrated under reduced pressure and the residue was purified by silica gel column chromatography with eluent system A to obtain the crude product, which was further purified by thin layer chromatography with eluent system A to obtain the crude product (387 mg, brown solid), crude yield: 81.3%. The two crude batches were combined to obtain a total product of 823 mg, which was purified by thin layer chromatography with eluent system F. The resulting product was dissolved in methanol, and concentrated under reduced pressure until a solid was separated, which was subject to crystallization to obtain the title compound 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methylurea 9 (450 mg, white solid), total yield: 36.0%.

MS m/z (ESI): 592.3[M+1]

¹H NMR (400 MHz, CDCl₃) δ 8.17 (s, 1H), 7.54 (s, 1H), 7.42-7.45 (m, 4H), 7.24-7.30 (m, 2H), 6.88 (t, 2H), 5.95 (s, 1H), 5.38 (s, 2H), 4.23 (s, 3H), 3.69 (s, 2H), 2.91 (s, 3H), 2.33 (s, 6H).

Example 10

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-ethylurea

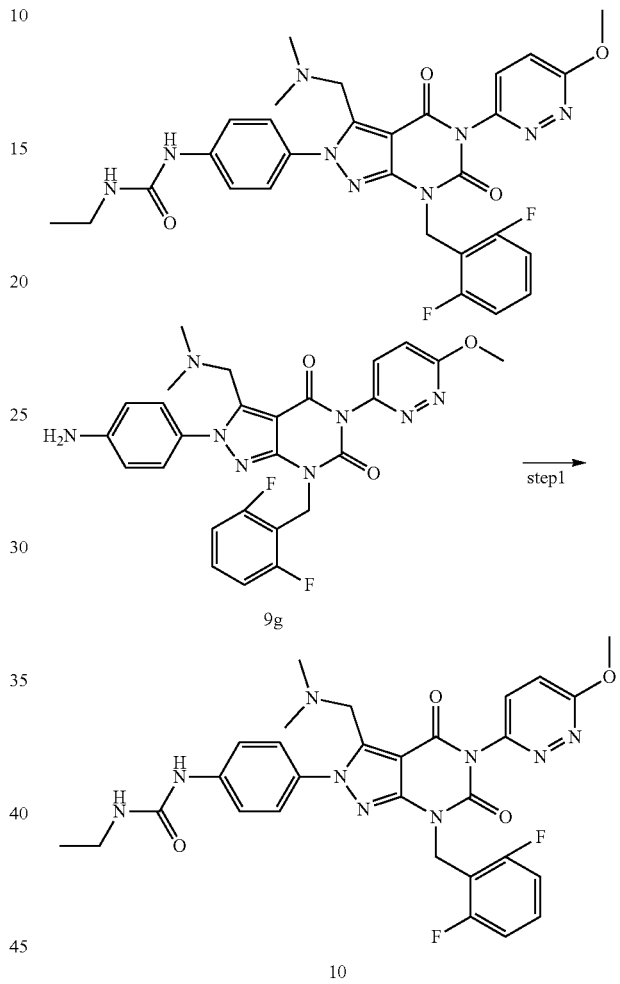

Step 1

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-ethylurea 2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione 9g (22 mg, 0.041 mmol) was dissolved in 2 mL of dichloromethane, and added with ethyl isocyanate (0.1 mL, 1.26 mmol). After reacting for 12 hours at 35° C., the reaction was stopped. The reaction solution was added with 5 mL of saturated sodium bicarbonate solution, and extracted with dichloromethane (30 mL×1). The organic phase was washed with water (10 mL×1), and saturated sodium chloride solution (10 mL×1), successively, dried over anhydrous sodium sulfate, and filtered. The filtrate was concentrated under reduced pressure, and the residue was purified by thin layer chromatography with elution system A to obtain the title compound 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-ethylurea 10 (10 mg, white solid), yield: 40.0%.

MS m/z (ESI): 606.2 [M+1]

$^1$H NMR (400 MHz, CDCl$_3$) δ 8.07 (s, 1H), 7.55 (d, 1H), 7.38-7.43 (m, 4H), 7.25-7.28 (m, 2H), 6.858 (t, 2H), 5.87 (t, 1H), 5.38 (s, 2H), 4.23 (s, 3H), 3.50 (s, 2H), 3.37 (t, 2H), 2.25 (s, 6H), 1.23 (t, 3H).

Example 11

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea

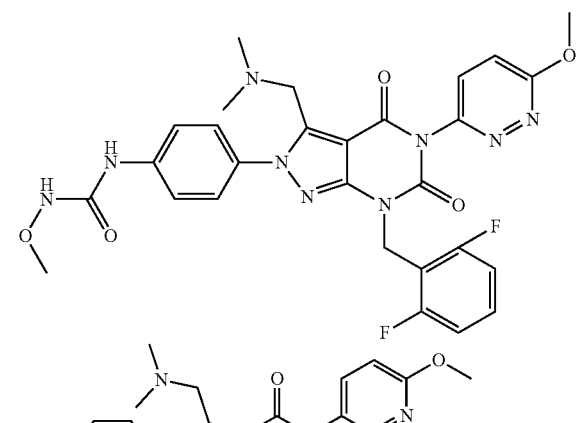

9g

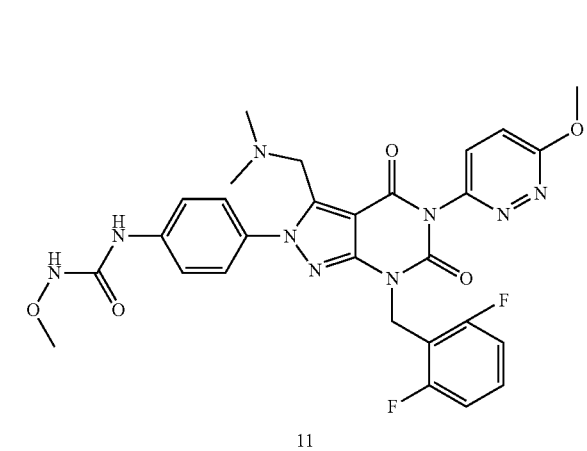

11

Step 1

1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea 2-(4-aminophenyl)-7-(2,6-difluorobenzyl)-3-((dimethylamino)methyl)-5-(6-methoxypyridazin-3-yl)-2H-pyrazolo[3,4-d]pyrimidine-4,6(5H,7H)-dione 9g (100 mg, 0.18 mmol) was dissolved in 5 mL of dichloromethane, and added with N,N-diisopropylethylamine (0.5 mL, 2.90 mmol) and triphosgene (46 mg, 0.15 mmol). The mixture was reacted for 45 minutes at room temperature, and then added with methoxyamine hydrochloride (92 mg, 1.12 mmol). The mixture was further reacted for 12 hours at 40° C., and then the reaction was stopped. The reaction solution was added with 5 mL of saturated sodium bicarbonate solution, and then extracted with dichloromethane (25 mL×1). The organic phase was washed with water (10 mL×1) and saturated sodium chloride solution (10 mL×1), successively, dried over anhydrous sodium sulfate, and filtered. The filtrate was concentrated under reduced pressure, and the residue was purified by thin layer chromatography with elution system A to obtain 62 mg of crude product, which was further purified by thin layer chromatography with elution system A for two times to obtain the title compound 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea 11 (45 mg, white solid), yield: 24.7%.

MS m/z (ESI): 608.3 [M+1]

$^1$H NMR (400 MHz, CDCl$_3$) δ 7.90 (d, 2H), 7.73 (s, 1H), 7.68 (d, 2H), 7.41 (d, 1H), 7.26-7.30 (m, 1H), 7.22 (s, 1H), 7.13 (s, 1H), 6.92 (t, 2H), 5.44 (s, 2H), 4.21 (s, 3H), 3.88 (s, 3H), 3.70 (s, 2H), 2.35 (s, 6H).

Example 12

1-(4-(3-((dimethylamino)methyl)-7-(2-fluoro-6-(trifluoromethyl)benzyl)-5-(6-methoxypyridazin-3-yl)-4,6-dioxo-4,5,6,7-tetrahydro-2H-pyrazolo[3,4-d]pyrimidin-2-yl)phenyl)-3-methylurea

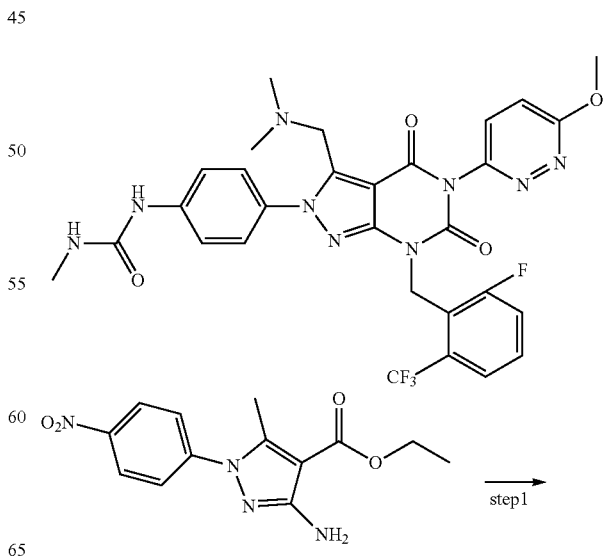

1b

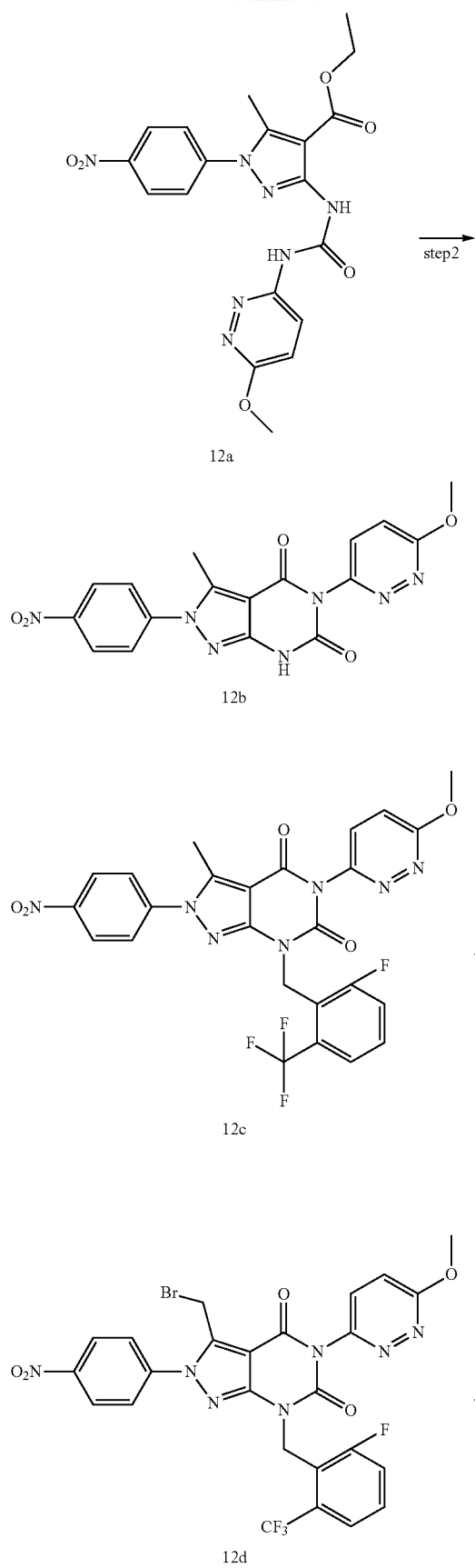

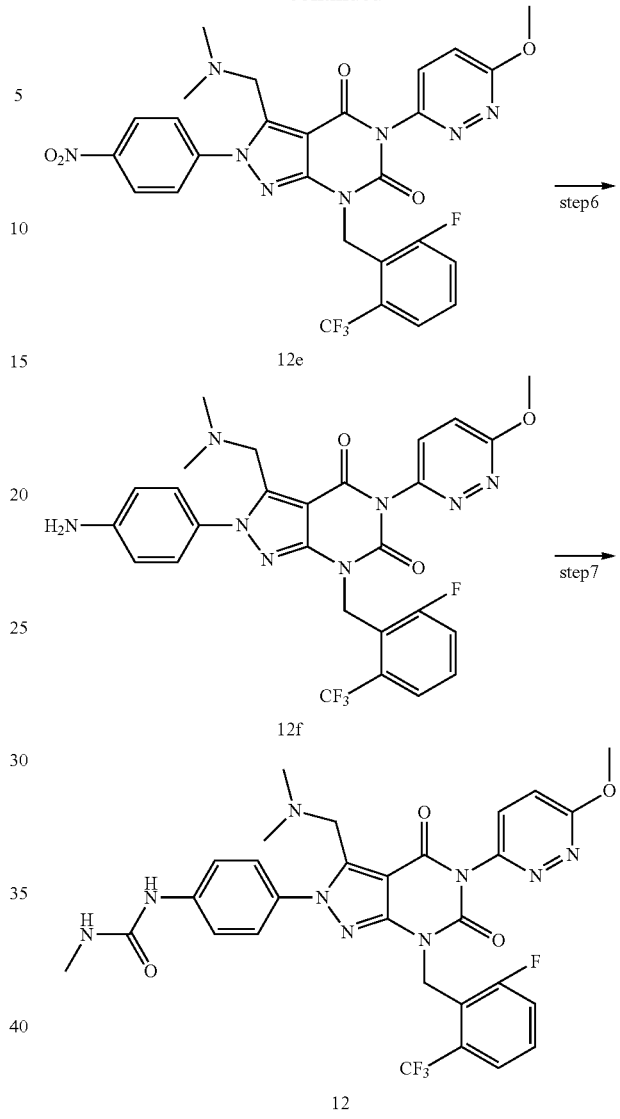

Step 1

Ethyl 3-(3-(6-methoxypyridazin-3-yl)ureido)-5-methyl-1-(4-nitrophenyl)-1H-pyrazole-4-carboxylate Ethyl 3-amino-5-methyl-1-(4-nitrophenyl)-1H-pyrazole-4-carboxylate 1b (10.80 g, 37.20 mmol) was dissolved in 500 mL of dichloromethane, and then added with triethylamine (20 mL, 144 mmol) and triphosgene (5.20 g, 17.5 mmol), successively. After reacting for 1 hour at room temperature, the reaction solution was added with 3-amino-6-methoxypyridazine (6.60 g, 52.3 mmol), and stirred for 12 hours at room temperature. Then the reaction was stopped. The resulting products were combined, and added with 100 mL of water. The solution was subjected to extraction. The organic phase was washed with water (100 mL×1) and saturated sodium chloride solution (100 mL×1), dried over anhydrous sodium sulfate, and filtered. The filtrate was concentrated under reduced pressure and the residue was purified by silica gel column chromatography with eluent system C to obtain the title compound ethyl 3-(3-(6- methoxypyridazin-3-yl)ureido)-5-methyl-1-(4-nitrophenyl)-1H-pyrazole-4-carboxylate 12a (8.72 g, pale yellow solid), yield: 53.0%.

Step 2

5-(6-methoxypyridazin-3-yl)-3-methyl-2-(4-nitrophenyl)-2H-pyrazolo[3,4-d]pyrimidine-4,6(5H,7H)-dione Ethyl 3-(3-(6-methoxypyridazin-3-yl)ureido)-5-methyl-1-(4-nitrophenyl)-1H-pyrazole-4-carboxylate 12a (8.72 g, 19.70 mmol) was dissolved in 150 mL of methanol, and added with sodium methoxide (2.70 g, 50 mmol). The mixture was heated to 55° C. and stirred for 12 hours, then the reaction was stopped. The reaction solution was concentrated under reduced pressure. The residue was added dropwise with 1 M hydrochloric acid solution to adjust the pH<7, and filtered. The filter cake was washed with water (30 mL×1), methanol (30 mL×1), and ether (20 mL×1), successively, and dried in vacuo to obtain the crude title compound 5-(6-methoxypyridazin-3-yl)-3-methyl-2-(4-nitrophenyl)-2H-pyrazolo[3,4-d]pyrimidine-4,6(5H,7H)-dione 12b (8.34 mg, light yellow solid), which was used directly in the next step.

MS m/z (ESI): 396.0 [M+1]

Step 3

7-(2-fluoro-6-(trifluoromethyl)benzyl)-5-(6-methoxypyridazin-3-yl)-3-methyl-2-(4-nitro phenyl)-2H-pyrazolo[3,4-d]pyrimidine-4,6(5H,7H)-dione 2-(bromomethyl)-1-fluoro-3-(trifluoromethyl)benzene (purchased from Sinopharm Chemical Reagent Co., Ltd., product number XW239870821) (308 mg, 1.20 mmol) was dissolved in 20 mL of N,N-dimethyl formamide, and added with the crude 5-(6-methoxypyridazin-3-yl)-3-methyl-2-(4-nitrophenyl)-2H-pyrazolo[3,4-d]pyrimidine-4,6(5H,7H)-dione 12b (395 mg, 1 mmol) and potassium carbonate (276 mg, 2 mmol), successively. After reacting for 2 hours at room temperature, the reaction solution was stopped. The reaction solution was poured into 100 mL of water, and filtered. The filter cake was dried to obtain the title compound 7-(2-fluoro-6-(trifluoromethyl)benzyl)-5-(6-methoxypyridazin-3-yl)-3-methyl-2-(4-nitro phenyl)-2H-pyrazolo[3,4-d]pyrimidine-4,6(5H,7H)-dione 12c (465 mg, yellow solid), yield: 81.4%.

MS m/z (ESI): 570.0 [M−1]

Step 4

3-(bromomethyl)-7-(2-fluoro-6-(trifluoromethyl) benzyl)-5-(6-methoxypyridazin-3-yl)-2-(4-nitrophenyl)-2H-pyrazolo[3,4-d]pyrimidine-4,6(5H,7H)-dione 7-(2-fluoro-6-(trifluoromethyl)benzyl)-5-(6-methoxypyridazin-3-yl)-3-methyl-2-(4-nitro phenyl)-2H-pyrazolo[3,4-d]pyrimidine-4,6(5H,7H)-dione 12c (465 mg, 0.81 mmol), azobisisobutyronitrile (13 mg, 0.081 mmol), N-bromosuccinimide (174 mg, 0.97 mmol), and 20 mL of chlorobenzene were added to a 100 mL reaction flask. The mixture was reacted for 17 hours at 80° C. under argon atmosphere, then the reaction was stopped. The reaction solution was concentrated under reduced pressure to obtain the crude title compound 3-(bromomethyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione 12d (600 mg, yellow oil), which was used directly in the next step.

MS m/z (ESI): 650.1 [M+1]

Step 5

3-((dimethylamino)methyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione The crude 3-(bromomethyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione 12d (15 mg, 0.033 mmol) was dissolved in 20 mL of THF, and added with a 2M solution of dimethylamine in THF (1 mL, 2.03 mmol). The mixture was reacted for 2 hours at room temperature, and then the reaction was stopped. The reaction solution was concentrated under reduced pressure. The residues were purified by thin layer chromatography with elution system A to obtain the title compound 3-((dimethylamino)methyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione 12e (85 mg, yellow solid), yield: 17.0%.

MS m/z (ESI): 615.2 [M+1]

Step 6

2-(4-aminophenyl)-3-((dimethylamino)methyl)-7-(2-fluoro-6-(trifluoromethyl)benzyl)-5-(6-methoxypyridazin-3-yl)-2H-pyrazolo[3,4-d]pyrimidine-4,6 (5H,7H)-dione 3-((dimethylamino)methyl)-7-(2-fluoro-6-(trifluoromethyl)benzyl)-5-(6-methoxypyridazin-3-yl)-2-(4-nitrophenyl)-2H-pyrazolo[3,4-d]pyrimidine-4,6(5H,7H)-dione 12e (100 mg, 0.14 mmol) was dissolved in 5 mL of formic acid, and added with 10% palladium on carbon (48 mg). The mixture was purged with hydrogen under normal pressure three times, and then reacted for 3 hours at room temperature under hydrogen atmosphere. The reaction was stopped and filtered. The filtrate was poured into 10 mL of water, and then added dropwise with saturated sodium bicarbonate solution to adjust the pH>7. The solution was extracted with dichloromethane (25 mL×3). The organic phases were combined, dried over anhydrous sodium sulfate, and filtered. The filtrate was concentrated under reduced pressure and the residue was purified by thin layer chromatography with a elution system A to obtain the title compound 2-(4-aminophenyl)-3-((dimethylamino)methyl)-7-(2-fluoro-6-(trifluoromethyl)benzyl)-5-(6-methoxypyridazin-3-yl)-2H-pyrazolo[3,4-d]pyrimidine-4,6(5H,7H)-dione 12f (50 mg, white solid), yield: 53.0%.

MS m/z (ESI): 585.2 [M+1]

Step 7

1-(4-(3-((dimethylamino)methyl)-7-(2-fluoro-6-(trifluoromethyl)benzyl)-5-(6-methoxypyridazin-3-yl)-4,6-dioxo-4,5,6,7-tetrahydro-2H-pyrazolo[3,4-d]pyrimidin-2-yl)phenyl)-3-methylurea Acetic acid (51 mg, 085 mmol) and N,N-diisopropylethylamine (0.22 mL, 1.28 mmol) were dissolved in 2 mL of toluene, and added with diphenylphosphoryl azide (236 mg, 0.86 mmol). After reacting for 1.5 hours at 75° C., the reaction solution was added with a 2 mL solution of 2-(4-aminophenyl)-3-((dimethylamino)methyl)-7-(2-fluoro-6-(trifluoromethyl)benzyl)-5-(6-methoxypyridazin-3-yl)-2H-pyrazolo[3,4-d]pyrimidine-4,6(5H,7H)-dione 12f (15 mg, 0.033 mmol) in THF. The resulting solution was reacted for 12 hours at 50° C., and then the reaction was stopped. The reaction solution was added with 10 mL of saturated sodium bicarbonate solution, and then extracted with dichloromethane (20 mL×1). The organic phase was collected and washed with water (10 mL×1) and saturated sodium chloride (10 mL×1), successively. The organic phase was concentrated under reduced pressure. The residue was purified by thin layer chromatography with elution system A to obtain the title compound 1-(4-(3-((dimethylamino)methyl)-7-(2-fluoro-6-(trifluoromethyl)benzyl)-5-(6-methoxypyridazin-3-yl)-4,6-dioxo-4,5,6,7-tetrahydro-2H-pyrazolo[3,4-d]pyrimidin-2-yl)phenyl)-3-methylurea 12 (20 mg, white solid), yield: 36.3%.

MS m/z (ESI): 642.3 [M+1]

$^1$H NMR (400 MHz, CDCl$_3$) δ 8.19 (s, 1H), 7.56 (d, 1H), 7.43-7.46 (m, 3H), 7.34-7.39 (m, 3H), 7.27 (d, 1H), 7.16 (t, 1H), 6.05 (s, 1H), 5.48 (s, 2H), 4.22 (s, 3H), 3.48 (s, 2H), 2.93 (d, 3H), 2.21 (s, 6H).

Example 13

1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-ethylurea

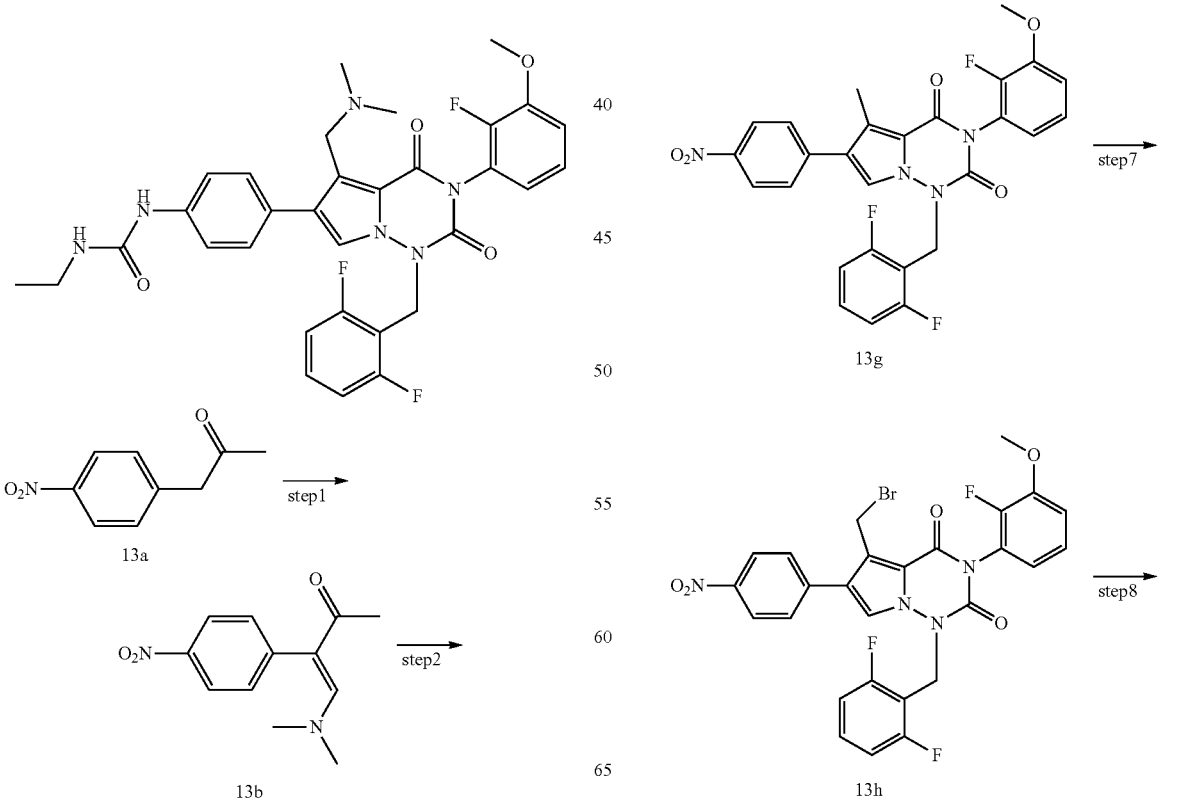

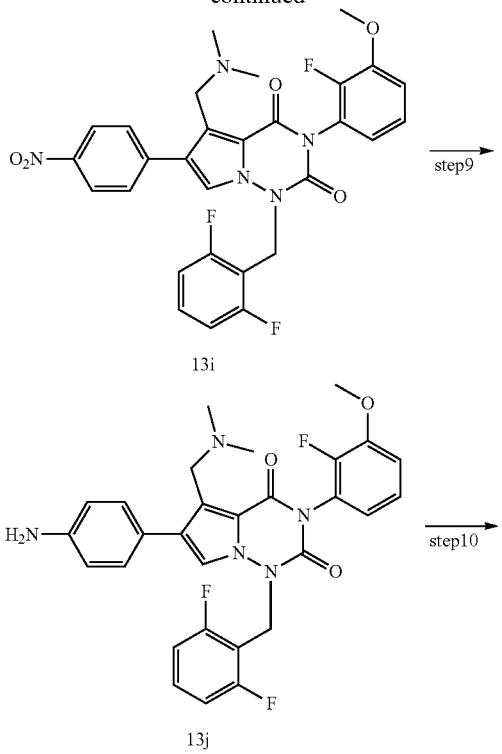

Step 1

(E)-4-(dimethylamino)-3-(4-nitrophenyl)but-3-en-2-one 1-(4-nitrophenyl)propan-2-one 13a (3.8 g, 21.21 mmol) and N,N-dimethyl formamide dimethyl acetal were added to a 50 mL flask. After reacting for 30 minutes at 100° C., the reaction was stopped and added with 150 mL of dichloromethane under stirring. The resulting product was purified by silica gel column chromatography with eluent system A to obtain the title compound (E)-4-(dimethylamino)-3-(4-nitrophenyl)but-3-en-2-one 13b (3 g, yellow solid), yield: 60.5%.

MS m/z (ESI): 235.0 [M+1]

Step 2

Ethyl 3-methyl-4-(4-nitrophenyl)-1H-pyrrole-2-carboxylate (E)-4-(dimethylamino)-3-(4-nitrophenyl) but-3-en-2-one 13b (1.50 g, 6.48 mmol) and 2-aminoacetylacetatehydrochloride (1.40 g, 7.78 mmol) were dissolved in 40 mL of acetic acid. The mixture was reacted at room temperature for 16 hours, and at 100° C. for 5 hours, then the reaction was stopped. The reaction solution was concentrated under reduced pressure. The residue was added with 120 mL of dichloromethane, and washed with saturated sodium bicarbonate solution (50 mL×1). The organic phase was dried over anhydrous sodium sulfate, and filtered. The filtrate was concentrated under reduced pressure, and the residue was slurried with 15 mL of ethylacetate, and then filtered. The filter cake was dried to obtain the title compound ethyl 3-methyl-4-(4-nitrophenyl)-1H-pyrrole-2-carboxylate 13c (412 mg, yellow solid), yield: 24.5%.

MS m/z (ESI): 273.1 [M−1]

Step 3

Ethyl 1-amino-3-methyl-4-(4-nitrophenyl)-1H-pyrrole-2-carboxylate

Ethyl 3-methyl-4-(4-nitrophenyl)-1H-pyrrole-2-carboxylate 13c (412 mg, 1.50 mmol) was dissolved in 6 mL of N,N-dimethyl formamide, and then added with sodium hydride (72 mg, 1.80 mmol) in an ice bath. The mixture was reacted for 30 minutes at room temperature, and then added with 20 mL of chloramines solution. The mixture was further reacted for 2 hours at room temperature and then the reaction was stopped. The reaction solution was added with 50 mL of saturated sodium thiosulfate solution, stirred for 10 minutes, and left to separate into layers. The aqueous phase was extracted with ether (30 mL×3). The organic phase was washed with saturated sodium chloride solution (100 mL×2), dried over anhydrous sodium sulfate, and filtered. The filtrate was concentrated under reduced pressure to obtain the title compound ethyl 1-amino-3-methyl-4-(4-nitrophenyl)-1H-pyrrole-2-carboxylate 13d (381 mg, yellow solid), yield 87.7%.

MS m/z (ESI): 290.2 [M+1]

Step 4

Ethyl 1-(3-(2-fluoro-3-methoxyphenyl)ureido)-3-methyl-4-(4-nitrophenyl)-1H-pyrrole-2-carboxylate Ethyl 1-amino-3-methyl-4-(4-nitrophenyl)-1H-pyrrole-2-carboxylate 13d (381 mg, 1.30 mmol) was added to 30 mL of dichloromethane and stirred until dissolution, then added with triethylamine (328 mg, 3.25 mmol) and triphosgene (157 mg, 0.53 mmol). After reacting for 30 minutes at room temperature, the reaction solution was added with 2-fluoro-3-methoxyaniline (202 mg, 1.43 mmol). The mixture was further reacted at room temperature for 2 hours. The reaction was stopped. The reaction solution was filtered. The filter cake was washed with water (10 mL×2) and ethylacetate (2 mL×3), successively, and then dried to obtain the title compound ethyl 1-(3-(2-fluoro-3-methoxyphenyl)ureido)-3-methyl-4-(4-nitrophenyl)-1H-pyrrole-2-carboxylate 13e (296 mg, yellow solid), yield 49.9%.

MS m/z (ESI): 457.3 [M+1]

Step 5

3-(2-fluoro-3-methoxyphenyl)-5-methyl-6-(4-nitrophenyl)pyrrolo[2,1-f][1,2,4]triazine-2,4(1H,3H)-dione Ethyl 1-(3-(2-fluoro-3-methoxyphenyl)ureido)-3-methyl-4-(4-nitrophenyl)-1H-pyrrole-2-carboxylate 13e (290 mg, 0.64 mmol) and sodium hydroxide (128 mg, 3.20 mmol) were dissolved in 10 mL of dichloromethane. After reacting for 2 hours at 80° C., the reaction was stopped. The reaction solution was cooled to room temperature, and then added dropwise with 1 M hydrochloric acid solution to adjust the pH to 3 to 4. A solid was separated and filtered. The filter cake was washed with water (20 mL×3) and ethanol (10 mL×1), successively to obtain the title compound 3-(2-fluoro-3-methoxyphenyl)-5-methyl-6-(4-nitrophenyl)pyrrolo[2,1-f][1,2,4]triazine-2,4(1H,3H)-dione 13f (192 mg, gray solid), yield 73.3%.

MS m/z (ESI): 411.0 [M+1]

Step 6

1-(2,6-difluorobenzyl)-3-(2-fluoro-3-methoxyphenyl)-5-methyl-6-(4-nitrophenyl)pyrrolo[2,1-f][1,2,4]triazine-2,4(1H,3H)-dione 3-(2-fluoro-3-methoxyphenyl)-5-methyl-6-(4-nitrophenyl)pyrrolo[2,1-f][1,2,4]triazine-2,4(1H,3H)-dione 13f (192 mg, 0.47 mmol), 2-(chloromethyl)-1,3-difluorobenzene (84 mg, 0.52 mmol) and potassium carbonate (162 mg, 1.75 mmol) were added to 10 mL of N,N-dimethyl formamide. After reacting for 16 hours at 50° C., the reaction was stopped. The reaction solution was concentrated under reduced pressure. The residue was added with 20 mL of water, (20 mL×1) and extracted with dichloromethane (20 mL×1). The aqueous phase was extracted with dichloromethane (10 mL×3). The organic phases were collected, dried over anhydrous sodium sulfate, and filtered. The filtrate was concentrated under reduced pressure, and the residue was purified by thin layer chromatography with elution system A to obtain the title compound 1-(2,6-difluorobenzyl)-3-(2-fluoro-3-methoxyphenyl)-5-methyl-6-(4-nitrophenyl)pyrrolo[2,1-f][1,2,4]triazine-2,4(1H,3H)-dione 13g (160 mg, yellow solid), yield: 63.7%.

MS m/z (ESI): 537.0 [M+1]

Step 7

5-(bromomethyl)-1-(2,6-difluorobenzyl)-3-(2-fluoro-3-methoxyphenyl)-6-(4-nitrophenyl)pyrrolo[2,1-f][1,2,4]triazine-2,4(1H,3H)-dione 1-(2,6-difluorobenzyl)-3-(2-fluoro-3-methoxyphenyl)-5-methyl-6-(4-nitrophenyl)pyrrolo[2,1-f][1,2,4]triazine-2,4(1H,3H)-dione 13g (120 mg, 0.22 mmol), azobisisobutyronitrile (8 mg, 0.044 mmol) and N-bromosuccinimide (47 mg, 0.26 mmol) were dissolved in 5 mL of chlorobenzene. The mixture was reacted for 16 hours at 85° C. under argon atmosphere, and then the reaction was stopped. The reaction solution was cooled to room temperature and concentrated under reduced pressure. The residue was added with 10 mL of water, and extracted with dichloromethane (10 mL×1). The aqueous phase was extracted with dichloromethane (10 mL×3). The organic phases were combined, washed with saturated sodium chloride solution (20 mL×1), dried over anhydrous sodium sulfate, and filtered. The filtrate was concentrated under reduced pressure to obtain the title compound 5-(bromomethyl)-1-(2,6-difluorobenzyl)-3-(2-fluoro-3-methoxyphenyl)-6-(4-nitrophenyl)pyrrolo[2,1-f][1,2,4]triazine-2,4(1H,3H)-dione 13h (130 mg, yellow solid), yield: 96.2%.

MS m/z (ESI): 616.0 [M+1]

Step 8

1-(2,6-difluorobenzyl)-5-((dimethylamino)methyl)-3-(2-fluoro-3-methoxyphenyl)-6-(4-nitrophenyl)pyrrolo[2,1-f][1,2,4]triazine-2,4(1H,3H)-dione The crude 5-(bromomethyl)-1-(2,6-difluorobenzyl)-3-(2-fluoro-3-methoxyphenyl)-6-(4-nitrophenyl)pyrrolo[2,1-f][1,2,4]triazine-2,4(1H,3H)-dione 13h (130 mg, 0.21 mmol) and N,N-diisopropylethylamine (81 mg, 0.63 mmol) were dissolved in 5 mL of THF, and added with 1.6 mL solution of dimethylamine in tetrahydrofuran. The mixture was reacted for 1 hour at 0 to 5° C., and then the reaction was stopped. The reaction solution was concentrated under reduced pressure, and the residue was purified by thin layer chromatography with elution system A to obtain the title compound 1-(2,6-difluorobenzyl)-5-((dimethylamino)methyl)-3-(2-fluoro-3-methoxyphenyl)-6-(4-nitrophenyl)pyrrolo[2,1-f][1,2,4]triazine-2,4(1H,3H)-dione 13i (40 mg, yellow solid), yield: 33.1%.

MS m/z (ESI): 580.2 [M+1]

Step 9

6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione 1-(2,6-difluorobenzyl)-5-((dimethylamino)methyl)-3-(2-fluoro-3-methoxyphenyl)-6-(4-nitrophenyl)pyrrolo[2,1-f][1,2,4]triazine-2,4(1H,3H)-dione 13i (40 mg, 0.069 mmol), ammonium chloride (30 mg, 0.55 mmol), and iron (16 mg, 0.28 mmol) were dissolved in 5 mL mixture of ethanol and water (V/V=4:1). The mixture was reacted for 1 hour at 80° C. and then the reaction was stopped. The reaction solution was added with 20 mL of water, and then extracted with dichloromethane (10 mL×3). The organic phases were combined, washed with saturated sodium chloride solution (20 mL×1), dried over anhydrous sodium sulfate, and filtered. The filtrate was concentrated under reduced pressure and the residue was purified by thin layer chromatography with elution system A to obtain the title compound 6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione 13j (20 mg, yellow solid), yield: 52.6%.

MS m/z (ESI): 550.2 [M+1]

Step 10

1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-ethylurea 6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione 13j (20 mg, 0.036 mmol) and ethyl isocyanate (13 mg, 0.18 mmol) were dissolved in 5 mL of tetrahydrofuran in a 30 mL sealed tube. After reacting for 16 hours at 50° C., the reaction was stopped. The reaction solution was concentrated under reduced pressure, and the residue was purified by thin layer chromatography with elution system A to obtain the title compound 1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-ethylurea 13 (15 mg, white solid), yield: 68.1%.

MS m/z (ESI): 621.3 [M+1]

$^1$H NMR (400 MHz, DMSO-$d_6$) δ 7.87-7.77 (m, 4H), 7.69 (s, 1H), 7.58-7325 (m, 4H), 7.12-7.08 (m, 1H), 6.80-6.71 (m, 1H), 4.42 (s, 2H), 3.83 (s, 3H), 3.45-3.50 (m, 2H), 3.20-3.31 (m, 2H), 2.16 (s, 6H), 1.12-1.03 (m, 3H)

Example 14

1-(4-(1-(2,6-difluorobenzyl)-5-((dimethylamino) methyl)-3-(2-fluoro-3-methoxyphenyl)-2,4-dioxo-1, 2,3,4-tetrahydropyrrolo[2,1-f][1,2,4]triazin-6-yl) phenyl)-3-methylurea

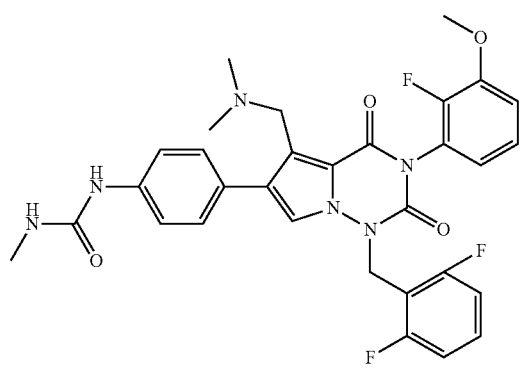

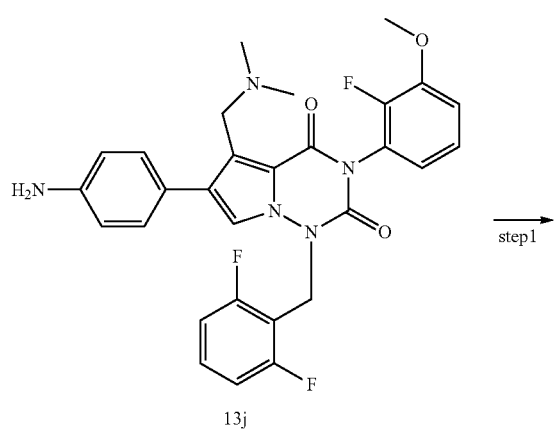

13j

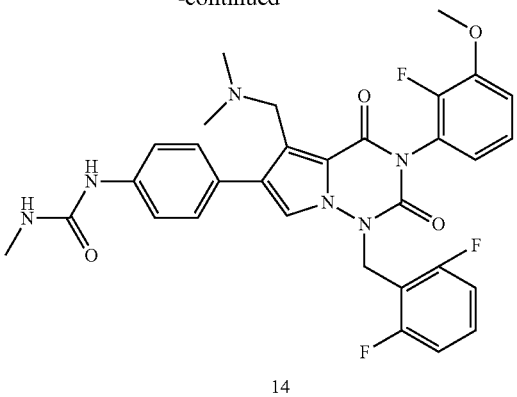

14

Step 1

1-(4-(1-(2,6-difluorobenzyl)-5-((dimethylamino) methyl)-3-(2-fluoro-3-methoxyphenyl)-2,4-dioxo-1, 2,3,4-tetrahydropyrrolo[2,1-][1,2,4]triazin-6-yl)phenyl)-3-methylurea Acetic acid (70 mg, 1.12 mmol) and N,N-diisopropylethylamine (0.32 mL, 1.80 mmol) were dissolved in 1 mL of toluene, and then added with diphenylphosphoryl azide (0.25 mL, 1.20 mmol). After reacting for 1.5 hours at 70° C., the reaction solution was added with a 1 mL solution of 6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione 13j (30 mg, 0.054 mmol) in dichloromethane. The reaction solution was further reacted for 12 hours at room temperature, and then added with 15 mL of water, and extracted with dichloromethane (30 mL×1). The organic phase was washed with saturated sodium bicarbonate (10 mL×1), water (10 mL×1), and saturated sodium chloride solution (10 mL×1), successively, dried over anhydrous sodium sulfate, and filtered. The filtrate was concentrated under reduced pressure and the residue was purified by thin layer chromatography with elution system A to obtain the title compound 1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methylurea 14 (9 mg, white solid), yield: 27.3%.

MS m/z (ESI): 606.9 [M+1]

$^1$H NMR (400 MHz, CDCl$_3$) δ 8.86 (s, 1H), 7.55 (s, 2H), 7.24-7.35 (m, 3H), 7.68-7.14 (m, 6H), 6.21 (s, 1H), 5.60-5.74 (m, 2H), 4.54-4.59 (m, 2H), 3.97 (s, 3H), 2.77 (s, 3H), 2.55 (s, 6H).

Example 15

1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methoxyurea

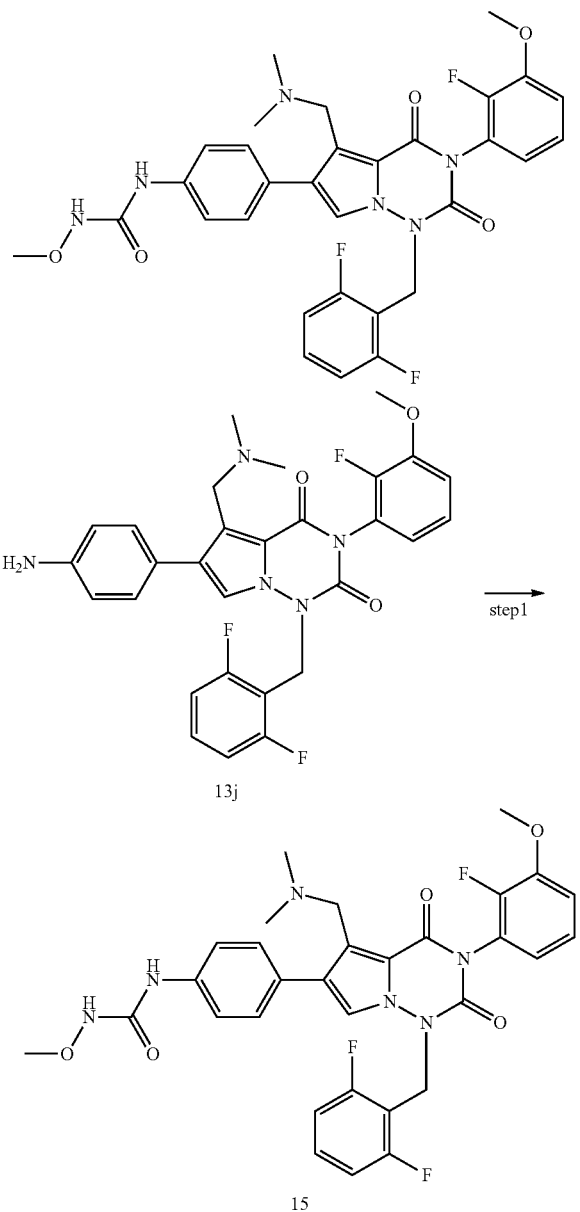

Step 1

1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methoxyurea 6-(4-aminophenyl)-1-(2,6-difluorobenzyl)-5-((dimethylamino)methyl)-3-(2-fluoro-3-methoxyphenyl)pyrrolo[2,1-f][1,2,4]triazine-2,4(1H,3H)-dione 13j (55 mg, 0.10 mmol) was dissolved in 4 mL of tetrahydrofuran, and then added with 4-nitrophenyl chloroformate (30 mg, 0.15 mmol) and pyridine (32 mg, 0.40 mmol). After reacting for 3 hours at 30° C., the reaction solution was then added with methoxylamine hydrochloride (25 mg, 0.30 mmol), and reacted for 8 hours under sealing. The reaction was stopped, and the reaction solution was concentrated under reduced pressure. The residues were purified by thin layer chromatography with elution system A for three times to obtain the title compound 1-(4-(1-(2,6-difluorobenzyl)-5-((dimethylamino)methyl)-3-(2-fluoro-3-methoxyphenyl)-2,4-dioxo-1,2,3,4-tetrahydropyrrolo[2,1-f][1,2,4]triazin-6-yl)phenyl)-3-methoxyurea 15 (5 mg, yellow solid), yield: 8.1%.

MS m/z (ESI): 623.4 [M+1]

$^1$H NMR (400 MHz, DMSO-$d_6$) δ 7.90-7.87 (m, 2H), 7.85-7.80 (m, 2H), 7.60 (s, 1H), 7.55-7.25 (m, 4H), 7.09-7.02 (m, 1H), 6.71-6.65 (m, 1H), 4.50 (s, 2H), 3.84 (s, 3H), 3.67 (s, 3H), 3.54 (s, 2H), 2.15 (s, 6H)

Example 16

1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methylurea

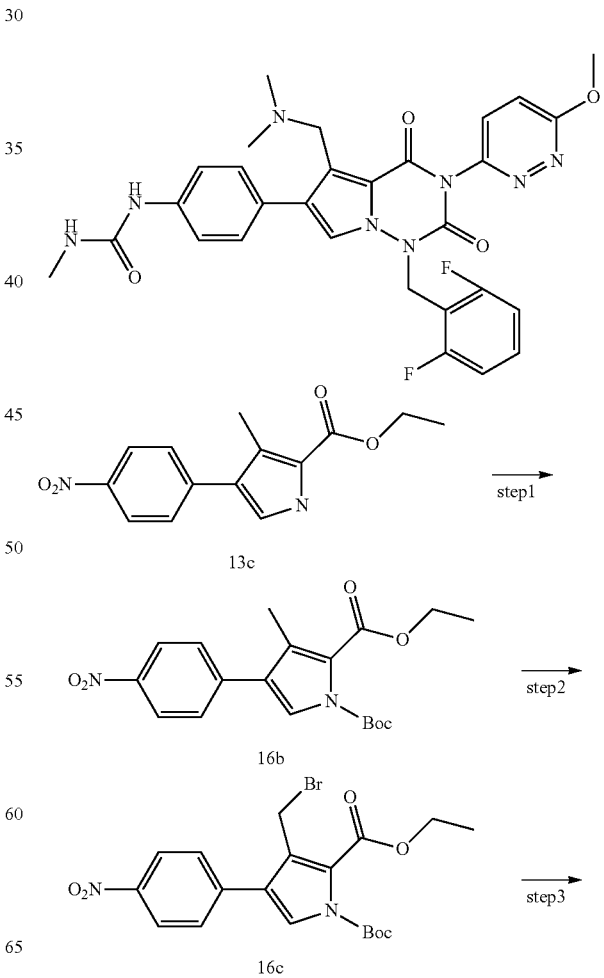

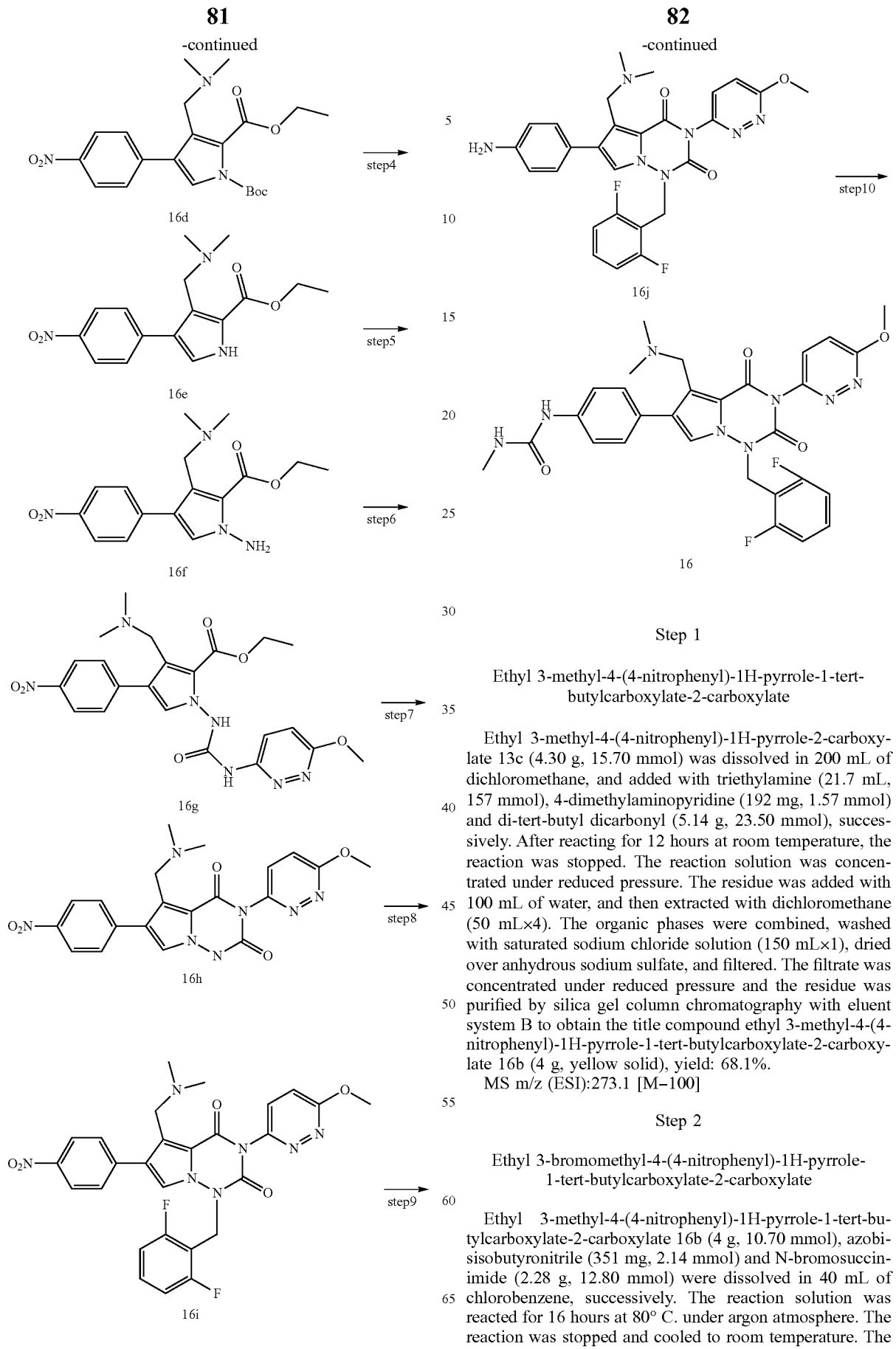

Step 1

Ethyl 3-methyl-4-(4-nitrophenyl)-1H-pyrrole-1-tert-butylcarboxylate-2-carboxylate Ethyl 3-methyl-4-(4-nitrophenyl)-1H-pyrrole-2-carboxylate 13c (4.30 g, 15.70 mmol) was dissolved in 200 mL of dichloromethane, and added with triethylamine (21.7 mL, 157 mmol), 4-dimethylaminopyridine (192 mg, 1.57 mmol) and di-tert-butyl dicarbonyl (5.14 g, 23.50 mmol), successively. After reacting for 12 hours at room temperature, the reaction was stopped. The reaction solution was concentrated under reduced pressure. The residue was added with 100 mL of water, and then extracted with dichloromethane (50 mL×4). The organic phases were combined, washed with saturated sodium chloride solution (150 mL×1), dried over anhydrous sodium sulfate, and filtered. The filtrate was concentrated under reduced pressure and the residue was purified by silica gel column chromatography with eluent system B to obtain the title compound ethyl 3-methyl-4-(4-nitrophenyl)-1H-pyrrole-1-tert-butylcarboxylate-2-carboxylate 16b (4 g, yellow solid), yield: 68.1%.

MS m/z (ESI):273.1 [M−100]

Step 2

Ethyl 3-bromomethyl-4-(4-nitrophenyl)-1H-pyrrole-1-tert-butylcarboxylate-2-carboxylate Ethyl 3-methyl-4-(4-nitrophenyl)-1H-pyrrole-1-tert-butylcarboxylate-2-carboxylate 16b (4 g, 10.70 mmol), azobisisobutyronitrile (351 mg, 2.14 mmol) and N-bromosuccinimide (2.28 g, 12.80 mmol) were dissolved in 40 mL of chlorobenzene, successively. The reaction solution was reacted for 16 hours at 80° C. under argon atmosphere. The reaction was stopped and cooled to room temperature. The reaction solution was concentrated under reduced pressure, and dried in vacuo to obtain the title compound ethyl 3-bromomethyl-4-(4-nitrophenyl)-1H-pyrrole-1-tert-butylcarboxylate-2-carboxylate 16c (5.2 g, yellow solid), which was used directly in the next step.

MS m/z (ESI): 453.0 [M−100]

Step 3

Ethyl 3-(dimethylamino)methyl-4-(4-nitrophenyl)-1H-pyrrole-1-tert-butylcarboxylate-2-carboxylate Ethyl 3-bromomethyl-4-(4-nitrophenyl)-1H-pyrrole-1-tert-butylcarboxylate-2-carboxylate 16c (4.80 g, 10.70 mmol) was dissolved in 50 mL of tetrahydrofuran, and added with a solution of dimethylamine in tetrahydrofuran (26 mL, 53.50 mmol). After reacting for 3 hours at room temperature, the reaction was stopped. The reaction solution was concentrated under reduced pressure, and the residue was purified by silica gel column chromatography with eluant system A to obtain the title compound ethyl 3-(dimethylamino)methyl-4-(4-nitrophenyl)-1H-pyrrole-1-tert-butylcarboxylate-2-carboxylate 16d (3 g, yellow solid), yield: 67.4%.

MS m/z (ESI): 317.0 [M−100]

Step 4

Ethyl 3-((dimethylamino) methyl)-4-(4-nitrophenyl)-1H-pyrrole-2-carboxylate

Ethyl 3-(dimethylamino)methyl-4-(4-nitrophenyl)-1H-pyrrole-1-tert-butylcarboxylate-2-carboxylate 16d (3 g, 7.18 mmol) was dissolved in a 30 mL solution of 2M hydrochloric acid in methanol. After reacting for 3 hours at room temperature, the reaction was stopped, and the reaction solution was concentrated under reduced pressure. The residue was added with 30 mL of saturated sodium carbonate solution, and extracted with dichloromethane (30 mL×4). The organic phases were combined, washed with saturated sodium chloride solution (60 mL×1), dried over anhydrous sodium sulfate, and filtered. The filtrate was concentrated under reduced pressure to obtain the title compound ethyl 3-((dimethylamino)methyl)-4-(4-nitrophenyl)-1H-pyrrole-2-carboxylate 16e (2 g, yellow solid), yield: 90.9%.

MS m/z (ESI): 318.1 [M+1]

Step 5

Ethyl 1-amino-3-((dimethylamino)methyl)-4-(4-nitrophenyl)-1H-pyrrole-2-carboxylate Ethyl 3-((dimethylamino)methyl)-4-(4-nitrophenyl)-1H-pyrrole-2-carboxylate 16e (1.8 g, 5.68 mmol) was dissolved in 20 mL of N,N-dimethylformamide, and added with 60% sodium hydroxide (307 mg, 7.66 mmol). After reacting for 30 minutes at room temperature, the reaction mixture was added with 50 mL of chloramine, and further reacted for 2 hours at room temperature. The reaction was stopped and the reaction solution was added with 200 mL of water, and extracted with ether (50 mL×3). The organic phases were combined, washed with saturated sodium chloride solution (100 mL×1), dried over anhydrous sodium sulfate, and filtered. The filtrate was concentrated under reduced pressure to obtain the title compound ethyl 1-amino-3-((dimethylamino)methyl)-4-(4-nitrophenyl)-1H-pyrrole-2-carboxylate 16f (620 mg, yellow solid), yield: 32.9%.

MS m/z (ESI): 333.2 [M+1]

Step 6

Ethyl 3-((dimethylamino)methyl)-1-(3-(6-methoxypyridazin-3-yl)ureido)-4-(4-nitrophenyl)-1H-pyrrole-2-carboxylate Ethyl 1-amino-3-((dimethylamino)methyl)-4-(4-nitrophenyl)-1H-pyrrole-2-carboxylate 16f (420 mg, 1.26 mmol) was dissolved in 15 mL of dichloromethane, and then added with triethylamine (382 mg, 3.78 mmol), triphosgene (131 mg, 0.44 mmol) and 3-amino-6-methoxypyridazine (236 mg, 1.89 mmol), successively. After reacting for 2 hours at room temperature, the reaction was stopped and the reaction solution was concentrated under reduced pressure. The residue was purified by thin layer chromatography with elution system A to obtain the title compound ethyl 3-((dimethylamino)methyl)-1-(3-(6-methoxypyridazin-3-yl)ureido)-4-(4-nitrophenyl)-1H-pyrrole-2-carboxylate 16g (298 mg, yellow solid), yield: 30.2%.

Step 7

5-((dimethylamino)methyl)-3-(6-methoxypyridazin-3-yl)-6-(4-nitrophenyl)pyrrolo[2,1-f][1,2,4]triazine-2,4(1H,3H)-dione Ethyl 3-((dimethylamino)methyl)-1-(3-(6-methoxypyridazin-3-yl)ureido)-4-(4-nitrophenyl)-1H-pyrrole-2-carboxylate 16g (260 mg, 0.54 mmol) was dissolved in 10 mL of methanol, and then added with sodium methoxide (151 mg, 2.69 mmol). After reacting for 3 hours at 50° C., the reaction was stopped and the reaction solution was concentrated under reduced pressure. The residue was purified by thin layer chromatography with elution system A to obtain the title compound 5-((dimethylamino)methyl)-3-(6-methoxypyridazin-3-yl)-6-(4-nitrophenyl)pyrrolo[2,1-f][1,2,4]triazine-2,4(1H,3H)-dione 16h (76 mg, yellow solid) yield: 32.3%.

MS m/z (ESI): 438.3 [M+1]

Step 8

1-(2,6-difluorobenzyl)-5-((dimethylamino)methyl)-3-(6-methoxypyridazin-3-yl)-6-(4-nitrophenyl)pyrrolo[2,1-f][1,2,4]triazine-2,4(1H,3H)-dione 5-((dimethylamino)methyl)-3-(6-methoxypyridazin-3-yl)-6-(4-nitrophenyl)pyrrolo[2,1-f][1,2,4]triazine-2,4(1H,3H)-dione 16h (78 mg, 0.18 mmol), 2-chloromethyl-1,3-difluorophenyl (35 mg, 0.21 mmol) and potassium carbonate (37 mg, 0.26 mmol) were dissolved in 5 mL of N,N-dimethylformamide. After reacting for 16 hours at 50° C., the reaction was stopped and the reaction solution was concentrated under reduced pressure. The residue was purified by thin layer chromatography with elution systems A to obtain the title compound 1-(2,6-difluorobenzyl)-5-((dimethylamino)methyl)-3-(6-methoxypyridazin-3-yl)-6-(4-nitrophenyl)pyrrolo[2,1-f][1,2,4]triazine-2,4(1H,3H)-dione 16i (72 mg, yellow solid), yield: 72.0%.

MS m/z (ESI): 564.1 [M+1]

Step 9

6-(4-aminophenyl)-1-(2,6-difluorobenzyl)-5-((dimethylamino)methyl)-3-(6-methoxypyridazin-3-yl)pyrrolo[2,1-f][1,2,4]triazine-2,4(1H,3H)-dione 1-(2,6-difluorobenzyl)-5-((dimethylamino)methyl)-3-(6-methoxypyridazin-3-yl)-6-(4-nitrophenyl)pyrrolo[2,1-f][1,2,4]triazine-2,4(1H,3H)-dione 16i (72 mg, 0.13 mmol), iron (29 mg, 0.51 mmol), and ammonium chloride (55 mg, 1.02 mmol) were dissolved in a 20 mL mixture of ethanol and water (V/V=4:1). After reacting for 1 hour at 80° C., the reaction was stopped. The reaction solution was cooled to room temperature, and then added with 20 mL of water, and extracted with dichloromethane (10 mL×4). The organic phases were combined, washed with saturated sodium chloride (10 mL×1), dried over anhydrous sodium sulfate, and filtered. The filtrate was concentrated under reduced pressure. The residue was purified by thin layer chromatography with elution system A to obtain the title compound 6-(4-aminophenyl)-1-(2,6-difluorobenzyl)-5-((dimethylamino)methyl)-3-(6-methoxypyridazin-3-yl)pyrrolo[2,1-f][1,2,4]triazine-2,4(1H,3H)-dione 16j (25 mg, khaki solid), yield: 42.8%.

MS m/z (ESI): 534.3[M+1]

Step 10

1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methylurea Acetic acid (51 kg, 0.84 mmol) was added to a 25 mL sealed tube, and added with 2 mL of toluene, N,N-diisopropylethylamine (163 mg, 1.26 mmol), and diphenylphosphoryl azide (231 mg, 0.84 mmol), successively. The mixture was reacted for 1 hour in the sealed tube. After cooling down to 0° C., the reaction solution was added with 2 mL solution of 6-(4-aminophenyl)-1-(2,6-difluorobenzyl)-5-((dimethylamino)methyl)-3-(6-methoxypyridazin-3-yl)pyrrolo[2,1-f][1,2,4]triazine-2,4(1H,3H)-dione 16j (45 mg, 0.084 mmol) in dichloromethane, and further reacted for 16 hours at 40° C. in the sealed tube. The reaction was stopped, and the reaction solution was concentrated under reduced pressure. The residue was purified by thin layer chromatography with elution system A to obtain the title compound 1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methyl urea 16 (18 mg, white solid), yield: 36.0%.

MS m/z (ESI): 591.3 [M+1]

$^1$H NMR (400 MHz, DMSO-$d_6$) δ 7.92-7.87 (m, 2H), 7.77-7.70 (m, 2H), 7.69 (s, 1H), 7.60-7.55 (m, 1H), 7.25-7.13 (m, 2H), 7.05-6.99 (m, 1H), 6.79-6.71 (m, 1H), 4.48 (s, 2H), 4.06 (s, 3H), 3.54 (s, 2H), 2.75 (s, 3H), 2.16 (s, 6H)

Example 17

1-(4-(7-(2,6-difluorobenzyl)-3-((dimethylamino)methyl)-5-(6-hydroxypyridazin-3-yl)-4,6-dioxo-4,5,6,7-tetrahydro-2H-pyrazolo[3,4-d]pyrimidin-2-yl)phenyl)-3-methoxyurea

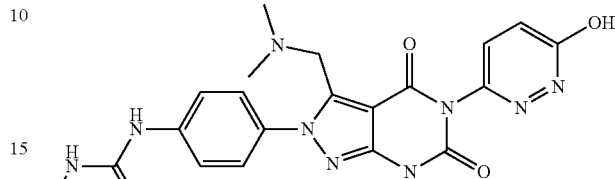

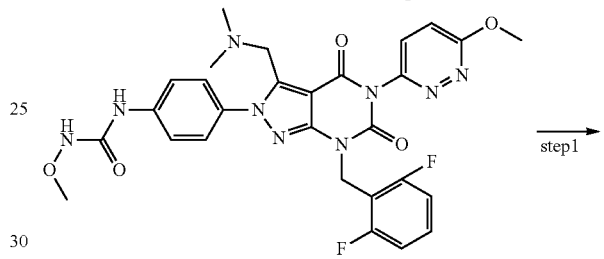

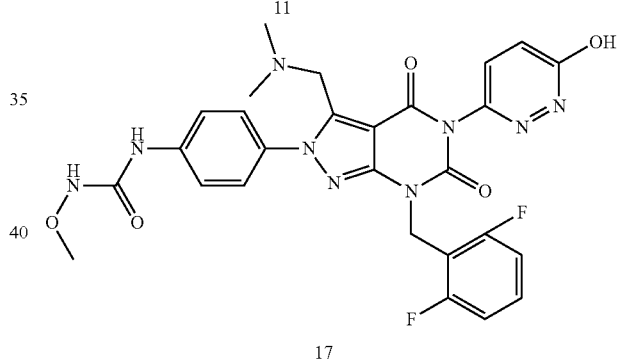

Step 1

1-(4-(7-(2,6-difluorobenzyl)-3-((dimethylamino)methyl)-5-(6-hydroxypyridazin-3-yl)-4,6-dioxo-4,5,6,7-tetrahydro-2H-pyrazolo[3,4-d]pyrimidin-2-yl)phenyl)-3-methoxyurea 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea 11 (122 mg, 0.20 mmol) was dissolved in 6 mL of tetrahydrofuran and stirred until it was dissolved completely. The solution was added with 40% hydrobromic acid (103 mg, 0.51 mmol), and stirred for 12 hours at room temperature. The reaction was stopped, and the reaction solution was added with 5 mL of saturated sodium bicarbonate solution and further stirred for 5 minutes. The resulting mixture was extracted. The organic phases were combined and purified by silica gel column chromatography with elution systems A to obtain the title compound 1-(4-(7-(2,6-difluorobenzyl)-3-

((dimethylamino)methyl)-5-(6-hydroxypyridazin-3-yl)-4,6-dioxo-4,5,6,7-tetrahydro-2H-pyrazolo[3,4-d]pyrimidin-2-yl)phenyl)-3-methoxyurea 17 (16 mg, white solid), yield: 13.5%.

MS m/z (ESI): 594.3 [M+1]

$^1$H NMR (400 MHz, DMSO-$d_6$) δ 13.36-13.18 (m, 1H), 9.69 (s, 1H), 9.21-9.14 (m, 1H), 7.83-7.76 (m, 2H), 7.71-7.64 (m, 2H), 7.52-7.46 (m, 1H), 7.46-7.36 (m, 1H), 7.09 (s, 3H), 5.32-5.21 (m, 2H), 3.71-3.62 (m, 5H), 2.17 (s, 6H)

Example 18

1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methoxyurea

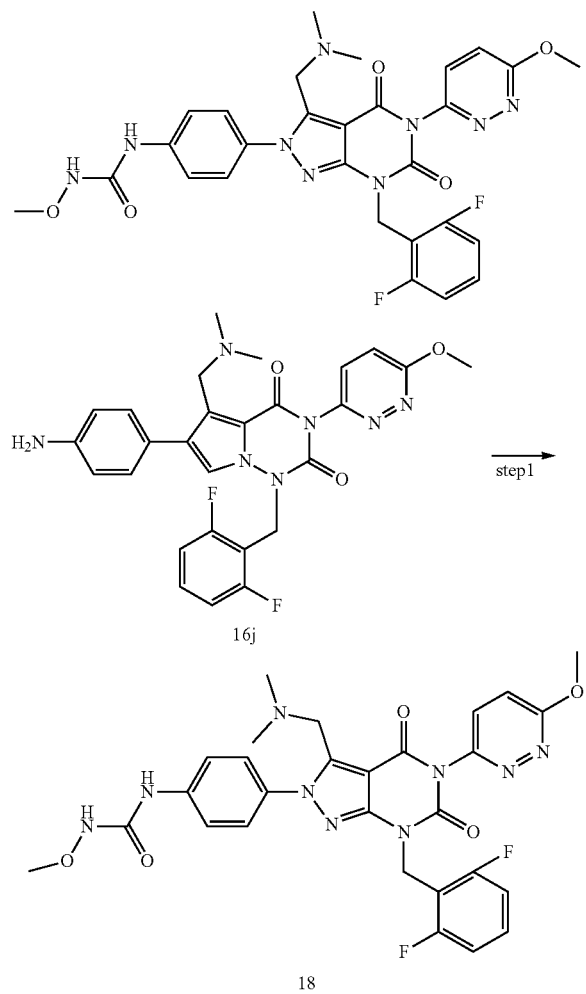

Step 1

1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methoxyurea 6-(4-aminophenyl)-1-(2,6-difluorobenzyl)-5-((dimethylamino)methyl)-3-(6-methoxypyridazin-3-yl)pyrrolo[2,1-f][1,2,4]triazine-2,4(1H,3H)-dione 16j (170 mg, 0.319 mmol), methyl 4-nitrophenylmethoxyamino formate (81 mg, 0.382 mmol, prepared by a known method disclosed in "WO 2011090935") and N,N-diisopropylethylamine (109 μL, 0.638 mmol) were dissolved in 10 mL of tetrahydrofuran. After reacting for 4 hours at room temperature, the reaction was stopped and the reaction solution was concentrated under reduced pressure. The residue was purified by thin layer chromatography with elution system A to obtain the title compound 1-(4-(1-(2,6-difluorobenzyl)-5-((dimethylamino)methyl)-3-(6-methoxypyridazin-3-yl)-2,4-dioxo-1,2,3,4-tetrahydropyrrolo[2,1-f][1,2,4]triazin-6-yl)phenyl)-3-methoxyurea 18 (15 mg, yellow solid), yield: 7.8%.

MS m/z (ESI): 607.2 [M+1]

TEST EXAMPLES

Biological Evaluation

Test Example 1. Human GnRHr (GnRH Receptor) Activity Assay of the Present Compounds.

In vitro GnRHr protein activity was tested by the following methods.

This assay was used to determine the inhibition effect of the present compound on the activity of human GnRHr protein expressed by Human GnRHr/CHO stably transfected cell lines.

1. Experimental Materials and Equipments
   1) Fluo-4 NW Calcium Assay Kits (F36206, Invitrogen)
   2) DMEM/F12 (SH30023.01B, Thermo)
   3) G418 (11811-031, Invitrogen)
   4) FlexStation3 Microplate Reader
2. Experimental Protocol A mammalian expression vector containing the human GnRHr gene was transferred into CHO cells by adding Lipofectamine® LTX reagent containing Plus™. Antibiotics were added the next day for screening to pick out the monoclonal cell lines.

The Human GnRHr/CHO stably transfected cell lines were inoculated in 96-well plates with an inoculation density of 25,000 cells/well. The culture medium was removed the next day, and loading buffer containing Fluo-4 dye was added to the plate (100 μL/well) and incubated for 30 minutes at 37° C. The plate was moved to room temperature and equilibrated for 10 minutes. Each compound was diluted with DMSO to seven concentration gradients of 100 μM, 10 μM, 1 μM, 0.1 μM, 0.01 μM, 0.001 μM, 0.0001 μM. Then, 1 μl of each gradient was added to each well and incubated for 10 minutes at room temperature. After automated addition of 50 μL of GnRH polypeptide stimulant solution, the value was immediately detected at 494/516 nM by a microplate reader (flexstation 3). $IC_{50}$ values of the compounds were calculated by software from different fluorescence signals at various corresponding concentrations.

The inhibitory activity of the present compounds on human GnRHr was determined by the above assay, and $IC_{50}$ values are shown in Table 1.

TABLE 1

Inhibition effect ($IC_{50}$) of the present compounds on the activity of Human GnRHr

| Example No. | $IC_{50}$ (nM) |
| --- | --- |
| 2 | 1.46 |
| 3 | 0.90 |
| 5 | 0.66 |
| 6 | 0.96 |

TABLE 1-continued

Inhibition effect (IC$_{50}$) of the present compounds on the activity of Human GnRHr

| Example No. | IC$_{50}$ (nM) |
|---|---|
| 7 | 0.49 |
| 8 | 0.60 |
| 9 | 0.42 |
| 10 | 0.66 |
| 11 | 4.95 |
| 12 | 2.24 |
| 13 | 0.92 |
| 14 | 0.11 |
| 15 | 0.43 |
| 16 | 2.32 |

Conclusion: The present compounds have significant human GnRHr inhibitory activity.

Test Example 2. Monkey GnRHr Inhibitory Activity Assay of the Present Compounds

This assay was used to determine the inhibition effect of the present compounds on the activity of monkey GnRHr protein expressed by monkey GnRHr/CHO stably transfected cell lines.
1. Experimental Materials and Equipments
   1) Fluo-4 NW Calcium Assay Kits (F36206, Invitrogen)
   2) DMEM/F12 (SH30023.01B, Thermo)
   3) G418 (11811-031, Invitrogen)
   4) FlexStation3 Microplate Reader
2. Experimental Protocol A mammalian expression vector containing the monkey GnRHr gene was transferred into CHO cells by adding Lipofectamine® LTX reagent containing Plus™. Antibiotics were added the next day for screening to pick out the monoclonal cell lines.

The monkey GnRHr/CHO stably transfected cell lines were inoculated in 96-well plates with an inoculation density of 25,000 cells/well. The culture medium was removed the next day, and loading buffer containing Fluo-4 dye was added to the plate (100 μL/well) and incubated for 30 minutes at 37° C. The plate was moved to room temperature and equilibrated for 10 minutes. Each compound was diluted with DMSO to seven concentration gradients of 100 μM, 10 μM, 1 μM, 0.1 μM, 0.01 μM, 0.001 μM, 0.0001 μM. Then, 1 μl of each gradient was added to each well and incubated for 10 minutes at room temperature. After automated addition of 50 L of GnRH polypeptide stimulant solution, the value was immediately detected at 494/516 nM by a microplate reader (flexstation 3). IC$_{50}$ values of the compounds were calculated by software from different fluorescence signals at various corresponding concentrations.

The inhibitory activity of the present compounds on monkey GnRHr was determined by the above assay, and IC$_{50}$ values are shown in Table 1.

TABLE 2

Inhibition effect (IC$_{50}$) of the present compounds on the activity of Monkey GnRHr

| Example No. | IC$_{50}$ (nM) |
|---|---|
| 9 | 23.22 |
| 11 | 78.57 |

Conclusion: The present compounds have significant monkey GnRHr inhibitory activity.

Test Example 3. Rabbit GnRHr Inhibitory Activity Assay of the Present Compounds

This assay was used to determine the inhibition effect of the present compounds on the activity of rabbit GnRHr protein expressed by rabbit GnRHr/CHO stably transfected cell lines.
1. Experimental Materials and Equipments
   1) Fluo-4 NW Calcium Assay Kits (F36206, Invitrogen)
   2) DMEM/F12 (SH30023.01B, Thermo)
   3) G418 (11811-031, Invitrogen)
   4) FlexStation3 Microplate Reader
2. Experimental Protocol A mammalian expression vector containing the rabbit GnRHr gene was transferred into CHO cells by adding Lipofectamine® LTX reagent containing Plus™. Antibiotics were added the next day for screening to pick out the monoclonal cell lines.

The rabbit GnRHr/CHO stably transfected cell lines were inoculated in 96-well plates with an inoculation density of 25,000 cells/well. The culture medium was removed the next day, and loading buffer containing Fluo-4 dye was added to the plate (100 μL/well) and incubated for 30 minutes at 37° C. The plate was moved to room temperature and equilibrated for 10 minutes. Each compound was diluted with DMSO to seven concentration gradients of 100 μM, 10 μM, 1 μM, 0.1 μM, 0.01 μM, 0.001 μM, 0.0001 μM. Then, 1 μl of each gradient was added to each well and incubated for 10 minutes at room temperature. After automated addition of 50 μL of GnRH polypeptide stimulant solution, the value was immediately detected at 494/516n M by a microplate reader (flexstation 3). IC$_{50}$ values of the compounds were calculated by software from different fluorescence signals at various corresponding concentrations.

The inhibitory activity of the present compounds on rabbit GnRHr was determined by the above assay, and IC$_{50}$ values are shown in Table 1.

TABLE 3

IC$_{50}$ of inhibition effect of the present compound on rabbit GnRHr activity

| Example No. | IC$_{50}$ (nM) |
|---|---|
| 8 | 0.27 |
| 9 | 0.24 |
| 11 | 0.57 |

Conclusion: The present compounds have significant rabbit GnRHr inhibitory activity.

Pharmacokinetics Evaluation

Test Example 4. Rat pharmacokinetics assay of the compounds of Example 2, Example 3, Example 5, Example 9, Example 10, Example 11, and Example 13 of the present invention.
1. Summary Sprague-Dawley (SD) rats were used as test animals. The plasma concentrations at various times were determined by LC/MS/MS after intragastric administration of compounds of Example 2, Example 3, Example 5, Example 9, Example 10, Example 11, and Example 13, and intravenous administration of the compound of Example 11 to the rats. The pharmacokinetic behavior of the present compounds in rats was studied, and the pharmacokinetic features were evaluated.

2. Test Protocol
2.1 Samples
Compounds of Example 2, Example 3, Example 5, Example 9, Example 10, Example 11, and Example 13
2.2 Test Animals
Thirty-two (32) healthy adult SD rats (half female and half male) were evenly designated into 8 groups (4 for each group). The animals were purchased from Shanghai Super B&K Laboratory Animal Corp. Ltd (laboratory animal production Certificate No. SCXK (HU)2008-0016).
2.3 Drug Formulation
An appropriate amount of sample was weighed, and added with 0.5% CMC-Na to form a 1 mg/ml suspension upon ultrasonic treatment.
Appropriate amounts of drugs were weighed, and dissolved with 0.5 ml DMSO and 0.5 ml of Tween 80. Saline solution was added to the final volume.
2.4 Administration
Thirty-two (32) SD rats (half female and half male) were evenly designated into 8 groups (4 for each group), and administered by oral gavage or intravenous injection (i.v.) (oral gavage at a dosage of 10 mg/kg or 30 mg/kg, and i.v. at a dosage of 5.0 mg/kg), respectively, at a volume of 10 ml/kg after fasting overnight.
3. Operation
0.1 ml of blood was sampled before, and 0.5, 1, 2, 4, 6, 8, 11, and 24 hours after administration, collected in a heparinized test tube, and centrifuged at 3500 rpm for 10 minutes to separate the plasma, which was stored at −20° C. The animals were allowed access to feed 2 hours after administration.
The content of the test compound in the plasma of rats after administration of the compound by oral gavage was determined by LC/MS/MS.
4. Pharmacokinetic Parameters Results
Pharmacokinetic parameters of the present compounds are shown in the following Table 4:

Example 11, and intravenous administration of the compound of Example 11 to rabbits. The pharmacokinetic behavior of the present compound in rabbits was studied, and the pharmacokinetic features were evaluated.
2. Test Protocol
2.1 Sample
Compound of Example 11
2.2 Test Animals
Six (6) healthy New Zealand Rabbits (female) were evenly designated into 2 groups. The animals were purchased from Jie Sijie Corp. Ltd.
2.3 Drug Formulation
An appropriate amount of sample was weighed, and added with 0.5% CMC-Na to form 3 mg/ml suspension upon ultrasonic treatment.
Appropriate amounts of drugs were weighed, and dissolved with 1 ml DMSO and 1 ml of Tween 80. Saline solution was added to the final volume.
2.4 Administration
Six (6) healthy New Zealand rabbits (female) were evenly designated into 2 groups, and administered by oral gavage or intravenous injection (i.v.) (oral gavage at a dosage of 30 mg/kg with an administration volume of 5 ml/kg, and i.v. at a dosage of 5 mg/kg with an administration volume of 2 ml/kg) after fasting overnight.
3. Operation
0.2 ml of blood was sampled before and 5 minutes, 0.25, 0.5, 1, 2, 4, 8, 11, 24 hours after intravenous administration, collected in a heparinized test tube, and centrifuged at 3500 rpm for 10 minutes to separate the plasma, which was stored at −20° C. Blood was sampled before, and 0.5, 1, 2, 4, 6, 8, 11, and 24 hours after oral administration, and treated the same as that of the intravenous administration group. The content of the test compound in the plasma of rabbits after administration of the compound by oral gavage and intravenous injection was determined by LC/MS/MS.
4. Pharmacokinetic Parameters Results
Pharmacokinetic parameters of the present compounds are shown in the following Table 5:

| | | | Rat Pharmacokinetic test (10 mg/kg) | | | | |
|---|---|---|---|---|---|---|---|
| Example No. | Oral Bioavailability F (%) | Plasma concentration $C_{max}$ (ng/mL) | Area under curve AUC (ng/mL*h) | Half-life $T_{1/2}$ (h) | Residence time MRT (h) | Clearance rate CL/F (ml/min/kg) | Apparent volume of distribution Vz/F (ml/kg) |
| 2 | — | 746 ± 493 | 1546 ± 650 | 1.24 ± 0.54 | 2.02 ± 0.67 | 121 ± 44 | 14406 ± 10470 |
| 3 | — | 237 ± 158 | 1072 ± 472 | 6.17 ± 0.79 | 6.42 ± 1.39 | 181 ± 79 | 96163 ± 42245 |
| 5 | — | 690 ± 660 | 1290 ± 1028 | 2.32 ± 0.65 | 2.47 ± 0.75 | 247 ± 198 | 46774 ± 39154 |
| 9 | — | 146 ± 59 | 628 ± 369 | 2.91 ± 1.64 | 4.67 ± 2.22 | 332 ± 159 | 72021 ± 24995 |
| 10 | — | 598 ± 431 | 1237 ± 593 | 2.29 ± 0.84 | 2.96 ± 0.17 | 168 ± 95 | 30330 ± 14422 |
| 11 | 76.6 | 2438 ± 873 (oral10 mg/kg) | 4092 ± 1439 | 0.84 ± 0.18 | 1.56 ± 0.34 | 44.2 ± 13.4 | 3287 ± 1512 |
| | | i.v. (5 mg/kg) 2673 ± 1243 | 1.59 ± 0.50 | 2.25 ± 0.06 | 35.4 ± 12.5 | 4929 ± 2390 | |
| 13 | — | 103 ± 64 | 389 ± 298 | 3.31 ± 0.57 | 4.48 ± 0.70 | 915 ± 1046 | 231402 ± 233610 |

Conclusion: The present compounds are well absorbed orally in rats, and have obvious pharmacokinetic absorption. Example 11 has particularly preferable oral bioavailability.

Test Example 5. Rabbit Pharmacokinetics Assay of Example 11 of the Present Invention 1. Summary
Rabbits were used as test animals. The plasma concentrations at various times were determined by LC/MS/MS after intragastric administration of the compound of

| | | | Rabbit Pharmacokinetic test | | | | |
|---|---|---|---|---|---|---|---|
| No | Oral Bioavailability F (%) | Plasma concentration $C_{max}$ (ng/mL) | Area under curve AUC (ng/mL*h) | Half-life $T_{1/2}$ (h) | Residence time MRT (h) | Clearance rate CL/F (ml/min/kg) | Apparent volume of distribution Vz/F (ml/kg) |
| 11 | 92.9 | 5043 ± 776 (oral 30 mg/kg) | 19008 ± 2312 | 4.57 ± 1.06 | 3.94 ± 0.55 | 26.6 ± 3.4 | 10719 ± 3862 |
| | | 3411 ± 832 intravenous injection (5 mg/kg) | | 4.60 ± 2.70 | 2.39 ± 0.30 | 25.3 ± 5.5 | 10948 ± 7749 |

Conclusion: The compound of Example 11 of the present invention is well absorbed in rabbits, and has preferable oral bioavailability.

Test Example 6. Beagle Pharmacokinetics Assay of Example 11 of the Present Invention 1. Summary Beagles were used as test animals. The plasma concentrations at various times were determined by LC/MS/MS after intragastric administration of the compound of Example 11, and intravenous administration of the compound of Example 11 to beagles. The pharmacokinetic behavior of the present compound in beagles was studied, and the pharmacokinetic features were evaluated.

2. Test Protocol 2.1 Sample

Compound of Example 11

2.2 Test Animals

Eight (8) healthy beagles (half female and half male) were evenly designated into 2 groups. The animals were purchased from SuzhouXishan Zhongke Laboratory Animal Corp. Ltd.

2.3 Drug Formulation

An appropriate amount of sample was weighed, and added with 0.5% CMC-Na to form a 1.0 mg/ml suspension upon ultrasonic treatment;

Appropriate amounts of drugs were weighed, and dissolved with 5 ml DMSO and 5 ml of Tween 80. Saline solution was added to the final volume.

2.4 Administration

Eight (8) healthy beagles (half female and half male) were evenly designated into 2 groups, and administered by oral gavage or intravenous injection (i.v.) (oral gavage at a dosage of 5 mg/kg with an administration volume of 5 ml/kg, and i.v. at a dosage of 2 mg/kg with an administration volume of 2 ml/kg) after fasting overnight.

3. Operation 1.0 ml of blood was sampled from the foreleg vein before, and 0.25, 0.5, 1, 2, 4, 6, 8, 12, and 24 hours after oral administration, collected in a heparinized test tube, and centrifuged at 3500 rpm for 10 minutes to separate the plasma, which was stored at −20° C. The animals were allowed access to feed 2 hours after administration. Blood was sampled before, and 5 minutes, 0.25, 0.5, 1, 2, 4, 6, 8, 12, and 24 hours after intravenous administration, and treated the same as above. The content of the test compound in the plasma of beagles after administration of the compound by oral gavage and intravenous injection was determined by LC/MS/MS.

4. Pharmacokinetic Parameters Results

Pharmacokinetic parameters of the present compounds are shown in the following Table 6:

| | | | Beagle Pharmacokinetic test | | | | |
|---|---|---|---|---|---|---|---|
| No. | Oral Bioavailability F (%) | Plasma concentration $C_{max}$ (ng/mL) | Area under curve AUC (ng/mL*h) | Half-life $T_{1/2}$ (h) | Residence time MRT (h) | Clearance rate CL/F (ml/min/kg) | Apparent volume of distribution Vz/F (ml/kg) |
| 11 | 103.5 | 1087 ± 350 (oral 5 mg/kg) | 5942 ± 1345 | 5.37 ± 1.52 | 6.40 ± 2.82 | 14.7 ± 4.2 | 7246 ± 4373 |
| | | 2296 ± 213 i.v. (2 mg/kg) | | 3.34 ± 0.40 | 4.02 ± 0.50 | 14.6 ± 1.3 | 4235 ± 706 |

Conclusion: The compound of Example 11 of the present invention is well absorbed in beagles, and has preferable oral bioavailability.

Test Example 7. In Vivo Pharmacodynamics Test of Example 11 of the Present Invention in Rabbit 1. Summary An endometriosis model was established in rabbits, and a pharmacodynamic screening test for rabbit endometriosis treated by the compound of Example 11 was implemented.

2. Test Protocol 2.1 Sample

Compound of Example 11

2.2 Test Animals

Fifteen (15) healthy New Zealand rabbits (female) were evenly designated into 3 groups. The animals were purchased from Shanghai Songjiang District Songlian Laboratory Animal Farm (laboratory animal production Certificate No. SCXK (HU) 2008-0016).

2.3 Operation

Rabbits were adaptive fed and quarantined for seven days, and subcutaneously injected with 30 μg/kg of estradiol benzoate once daily for two days before surgery. When the model was established, rabbits were anesthetized with 3% sodium pentobarbital, and laparotomized sterilely. Then, one side of the uterus was separated and ligated with the uterine mesorectum vessel. Then, a section of the uterus was cut off and put into a warm saline dish, and then dissected longitudinally and the myometrium and endometrium were separated. A section of endometrium (about 0.5 cm by 0.5 cm) was seamed to the abdominal wall rich in blood vessels with the intimal surface facing toward the abdominal cavity. Three weeks after endometrium planting, the rabbits were laparotomized to check graft intimal size. 15 animals of successful modeling were randomly divided into 3 groups (5 for each group), which were vehicle control group, low-dose group (10 mg/kg of the compound of Example 11), and high-dose group (30 mg/kg of the compound of Example 11), respectively. Each group was administered by oral gavage once a day in a volume of 5 ml/kg, continuously for 28 days after successful modeling. Ultimately, the rabbit was weighed and the volume of ectopic endometrium was measured to evaluate the effect of the present compound on the endometrial activity.

2.4 Results:

After 30 mg/kg administration of the compound of Example 11 to the rabbit endometriosis model for 4 weeks with oral administration of the same amount of 0.5% CMC-Na as a control, the growth of ectopic endometrium was significantly inhibited, while the inhibition of the compound of Example 11 for the ectopic endometrial volume at 10 mg/kg was not obvious. Therefore, the toxicologic NOAEL dose (dose under which no damage effect dose was observed) of the compound of Example 11 in the rabbit endometriosis model is 30 mg/kg.

Test Example 8. Seven-Day Toxicokinetic Evaluation of the Compound of Example 11 in Rats 1. Summary SD rats were used as test animals. The plasma concentration at various times was determined by LC/MS/MS after administration of the compound of Example 11 (SHR147280) by oral gavage for 7 days. The compound toxicity in rodents was preliminarily assessed according to the potential toxicity reaction and severity level of the body.

2. Test Protocol 2.1 Sample

Compound of Example 11

2.2 Test Animals

Twenty-four (24) healthy adult SD rats (half female and half male) were evenly designated into 4 groups (6 for each group). The animals were purchased from Shanghai SLAC Laboratory Animal Corp. Ltd (laboratory animal production Certificate No. SCXK (HU) 2012-0002).

2.3 Drug Formulation

An appropriate amount of sample was accurately weighed, and added with some 0.5% CMC-Na to form an uniform suspension upon ultrasonicator grinding treatment, and then diluted to the final volume. The test sample solutions on day 1 and day 7 were kept for the determination of administration concentration of toxicokinetics.

2.4 Administration

Repeat oral doses were 80, 240, and 720 mg/kg, and administration concentrations were 8, 24, and 72 mg/ml respectively. The dosing volume was 10 ml/kg once daily for 7 days.

3. Operation

The blood was sampled on day 1 and day 7 after administration with sampling time before, and 1, 2, 4, 8 and 24 hours after oral administration on day 1, as well as before, and 1, 2, 4, 8, 24 and 48 hours after oral administration on day 7. The blood sample was collected in a heparinized test tube, and centrifuged to separate the plasma, which was stored at −20° C. The content of the test compound in the plasma of rats after administration of the compound by oral gavage was determined by LC/MS/MS.

4. Results 4.1. Impact on clinical signs 4.1.1 Death

Rat No. 1 in the 720 mg/kg toxicity group of the compound of Example 11 died on day 7 before dosing. Rat No. 5 in the 720 mg/kg toxicokinetic group of the compound of Example 11 died on day 7 before dosing, and No. 6 died on day 9.

4.1.2 Clinical Observation

During the administration, compared with the vehicle control group, rats in the 720 mg/kg toxicity group and toxicokinetic group all showed weight loss and poor mental state after administration of the compound of Example 11 on day 6. Rats in the 720 mg/kg toxicity group and toxicokinetic group after administration of the compound of Example 11 on day 7 all showed food intake reduction, weight loss, lessened activity, poor mental state, dull back fur, hair stand, roachback, haemorrhage around the nose and eyes, diarrhea, and filthy crissum.

4.2. Impact on Body Weight

Compared with the vehicle control group, the weight change percentage of the high dose group exhibited a significant decrease (P<0.05) after administration of the compound of Example 11 on day 3 and day 7.

4.3 Impact on Food Intake

Compared with the vehicle control group, the food intake of the group treated with the compound SHR147280 at 720 mg/kg dose level was significantly reduced on day 3 and day 7.

4.4. Hematology Test Results

Compared with the vehicle control group, WBC (white blood cells), Neut (neutrophils relative value and absolute neutrophils count), Lymph (absolute lymphocyte count), EO (absolute eosinophils cell count), and RET (reticulocyte relative value and absolute reticulocyte count) of rats in the 720 mg/kg dose group of the compound of Example 11 were significantly decreased (P<0.05).

4.5. Blood Biochemical Test Results

Compared with the vehicle control group, BUN (blood urea nitrogen), CHOL (total cholesterol), CREA (creatinine), TBIL (total bilirubin), TP (total protein), and AST (aspartate aminotransferase) of rats in the 720 mg/kg dose group of the compound of Example 11 were significantly increased (P<0.05). Although there were no statistical differences in ALT (alanine aminotransferase), the ALT of two animals was significantly increased. ALB (albumin) and ALP (alkaline phosphatase) were significantly decreased (P<0.05), whereas the ion detection result was lacking for the shortage of blood samples of the SHR 147280 720 mg/kg dose group. No other obvious toxicological abnormalities were detected.

4.6. Coagulation Parameters

Compared with the vehicle control group, rats in the 80 mg/kg dose group and 240 mg/kg dose group of the compound of Example 11 did not show a significant difference. Coagulation parameters result was lacking for the shortage of blood samples of the SHR 147280 720 mg/kg dose group.

4.7. The Urine Test

Compared with the vehicle control group, the treatment groups showed no regularly abnormal changes in urine indexes.

4.8. General Pathology Results

Autopsy was generally visible. Compared with the vehicle control group, the 720 mg/kg dose group of the compound of Example 11 exhibited thymus hemorrhage and atrophy; spleen atrophy and congestion; varying degrees of congestion in leaves of the liver with flaky grayred necrotic lesions; lung hyperaemia and hemorrhage; adrenal gland hemorrhage and hypertrophy; ovary hemorrhage and congestion; gastrointestinal wall thinning; white contents in the stomach; and yellow contents in the small intestine, intestinal hemorrhage, colon rectal hemorrhage, and intestine mucoid. In addition, the dead animals showed cardiac necrotic lesions. The rest of the groups presented no visible abnormality.

4.9. Organ Coefficient Results

Compared with the vehicle control group, the absolute wet weight of the thymus, heart, lung and spleen in male and female rats of the 720 mg/kg group of the compound of Example 11 was significantly decreased ($p<0.05$). In contrast, the absolute wet weight of the adrenal gland was significantly increased ($p<0.05$). The Relative organ coefficient of the thymus and spleen was significantly reduced ($p<0.05$), whereas the relative organ coefficient of the brain, liver, lung, kidney, and adrenal gland was significantly increased ($p<0.05$).

4.10. Toxicokinetic Parameters Results

Toxicokinetic Parameters of Female Rats after Intragastric Administration

| Parameter | Group | | | | | |
|---|---|---|---|---|---|---|
| | 80 mg/kg | | 240 mg/kg | | 720 mg/kg | |
| | Day 1 | Day 7 | Day 1 | Day 7 | Day 1 | Day 7 |
| $t_{max}$(h) | 1.5 | 4.0 | 8.0 | 6.0 | 16.0 | 24.0 |
| $C_{max}$(ng/ml) | 17800 | 19550 | 41500 | 51150 | 69300 | 138000 |
| $AUC_{0-t}$(ng/ml*h) | 173185 | 282074 | 639265 | 790873 | 1546150 | 2838650 |
| $AUC_{0-\infty}$(ng/ml*h) | 173968 | 313468 | 690196 | 840450 | — | — |
| $t_{1/2}$(h) | 3.15 | 6.79 | 5.73 | 4.26 | — | — |
| CLz/F(ml/min/kg) | 7.71 | — | 5.82 | — | — | — |
| Vz/F(ml/kg) | 2092 | — | 2871 | — | — | — |
| $MRT_{0-\infty}$(h) | 5.82 | 9.23 | 9.63 | 7.97 | — | — |

Note:
"—" indicates that the parameter cannot be calculated for the lack of data.

Therefore, toxicology NOAEL dose of Example 11 is 240 mg/kg, and the lethal dose is 720 mg/kg. The potential toxic target organs were marrow hematopoietic system, thymus, heart, liver, lung, spleen, adrenal gland, ovary, and digestion system.

In conclusion: Comparing the pharmacokinetic test of Test Example 5, pharmacodynamic test of Test Example 7, and toxicological pharmacokinetic test of Test Example 8, the preliminary evaluation of the safety window of the compound in Example 11 was as follows:

| Test comparison | NOAEL dose (mg/kg) (toxicological pharmacokinetic dose/ pharmacodynamic dose) | AUC (ng/ml * h) (in vivo exposure/ pharmacokinetic exposure) |
|---|---|---|
| Example 11 | 240/30 = 8 | 840450/ (19008 ± 2312) = 39.4 or 50.3 |

We claim:

1. A process for preparing the compound of formula (II), or a tautomer, mesomer, racemate, enantiomer, or diastereomer thereof, or mixture thereof, or a pharmaceutically acceptable salt thereof:

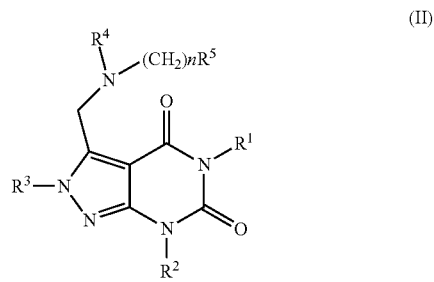

the process comprising:

(a) reacting a compound of formula (IA) with an amine of formula NH(R⁴)(CH₂)nR; and optionally reducing and/or acylating the resulting product to obtain the compound of formula (II); or (b) reacting a compound of formula (IB) with R²X in the presence of an alkaline reagent; and optionally reducing and/or acylating the resulting product to obtain the compound of formula (II):

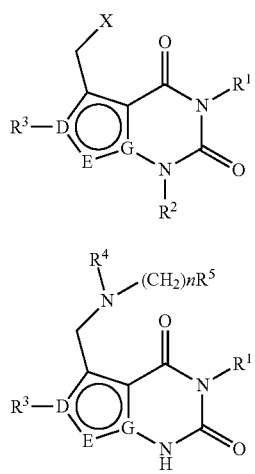

wherein:
X is halogen;
G is C;
D and E are each N;
R$^1$ is selected from the group consisting of alkyl, cycloalkyl, heterocyclyl, aryl, heteroaryl, and —OR$^6$, wherein the alkyl, cycloalkyl, heterocyclyl, aryl, and heteroaryl are each independently and optionally further substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —OR$^6$, —C(O)OR$^6$, —OC(O)R$^6$, —NHS(O)$_m$R$^6$, —C(O)R$^6$, —NHC(O)R$^6$, —NHC(O)OR$^6$, —NR$^7$R$^8$, —OC(O)NR$^7$R$^8$, —C(O)NR$^7$R$^8$, —NHC(O)NHR$^6$, and —NHC(O)NHOR$^6$;
R$^2$ is alkyl, wherein the alkyl is further substituted with one or more groups consisting of aryl and heteroaryl, wherein the aryl and heteroaryl are each optionally further substituted with one or more groups selected from the group consisting of halogen, alkyl, haloalkyl, cyano, nitro, —C(O)OR$^6$, —C(O)NR$^7$R$^8$, —OC(O)NR$^7$R$^8$, —OR$^6$, —NHS(O)$_m$R$^6$, —NHC(O)R$^6$, and —NR$^7$R$^8$;
R$^3$ is selected from the group consisting of aryl and heteroaryl, wherein the aryl and heteroaryl are each optionally further substituted with one or more groups selected from the group consisting of halogen, alkyl, haloalkyl, —OR$^6$, —C(O)OR$^6$, —OC(O)R$^6$, —C(O)R$^6$, —NR$^7$R$^8$, —OC(O)NR$^7$R$^8$, —C(O)NR$^7$R$^8$, —NHS(O)$_m$R$^6$, —NHC(O)R$^6$, —NHC(O)OR$^6$, —NHC(O)NHR$^6$, and —NHC(O)NHOR$^6$;
R$^4$ is alkyl;
R$^5$ is selected from the group consisting of hydrogen, cycloalkyl, heterocyclyl, aryl, heteroaryl, —OR$^5$, —NR$^7$R$^8$, and —NR$^7$S(O)$_m$R$^6$, wherein the alkyl, cycloalkyl, heterocyclyl, aryl, and heteroaryl are each optionally further substituted with one or more groups selected from the group consisting of halogen, oxo, alkyl, haloalkyl, hydroxyalkyl, —OR$^6$, —C(O)OR$^6$, —OC(O)OR$^6$, —NR$^7$S(O)$_m$R$^6$, —S(O)$_m$R$^6$, —C(O)R$^6$, and —NHC(O)R$^6$;
R$^6$ is selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally further substituted with one or more groups selected from the group consisting of alkyl, halogen, hydroxy, alkoxy, cycloalkyl, heterocyclyl, aryl, heteroaryl, carboxylic acid, and carboxylic ester;

R$^7$ and R$^8$ are each independently selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally further substituted with one or more groups selected from the group consisting of alkyl, halogen, hydroxy, alkoxy, cycloalkyl, heterocyclyl, aryl, heteroaryl, carboxylic acid, and carboxylic ester;

or, R$^7$ and R$^8$ are taken together with the attached N atom to form a heterocyclyl, wherein the heterocyclyl contains one or more heteroatoms selected from the group consisting of N, O, and S(O)$_m$, and the heterocyclyl is optionally further substituted with one or more groups selected from the group consisting of alkyl, halogen, hydroxyl, alkoxyl, cycloalkyl, heterocyclyl, aryl, heteroaryl, carboxylic acid, and carboxylic ester;

m is 0, 1, or 2;

n is 1, 2, 3, or 4; and p is 0, 1, or 2.

2. The process according to claim 1, wherein the process comprises reacting a compound of formula (IA) with an amine of formula NH(R$^4$)(CH$_2$)nR$^5$; and optionally reducing and/or acylating the resulting product to obtain the compound of formula (II).

3. The process according to claim 1, wherein the process comprises reacting a compound of formula (IB) with R$^2$X in the presence of an alkaline reagent; and optionally reducing and/or acylating the resulting product to obtain the compound of formula (II).

4. The process according to claim 1, wherein R$^1$ is selected from the group consisting of aryl and heteroaryl, wherein the aryl and heteroaryl are each optionally further substituted with one or more groups selected from the group consisting of halogen, cyano, nitro, alkyl, haloalkyl, hydroxyalkyl, and —OR$^6$.

5. The process according to claim 1, wherein R$^2$ is benzyl, wherein the benzyl is optionally substituted with one or more groups selected from the group consisting of halogen, alkyl, haloalkyl, cyano, nitro, and —OR$^6$.

6. The process according to claim 1, wherein R$^3$ is aryl, wherein the aryl is optionally further substituted with one or more groups selected from the group consisting of —NHC(O)R$^6$, —NHC(O)OR$^6$, —NHC(O)NHR$^6$ and —NHC(O)NHOR$^6$.

7. The process according to claim 1, wherein R$^4$ is methyl.

8. The process according to claim 1, wherein R$^5$ is hydrogen, and n is 1 or 2.

9. The process according to claim 1, wherein R$^1$ is optionally substituted phenyl or optionally substituted pyridazinyl.

10. The process according to claim 1, wherein the compound is a compound of formula (IV), a tautomer, mesomer, racemate, enantiomer, or diastereomer thereof, or mixture thereof, or a pharmaceutically acceptable salt thereof:

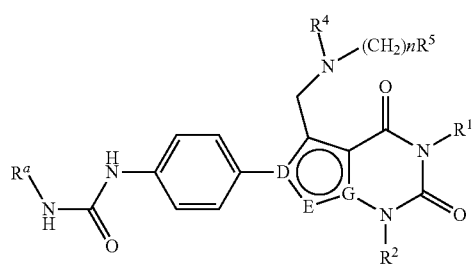

(IV)

wherein:

G is C;

D and E are each N;

R[a] is selected from the group consisting of alkyl and —OR[6], wherein the alkyl is optionally further substituted with one or more groups selected from the group consisting of alkyl, halogen, hydroxy, alkoxy, cycloalkyl, heterocyclyl, aryl, heteroaryl, carboxylic acid, and carboxylic ester; and R[6] is alkyl, wherein the alkyl is optionally substituted with one or more groups selected from the group consisting of alkyl, halogen, hydroxy, alkoxy, cycloalkyl, heterocyclyl, aryl, heteroaryl, carboxylic acid, and carboxylic ester.

11. The process according to claim 1, wherein the compound is selected from the group consisting of:

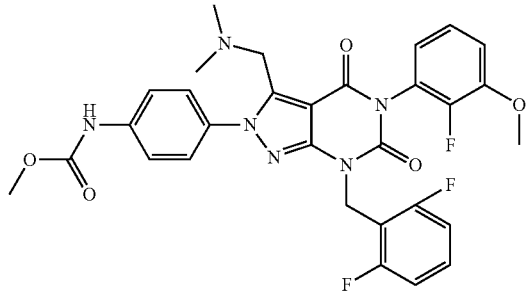

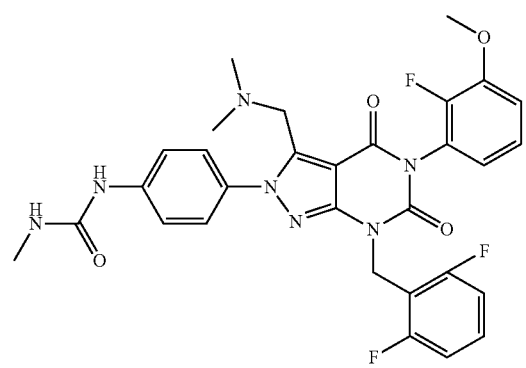

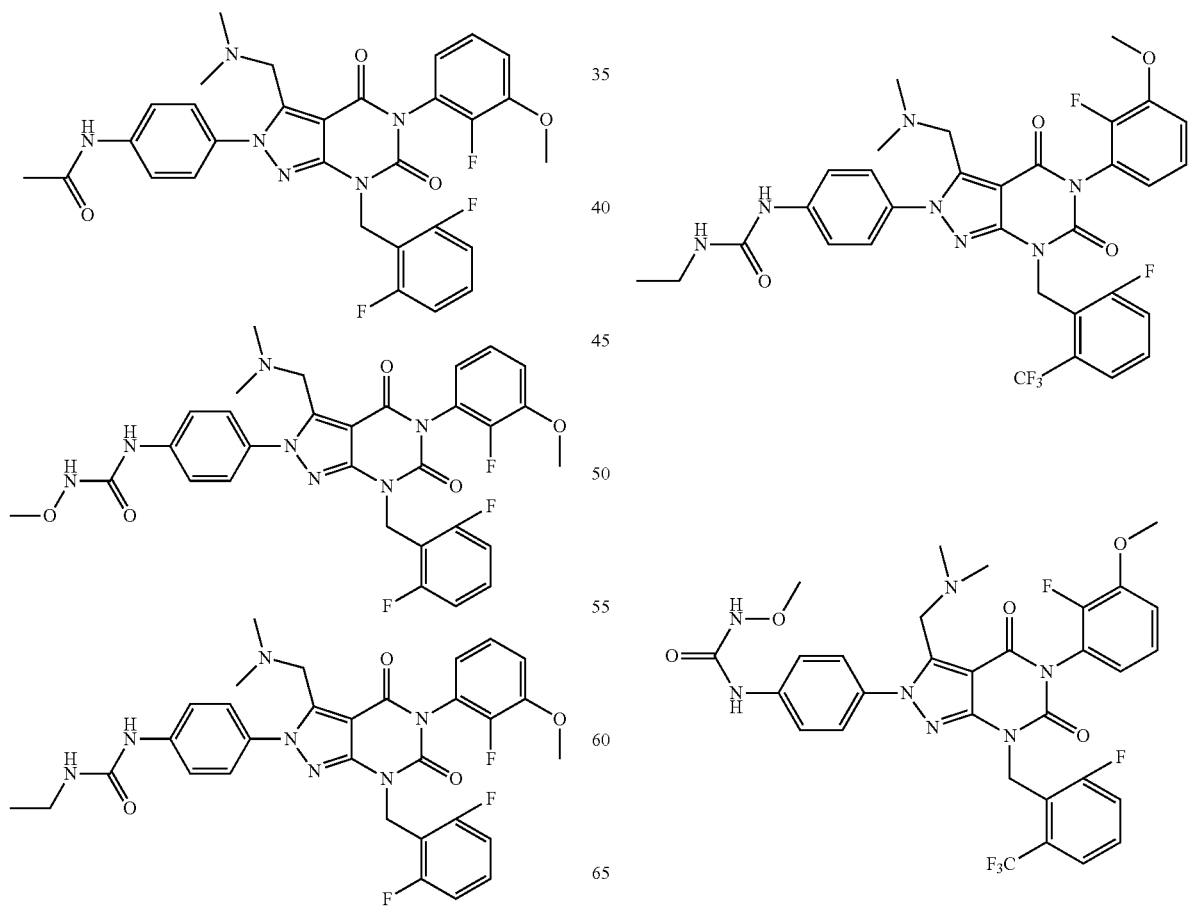

103
-continued
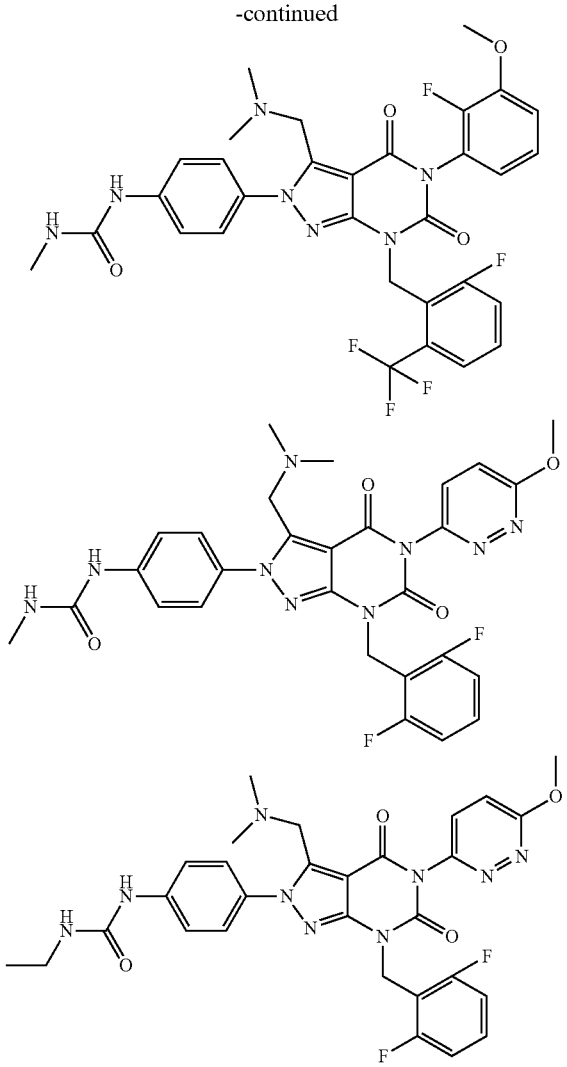
104
-continued
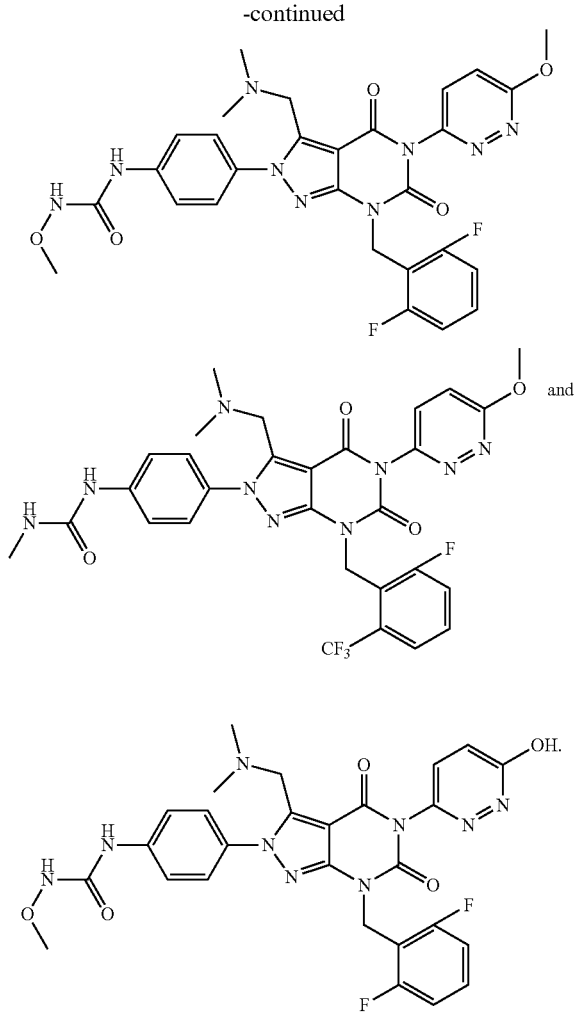
and
* * * * *